US012765891B2

(12) United States Patent
Nielsen et al.

(10) Patent No.: US 12,765,891 B2
(45) Date of Patent: Oct. 20, 2026

(54) SOFT TISSUE MEASUREMENT AND BALANCING SYSTEMS AND METHODS

(71) Applicant: OrthAlign, Inc., Aliso Viejo, CA (US)

(72) Inventors: Jonathan Nielsen, Aliso Viejo, CA (US); Matthew Yacono, Lake Forest, CA (US)

(73) Assignee: OrthAlign, Inc., Irvine, CA (US)

( * ) Notice: Subject to any disclaimer, the term of this patent is extended or adjusted under 35 U.S.C. 154(b) by 210 days.

(21) Appl. No.: 18/461,034

(22) Filed: Sep. 5, 2023

(65) Prior Publication Data

US 2024/0099731 A1 Mar. 28, 2024

Related U.S. Application Data

(63) Continuation of application No. 17/111,938, filed on Dec. 4, 2020, now Pat. No. 11,786,261, which is a (Continued)

(51) Int. Cl.

| | |
|---|---|
| ***A61B 17/17*** | (2006.01) |
| ***A61B 5/00*** | (2006.01) |
| ***A61B 5/06*** | (2006.01) |
| ***A61B 5/107*** | (2006.01) |
| ***A61B 17/15*** | (2006.01) |

(Continued)

(52) U.S. Cl.

CPC .......... *A61B 17/1764* (2013.01); *A61B 5/067* (2013.01); *A61B 5/1071* (2013.01); *A61B 5/4528* (2013.01); *A61B 17/155* (2013.01); *A61B 17/157* (2013.01); *A61B 17/1703* (2013.01); *A61B 90/06* (2016.02); *A61B 2017/00407* (2013.01);

(Continued)

(58) Field of Classification Search

CPC ................................ A61B 17/17; A61B 90/06

See application file for complete search history.

(56) References Cited

U.S. PATENT DOCUMENTS

| | | | |
|---|---|---|---|
| 3,174,080 | A | 3/1965 | Eldon |
| 3,670,324 | A | 6/1972 | Trevor, III |

(Continued)

FOREIGN PATENT DOCUMENTS

| | | |
|---|---|---|
| CA | 2241359 | 12/1999 |
| CA | 2 594 874 | 7/2006 |

(Continued)

OTHER PUBLICATIONS 510 (k) Summary for Total Knee Surgetics Navigation System, in 5 pages.

(Continued)

*Primary Examiner* — Zade Coley

(74) *Attorney, Agent, or Firm* — Knobbe, Martens, Olson & Bear, LLP

(57) ABSTRACT

Systems and methods for joint replacement are provided. The systems and methods can include a surgical orientation device and/or a reference sensor device. The surgical orientation device and orthopedic fixtures can be used to locate the orientation of an axis in the body, to adjust an orientation of a cutting plane or planes along a bony surface, to distract a joint, to measure an angle, to orient a cutting guide, to orient a resection guide, to resect the femur, or to otherwise assist in an orthopedic procedure or procedures.

18 Claims, 50 Drawing Sheets

Related U.S. Application Data continuation of application No. 15/920,202, filed on Mar. 13, 2018, now Pat. No. 10,863,995.

(60) Provisional application No. 62/471,177, filed on Mar. 14, 2017.

(51) Int. Cl.
*A61B 90/00* (2016.01)
*A61B 17/00* (2006.01)

(52) U.S. Cl.
CPC ... *A61B 2090/061* (2016.02); *A61B 2090/064* (2016.02); *A61B 2090/067* (2016.02)

(56) References Cited

U.S. PATENT DOCUMENTS 4,349,018 A 9/1982 Chambers
4,421,112 A 12/1983 Mains et al.
4,436,099 A 3/1984 Raftopoulos
4,459,985 A 7/1984 McKay et al.
4,475,549 A 10/1984 Oh
4,501,266 A 2/1985 McDaniel
4,509,393 A 4/1985 Castiglione
4,518,855 A 5/1985 Malak
4,524,766 A 6/1985 Petersen
4,529,348 A 7/1985 Johnson et al.
4,567,885 A 2/1986 Androphy
4,567,886 A 2/1986 Petersen
4,621,630 A 11/1986 Kenna
4,646,729 A 3/1987 Kenna
4,716,894 A 1/1988 Lazzeri et al.
4,718,078 A 1/1988 Bleidorn et al.
4,738,253 A 4/1988 Buechel et al.
4,759,350 A 7/1988 Dunn et al.
4,823,807 A 4/1989 Russell et al.
4,938,762 A 7/1990 Wehrli
4,944,760 A 7/1990 Kenna
4,945,799 A 8/1990 Knetzer
4,952,213 A 8/1990 Bowman et al.
5,002,547 A 3/1991 Poggie et al.
5,053,037 A 10/1991 Lackey
5,065,612 A 11/1991 Ooka et al.
5,067,821 A 11/1991 Young
5,116,338 A * 5/1992 Poggie .................... A61F 2/461
606/90
5,122,146 A 6/1992 Chapman et al.
5,129,908 A 7/1992 Petersen
5,141,512 A 8/1992 Farmer et al.
5,171,244 A 12/1992 Caspari et al.
5,213,112 A 5/1993 Niwa et al.
5,249,581 A 10/1993 Horbal et al.
5,251,127 A 10/1993 Raab
5,279,309 A 1/1994 Taylor et al.
5,296,855 A 3/1994 Matsuzaki et al.
5,306,276 A 4/1994 Johnson et al.
5,320,625 A 6/1994 Bertin
5,324,293 A 6/1994 Rehmann
5,325,029 A 6/1994 Janecke et al.
5,329,933 A 7/1994 Graf
5,342,367 A 8/1994 Ferrante et al.
5,343,391 A 8/1994 Mushabac
5,358,526 A 10/1994 Tornier
5,374,275 A 12/1994 Bradley et al.
5,376,093 A 12/1994 Newman
5,395,377 A 3/1995 Petersen et al.
5,417,694 A 5/1995 Marik et al.
5,423,827 A 6/1995 Mumme
5,431,653 A 7/1995 Callaway
5,458,645 A 10/1995 Bertin
5,462,548 A 10/1995 Pappas et al.
5,468,244 A 11/1995 Attfield et al.
5,470,354 A 11/1995 Hershberger et al.
5,474,088 A 12/1995 Zaharkin et al.
5,486,177 A 1/1996 Mumme et al.
5,490,854 A 2/1996 Fisher et al.
5,514,143 A 5/1996 Bonutti et al.
5,529,070 A 6/1996 Augustine et al.
5,540,693 A 7/1996 Fisher
5,540,696 A 7/1996 Booth, Jr. et al.
5,540,697 A 7/1996 Rehmann et al.
5,553,198 A 9/1996 Wang et al.
5,576,727 A 11/1996 Rosenberg et al.
5,584,837 A 12/1996 Peterson
5,597,379 A 1/1997 Haines et al.
5,611,353 A 3/1997 Dance et al.
5,624,444 A 4/1997 Wixson et al.
5,628,750 A 5/1997 Whitlock et al.
5,645,077 A 7/1997 Foxlin
5,653,764 A 8/1997 Murphy
5,681,316 A 10/1997 DeOrio et al.
5,683,398 A 11/1997 Carls et al.
5,688,282 A 11/1997 Baron et al.
5,720,752 A 2/1998 Elliot et al.
5,724,264 A 3/1998 Rosenberg et al.
5,733,292 A 3/1998 Gustilo et al.
5,748,767 A 5/1998 Raab
5,769,861 A 6/1998 Vilsmeier
5,776,137 A 7/1998 Katz
5,788,700 A 8/1998 Morawa et al.
5,817,097 A 10/1998 Howard et al.
5,824,085 A 10/1998 Sahay et al.
5,840,047 A 11/1998 Stedham
5,880,714 A 3/1999 Rosenberg et al.
5,916,219 A 6/1999 Matsuno et al.
5,919,149 A 7/1999 Allum
5,935,086 A 8/1999 Beacon et al.
5,976,156 A 11/1999 Taylor et al.
6,022,377 A 2/2000 Nuelle et al.
6,027,507 A 2/2000 Anderson et al.
6,036,696 A 3/2000 Lambrecht et al.
6,056,756 A 5/2000 Eng et al.
6,063,124 A 5/2000 Amstutz
6,090,114 A 7/2000 Matsuno et al.
6,094,019 A 7/2000 Saiki
6,096,043 A 8/2000 Techiera et al.
6,120,509 A 9/2000 Wheeler
6,122,538 A 9/2000 Sliwa, Jr. et al.
6,126,608 A 10/2000 Kemme et al.
6,162,191 A 12/2000 Foxin
6,167,292 A 12/2000 Badano et al.
6,171,310 B1 1/2001 Giordano
6,195,615 B1 2/2001 Lysen
6,197,032 B1 3/2001 Lawes et al.
6,214,013 B1 4/2001 Lambrech et al.
6,214,014 B1 4/2001 McGann
6,216,029 B1 4/2001 Paltieli
6,246,898 B1 6/2001 Vesely et al.
6,258,095 B1 7/2001 Lombardo et al.
6,261,247 B1 7/2001 Ishikawa et al.
6,299,646 B1 10/2001 Chambat et al.
6,332,089 B1 12/2001 Acker
6,348,058 B1 2/2002 Melken et al.
6,354,011 B1 3/2002 Albrecht
6,361,506 B1 3/2002 Saenger et al.
6,361,507 B1 3/2002 Foxlin
6,361,508 B1 3/2002 Johnson et al.
6,377,839 B1 4/2002 Kalfas et al.
6,381,485 B1 4/2002 Hunter et al.
6,383,149 B1 5/2002 DeMayo
6,395,005 B1 5/2002 Lovell
6,447,448 B1 9/2002 Ishikawa et al.
6,468,280 B1 10/2002 Saenger et al.
6,470,207 B1 10/2002 Simon et al.
6,471,637 B1 10/2002 Green et al.
6,473,635 B1 10/2002 Rasche
6,477,400 B1 11/2002 Barrick
6,477,421 B1 11/2002 Andersen et al.
6,478,799 B1 11/2002 Williamson
6,488,713 B1 12/2002 Hershnerger
6,499,488 B1 12/2002 Hunter et al.
6,514,259 B2 2/2003 Picard et al.
6,527,443 B1 3/2003 Vilsmeier
6,551,325 B2 4/2003 Neubauer et al.

(56) References Cited

U.S. PATENT DOCUMENTS 6,585,666 B2 7/2003 Suh et al.
6,595,997 B2 7/2003 Axelson, Jr. et al.
6,595,999 B2 7/2003 Marchione et al.
6,607,487 B2 8/2003 Chang et al.
6,640,128 B2 10/2003 Vilsmeier et al.
6,648,896 B2 11/2003 Overes et al.
6,679,916 B1 1/2004 Frankie et al.
6,685,655 B2 2/2004 DeMayo
6,685,711 B2 2/2004 Axelson et al.
6,711,431 B2 3/2004 Sarin et al.
6,712,824 B2 3/2004 Millard et al.
6,715,213 B2 4/2004 Richter
6,725,080 B2 4/2004 Melkent et al.
6,725,173 B2 4/2004 An
6,743,235 B2 6/2004 Rao
6,770,078 B2 8/2004 Bonutti
6,786,877 B2 9/2004 Foxlin
6,802,864 B2 10/2004 Tornier
6,817,470 B1 11/2004 Goldberg
6,820,025 B2 11/2004 Bachmann et al.
6,827,723 B2 12/2004 Carson
6,917,827 B2 7/2005 Kienzle, III
6,923,817 B2 8/2005 Carson et al.
6,928,742 B2 8/2005 Broers et al.
6,947,783 B2 9/2005 Immerz
6,986,181 B2 1/2006 Murphy et al.
6,997,882 B1 2/2006 Parker et al.
7,007,699 B2 3/2006 Martinelli et al.
7,021,140 B2 4/2006 Perkins
7,027,477 B2 4/2006 Sutter et al.
7,037,310 B2 5/2006 Murphy
7,048,741 B2 5/2006 Swanson
7,089,148 B1 8/2006 Bachmann et al.
7,094,241 B2 8/2006 Hodorek et al.
7,104,998 B2 9/2006 Yoon et al.
7,105,028 B2 9/2006 Murphy
7,194,295 B2 3/2007 Vilsmeier
7,209,776 B2 4/2007 Leitner
7,219,033 B2 5/2007 Kolen
7,273,500 B2 9/2007 Williamson
7,311,441 B2 12/2007 Weaver et al.
7,331,932 B2 2/2008 Leitner
7,344,541 B2 3/2008 Haines et al.
7,392,076 B2 6/2008 Moctezuma de la Barrera
7,396,357 B2 7/2008 Tornier et al.
7,412,897 B2 8/2008 Crottet et al.
7,442,196 B2 10/2008 Fisher et al.
7,444,178 B2 10/2008 Goldbach
7,468,075 B2 12/2008 Lang et al.
7,468,077 B2 12/2008 Rochetin
7,497,029 B2 3/2009 Plassky et al.
7,520,880 B2 4/2009 Claypool et al.
7,547,307 B2 6/2009 Carson et al.
7,559,931 B2 7/2009 Stone
7,575,602 B2 8/2009 Amirouche et al.
7,578,821 B2 8/2009 Fisher et al.
7,591,854 B2 9/2009 Wasielewski
7,594,933 B2 9/2009 Kammerzell et al.
7,611,520 B2 11/2009 Broers et al.
7,611,522 B2 11/2009 Gorek
7,615,005 B2 11/2009 Stefanchik et al.
7,621,920 B2 11/2009 Claypool et al.
7,623,902 B2 11/2009 Pacheco
7,632,283 B2 12/2009 Heldreth
7,726,564 B2 6/2010 Goldbach
7,776,098 B2 8/2010 Murphy
7,815,644 B2 * 10/2010 Masini .................. A61B 90/36 606/88
7,831,292 B2 11/2010 Quaid et al.
7,834,847 B2 11/2010 Boillot et al.
7,837,691 B2 11/2010 Cordes et al.
7,840,256 B2 11/2010 Lakin et al.
D629,900 S 12/2010 Fisher
7,846,092 B2 12/2010 Murphy
7,857,821 B2 12/2010 Couture et al.
7,885,705 B2 2/2011 Murphy
7,918,887 B2 4/2011 Roche
7,927,336 B2 4/2011 Rasmussen
7,970,174 B2 6/2011 Goldbach
8,000,926 B2 8/2011 Roche et al.
8,057,479 B2 11/2011 Stone
8,057,482 B2 11/2011 Stone
8,078,254 B2 12/2011 Murphy
8,098,544 B2 1/2012 Roche et al.
8,099,168 B2 1/2012 Roche et al.
8,104,960 B2 1/2012 Gill et al.
8,109,942 B2 2/2012 Carson
8,118,815 B2 * 2/2012 van der Walt ......... A61B 17/56 606/88
8,146,422 B2 4/2012 Stein
8,197,549 B2 6/2012 Amirouche et al.
8,211,041 B2 7/2012 Fisher et al.
8,241,296 B2 8/2012 Wasielewski
8,257,360 B2 9/2012 Richard et al.
8,265,790 B2 9/2012 Amiot et al.
8,267,938 B2 9/2012 Murphy
8,277,455 B2 10/2012 Couture et al.
8,282,646 B2 10/2012 Schoenefeld et al.
8,282,685 B2 10/2012 Rochetin et al.
8,317,797 B2 11/2012 Rasmussen
8,337,428 B2 12/2012 Stein et al.
8,355,773 B2 1/2013 Leitner et al.
8,394,104 B2 3/2013 Disilvestro
8,412,308 B2 4/2013 Goldbach
8,421,642 B1 4/2013 McIntosh et al.
8,421,854 B2 4/2013 Zerkin
8,427,176 B2 4/2013 Stein
8,446,473 B2 5/2013 Goldbach
8,490,488 B2 7/2013 Stein et al.
8,491,589 B2 7/2013 Fisher et al.
8,506,571 B2 8/2013 Chana
8,512,346 B2 8/2013 Couture
8,516,884 B2 8/2013 Stein et al.
8,516,907 B2 8/2013 Stein et al.
8,539,830 B2 9/2013 Stein
8,551,023 B2 10/2013 Sherman et al.
8,551,108 B2 10/2013 Pelletier et al.
8,556,830 B2 10/2013 Sherman et al.
8,556,972 B2 10/2013 Gordon et al.
8,588,892 B2 11/2013 Hladio et al.
8,661,893 B2 3/2014 Stein et al.
8,668,646 B2 3/2014 Stein et al.
8,679,186 B2 3/2014 Stein et al.
8,690,888 B2 4/2014 Stein et al.
8,696,756 B2 4/2014 Stein et al.
8,701,484 B2 4/2014 Stein et al.
8,707,782 B2 4/2014 Stein et al.
8,714,009 B2 5/2014 Stein et al.
8,715,290 B2 5/2014 Fisher et al.
8,718,820 B2 5/2014 Amiot et al.
8,720,270 B2 5/2014 Stein et al.
8,721,568 B2 5/2014 Rock et al.
8,734,432 B2 5/2014 Tuma et al.
8,734,454 B2 5/2014 Disilvestro
8,746,062 B2 6/2014 Stein et al.
8,758,355 B2 6/2014 Fisher et al.
8,764,758 B2 7/2014 Echeverri
8,777,877 B2 7/2014 Stein et al.
8,784,339 B2 7/2014 Stein et al.
8,814,810 B2 8/2014 Roche et al.
8,826,733 B2 9/2014 Stein et al.
8,828,013 B2 9/2014 Fisher et al.
8,864,686 B2 10/2014 Roche et al.
8,867,198 B2 10/2014 Steele
8,876,831 B2 11/2014 Rasmussen
8,888,786 B2 11/2014 Stone
8,906,027 B2 12/2014 Roche
8,906,107 B2 12/2014 Bojarski et al.
8,911,447 B2 12/2014 van der Walt et al.
8,911,448 B2 12/2014 Stein
8,926,530 B2 1/2015 Stein et al.
8,926,706 B2 1/2015 Bojarski et al.
8,939,030 B2 1/2015 Stein et al.
8,945,133 B2 2/2015 Stein et al.

(56) References Cited

U.S. PATENT DOCUMENTS

| | | | |
|---|---|---|---|
| 8,974,467 | B2 | 3/2015 | Stone |
| 8,974,468 | B2 | 3/2015 | Borja |
| 8,974,539 | B2 | 3/2015 | Bojarski et al. |
| 8,979,758 | B2 | 3/2015 | Stein et al. |
| 8,998,910 | B2 | 4/2015 | Borja et al. |
| 9,005,207 | B2 | 4/2015 | Dodds et al. |
| 9,011,448 | B2 | 4/2015 | Roche et al. |
| 9,044,218 | B2 | 6/2015 | Young |
| 9,095,275 | B2 | 8/2015 | Clark |
| 9,095,352 | B2 | 8/2015 | Fisher et al. |
| 9,138,319 | B2 | 9/2015 | Fanson et al. |
| 9,141,254 | B2 | 9/2015 | Boillot et al. |
| 9,161,717 | B2 | 10/2015 | Stein et al. |
| 9,168,032 | B2 | 10/2015 | Hutchison et al. |
| 9,189,083 | B2 | 11/2015 | Roche et al. |
| 9,192,392 | B2 | 11/2015 | van der Walt et al. |
| 9,199,733 | B2 | 12/2015 | Keennon et al. |
| 9,226,694 | B2 | 1/2016 | Stein et al. |
| 9,232,951 | B2 | 1/2016 | Johannaber |
| 9,237,885 | B2 | 1/2016 | Stein et al. |
| 9,259,172 | B2 | 2/2016 | Stein et al. |
| 9,259,179 | B2 | 2/2016 | Stein |
| 9,262,802 | B2 | 2/2016 | Aghazadeh |
| 9,265,447 | B2 | 2/2016 | Stein et al. |
| 9,271,675 | B2 | 3/2016 | Stein et al. |
| 9,271,756 | B2 * | 3/2016 | van der Walt ......... A61B 34/10 |
| 9,289,163 | B2 | 3/2016 | Stein et al. |
| 9,332,943 | B2 | 5/2016 | Stein et al. |
| 9,339,212 | B2 | 5/2016 | Stein et al. |
| 9,339,226 | B2 | 5/2016 | van der Walt et al. |
| 9,345,449 | B2 | 5/2016 | Stein et al. |
| 9,345,492 | B2 | 5/2016 | Stein et al. |
| 9,351,782 | B2 | 5/2016 | Stein et al. |
| 9,358,136 | B2 | 6/2016 | Stein et al. |
| 9,375,178 | B2 | 6/2016 | Aghazadeh |
| 9,456,769 | B2 | 10/2016 | Stein et al. |
| 9,549,742 | B2 | 1/2017 | Berend et al. |
| 9,572,586 | B2 | 2/2017 | van der Walt et al. |
| 9,642,572 | B2 | 5/2017 | Mahfouz et al. |
| 9,649,160 | B2 | 5/2017 | van der Walt et al. |
| 9,775,725 | B2 | 10/2017 | van der Walt et al. |
| 9,855,075 | B2 | 1/2018 | van der Walt et al. |
| 9,930,946 | B2 | 4/2018 | Zondervan |
| 9,931,059 | B2 | 4/2018 | Borja |
| 10,206,714 | B2 | 2/2019 | van der Walt et al. |
| 10,238,510 | B2 | 3/2019 | van der Walt et al. |
| 10,321,852 | B2 | 6/2019 | Borja |
| 10,363,149 | B2 | 7/2019 | van der Walt et al. |
| 10,597,178 | B2 | 3/2020 | Ryterski et al. |
| 10,603,115 | B2 | 3/2020 | van der Walt et al. |
| 10,716,580 | B2 | 7/2020 | Berend et al. |
| 10,863,995 | B2 | 12/2020 | Nielsen et al. |
| 10,864,019 | B2 | 12/2020 | van der Walt et al. |
| 10,869,771 | B2 | 12/2020 | van der Walt et al. |
| 10,918,499 | B2 | 2/2021 | Nielsen et al. |
| 11,020,245 | B2 | 6/2021 | van der Walt et al. |
| 11,179,062 | B2 | 11/2021 | Borja et al. |
| 11,179,167 | B2 | 11/2021 | Stone |
| 11,191,334 | B2 | 12/2021 | Aghazadeh et al. |
| 11,273,232 | B2 | 3/2022 | Placik |
| 11,540,746 | B2 | 1/2023 | Borja et al. |
| 11,547,451 | B2 | 1/2023 | van der Walt et al. |
| 11,547,580 | B2 | 1/2023 | Nielsen et al. |
| 11,633,293 | B2 | 4/2023 | van der Walt et al. |
| 11,653,981 | B2 | 5/2023 | van der Walt et al. |
| 11,684,392 | B2 | 6/2023 | van der Walt et al. |
| 11,786,261 | B2 | 10/2023 | Nielsen et al. |
| 11,871,965 | B2 | 1/2024 | van der Walt et al. |
| 11,903,597 | B2 | 2/2024 | Stone |
| 11,911,119 | B2 | 2/2024 | van der Walt et al. |
| 12,127,801 | B2 | 10/2024 | Walter et al. |
| 12,144,567 | B2 | 11/2024 | van der Walt et al. |
| 12,232,863 | B2 | 2/2025 | Borja et al. |
| 12,239,344 | B2 | 3/2025 | van der Walt et al. |
| 12,318,313 | B2 | 6/2025 | van der Walt et al. |
| 12,376,972 | B2 | 8/2025 | van der Walt et al. |
| 12,433,694 | B2 | 10/2025 | van der Walt et al. |
| 12,446,926 | B2 | 10/2025 | van der Walt et al. |
| 2002/0077540 | A1 | 6/2002 | Kienzie, III |
| 2002/0103610 | A1 | 8/2002 | Bachmann et al. |
| 2002/0107522 | A1 | 8/2002 | Picard et al. |
| 2002/0133175 | A1 | 9/2002 | Carson |
| 2002/0198451 | A1 | 12/2002 | Carson |
| 2003/0019294 | A1 | 1/2003 | Richter |
| 2003/0069591 | A1 | 4/2003 | Carson et al. |
| 2003/0093080 | A1 | 5/2003 | Brown et al. |
| 2003/0105470 | A1 | 6/2003 | White |
| 2003/0120282 | A1 | 6/2003 | Scouten et al. |
| 2003/0153978 | A1 | 8/2003 | Whiteside |
| 2003/0163142 | A1 | 8/2003 | Paltieli et al. |
| 2003/0181919 | A1 | 9/2003 | Gorek |
| 2003/0184297 | A1 | 10/2003 | Jakab |
| 2003/0199882 | A1 | 10/2003 | Gorek |
| 2003/0204965 | A1 | 11/2003 | Hennessey |
| 2003/0229356 | A1 | 12/2003 | Dye |
| 2004/0006393 | A1 | 1/2004 | Burkinshaw |
| 2004/0019382 | A1 | 1/2004 | Amirouche et al. |
| 2004/0034313 | A1 | 2/2004 | Leitner |
| 2004/0039396 | A1 | 2/2004 | Couture et al. |
| 2004/0068260 | A1 | 4/2004 | Cossette et al. |
| 2004/0073225 | A1 | 4/2004 | Subba Rao |
| 2004/0087958 | A1 | 5/2004 | Myers et al. |
| 2004/0087962 | A1 | 5/2004 | Gorek |
| 2004/0097952 | A1 | 5/2004 | Sarin et al. |
| 2004/0102792 | A1 | 5/2004 | Sarin et al. |
| 2004/0106916 | A1 | 6/2004 | Quaid et al. |
| 2004/0122441 | A1 * | 6/2004 | Muratsu ............ A61B 17/0206 606/102 |
| 2004/0147926 | A1 | 7/2004 | Iversen |
| 2004/0149036 | A1 | 8/2004 | Foxlin et al. |
| 2004/0152955 | A1 | 8/2004 | McGinley et al. |
| 2004/0152970 | A1 | 8/2004 | Hunter et al. |
| 2004/0153066 | A1 | 8/2004 | Coon et al. |
| 2004/0153079 | A1 | 8/2004 | Tsougarakis et al. |
| 2004/0181144 | A1 | 9/2004 | Cinquin et al. |
| 2004/0201857 | A1 | 10/2004 | Foxlin |
| 2004/0230197 | A1 | 11/2004 | Tornier et al. |
| 2004/0243148 | A1 | 12/2004 | Wasielewski |
| 2005/0021037 | A1 | 1/2005 | McCombs et al. |
| 2005/0021044 | A1 | 1/2005 | Stone et al. |
| 2005/0038442 | A1 | 2/2005 | Freeman |
| 2005/0070864 | A1 | 3/2005 | Fellion |
| 2005/0107799 | A1 | 5/2005 | Graf et al. |
| 2005/0113846 | A1 | 5/2005 | Carson |
| 2005/0149040 | A1 | 7/2005 | Haines et al. |
| 2005/0149054 | A1 | 7/2005 | Gorek |
| 2005/0197814 | A1 | 9/2005 | Aram et al. |
| 2005/0209605 | A1 | 9/2005 | Grimm et al. |
| 2005/0222574 | A1 | 10/2005 | Giordano et al. |
| 2005/0234332 | A1 | 10/2005 | Murphy |
| 2005/0251026 | A1 | 11/2005 | Stone |
| 2005/0251148 | A1 | 11/2005 | Friedrich |
| 2006/0009780 | A1 | 1/2006 | Foley et al. |
| 2006/0015018 | A1 | 1/2006 | Jutras et al. |
| 2006/0015120 | A1 | 1/2006 | Richard et al. |
| 2006/0020177 | A1 | 1/2006 | Seo et al. |
| 2006/0064105 | A1 | 3/2006 | Raistrick et al. |
| 2006/0084977 | A1 | 4/2006 | Lieberman |
| 2006/0089657 | A1 | 4/2006 | Broers et al. |
| 2006/0094958 | A1 | 5/2006 | Marquart et al. |
| 2006/0122491 | A1 | 6/2006 | Murray et al. |
| 2006/0142656 | A1 | 6/2006 | Malackowski et al. |
| 2006/0142657 | A1 | 6/2006 | Quaid et al. |
| 2006/0149276 | A1 * | 7/2006 | Grimm ............. A61B 17/1764 606/88 |
| 2006/0161051 | A1 | 7/2006 | Terrill-Grisoni et al. |
| 2006/0184177 | A1 | 8/2006 | Echeverri |
| 2006/0217733 | A1 | 9/2006 | Plassky et al. |
| 2006/0217734 | A1 | 9/2006 | Sanford et al. |
| 2006/0241639 | A1 | 10/2006 | Kuczynski et al. |
| 2006/0270949 | A1 | 11/2006 | Mathie et al. |
| 2006/0282023 | A1 | 12/2006 | Leitner |
| 2007/0016009 | A1 | 1/2007 | Lakin et al. |
| 2007/0032748 | A1 | 2/2007 | McNeil et al. |

(56) References Cited

U.S. PATENT DOCUMENTS

2007/0043287 A1 2/2007 Degraaf
2007/0043375 A1 2/2007 Anissian
2007/0066917 A1 3/2007 Hodorek et al.
2007/0073296 A1 3/2007 Panchbhavi
2007/0100346 A1 5/2007 Wyss et al.
2007/0118139 A1 5/2007 Cuellar et al.
2007/0162142 A1 7/2007 Stone
2007/0179626 A1 8/2007 de la Barrera et al.
2007/0179628 A1 8/2007 Rochetin
2007/0219559 A1 9/2007 Heavener et al.
2007/0219561 A1 9/2007 Lavallee et al.
2007/0226986 A1 10/2007 Park et al.
2007/0244488 A1* 10/2007 Metzger ............... A61B 17/025 606/90
2007/0249967 A1 10/2007 Buly et al.
2007/0270718 A1 11/2007 Rochetin et al.
2007/0270973 A1 11/2007 Johnson et al.
2007/0287911 A1 12/2007 Haid et al.
2007/0293869 A1 12/2007 Conte et al.
2008/0039868 A1 2/2008 Tuemmler et al.
2008/0058945 A1 3/2008 Hajaj et al.
2008/0071195 A1 3/2008 Cuellar et al.
2008/0103509 A1 5/2008 Goldbach
2008/0108912 A1 5/2008 Node-Langlois
2008/0162074 A1 7/2008 Schneider
2008/0183179 A1 7/2008 Siebel et al.
2008/0195109 A1 8/2008 Hunter et al.
2008/0202200 A1 8/2008 West
2008/0211768 A1 9/2008 Breen et al.
2008/0243127 A1 10/2008 Lang et al.
2008/0249394 A1 10/2008 Giori et al.
2008/0262812 A1 10/2008 Arata et al.
2008/0275451 A1 11/2008 McAllister et al.
2008/0281328 A1 11/2008 Lang et al.
2008/0285805 A1 11/2008 Luinge et al.
2009/0000626 A1 1/2009 Quaid et al.
2009/0000627 A1 1/2009 Quaid et al.
2009/0012532 A1 1/2009 Quaid et al.
2009/0018544 A1 1/2009 Heavener
2009/0040224 A1 2/2009 Igarashi et al.
2009/0070038 A1 3/2009 Geelen et al.
2009/0076507 A1 3/2009 Claypool et al.
2009/0076519 A1 3/2009 Iversen
2009/0088753 A1 4/2009 Aram et al.
2009/0099665 A1 4/2009 Taylor et al.
2009/0138019 A1 5/2009 Wasielewski
2009/0171370 A1 7/2009 Yoon et al.
2009/0209884 A1 8/2009 Van Vorhis et al.
2009/0216247 A1 8/2009 Collette
2009/0216285 A1 8/2009 Ek
2009/0234360 A1 9/2009 Alexander
2009/0247863 A1 10/2009 Proulx et al.
2009/0248044 A1 10/2009 Amiot et al.
2009/0264737 A1 10/2009 Haechler et al.
2009/0270864 A1 10/2009 Poncet
2009/0270865 A1 10/2009 Poncet et al.
2009/0270868 A1 10/2009 Park et al.
2009/0270869 A1 10/2009 Colquhoun et al.
2009/0270874 A1 10/2009 Santarella et al.
2009/0270875 A1 10/2009 Poncet
2009/0270928 A1 10/2009 Stone et al.
2009/0276054 A1 11/2009 Clifford et al.
2009/0281545 A1 11/2009 Stubbs
2009/0289806 A1 11/2009 Thornberry
2009/0292227 A1 11/2009 Scholten et al.
2009/0299416 A1 12/2009 Haenni et al.
2009/0299483 A1 12/2009 Amirouche et al.
2009/0306679 A1 12/2009 Murphy
2009/0312973 A1 12/2009 Hatlestad et al.
2009/0318836 A1 12/2009 Stone et al.
2009/0318930 A1 12/2009 Stone et al.
2009/0318931 A1 12/2009 Stone et al.
2009/0324078 A1 12/2009 Wu et al.
2010/0010506 A1 1/2010 Murphy
2010/0016705 A1 1/2010 Stone
2010/0023018 A1 1/2010 Theofilos
2010/0063508 A1* 3/2010 Borja ..................... A61B 34/25 606/88
2010/0063509 A1 3/2010 Borja et al.
2010/0064216 A1 3/2010 Borja et al.
2010/0069911 A1 3/2010 Borja et al.
2010/0076505 A1 3/2010 Borja
2010/0087829 A1 4/2010 Metzger et al.
2010/0100011 A1 4/2010 Roche
2010/0100154 A1 4/2010 Roche
2010/0113980 A1 5/2010 Herr et al.
2010/0121334 A1 5/2010 Couture et al.
2010/0137869 A1 6/2010 Borja et al.
2010/0137871 A1 6/2010 Borja
2010/0153081 A1 6/2010 Bellettre et al.
2010/0179605 A1 7/2010 Branch et al.
2010/0182914 A1 7/2010 DelRegno et al.
2010/0192662 A1 8/2010 Yanni
2010/0198067 A1 8/2010 Mahfouz et al.
2010/0198275 A1* 8/2010 Chana .................. A61B 17/025 606/86 R
2010/0204551 A1 8/2010 Roche
2010/0204575 A1 8/2010 Roche et al.
2010/0204955 A1 8/2010 Roche et al.
2010/0211077 A1 8/2010 Couture et al.
2010/0239996 A1 9/2010 Ertl
2010/0241126 A1* 9/2010 Ghijselings .......... A61B 17/155 606/88
2010/0249533 A1 9/2010 Pierce et al.
2010/0249534 A1 9/2010 Pierce et al.
2010/0249535 A1 9/2010 Pierce et al.
2010/0249659 A1 9/2010 Sherman et al.
2010/0249665 A1 9/2010 Roche
2010/0249787 A1 9/2010 Roche
2010/0249788 A1 9/2010 Roche
2010/0249790 A1 9/2010 Roche
2010/0249791 A1 9/2010 Roche
2010/0250276 A1 9/2010 Pierce et al.
2010/0250284 A1 9/2010 Roche et al.
2010/0250571 A1 9/2010 Pierce et al.
2010/0256504 A1 10/2010 Moreau-Gaudry et al.
2010/0261998 A1 10/2010 Stiehl
2010/0268067 A1 10/2010 Razzaque et al.
2010/0298661 A1 11/2010 McCombie et al.
2010/0324457 A1 12/2010 Bean et al.
2010/0326187 A1 12/2010 Stein
2010/0326194 A1 12/2010 Stein et al.
2010/0326210 A1 12/2010 Stein et al.
2010/0326211 A1 12/2010 Stein
2010/0327848 A1 12/2010 Stein
2010/0327880 A1 12/2010 Stein
2010/0328077 A1 12/2010 Stein
2010/0328098 A1 12/2010 Stein et al.
2010/0331633 A1 12/2010 Stein
2010/0331663 A1 12/2010 Stein
2010/0331679 A1 12/2010 Stein
2010/0331680 A1 12/2010 Stein
2010/0331681 A1 12/2010 Stein et al.
2010/0331682 A1 12/2010 Stein et al.
2010/0331683 A1 12/2010 Stein et al.
2010/0331685 A1 12/2010 Stein et al.
2010/0331687 A1 12/2010 Stein et al.
2010/0331704 A1 12/2010 Stein et al.
2010/0331718 A1 12/2010 Stein
2010/0331733 A1 12/2010 Stein
2010/0331734 A1 12/2010 Stein
2010/0331735 A1 12/2010 Stein
2010/0331736 A1 12/2010 Stein
2010/0331737 A1 12/2010 Stein et al.
2010/0331738 A1 12/2010 Stein et al.
2010/0331894 A1 12/2010 Stein
2010/0332152 A1 12/2010 Stein
2011/0028865 A1 2/2011 Luinge et al.
2011/0032184 A1 2/2011 Roche et al.
2011/0093081 A1 4/2011 Chana et al.
2011/0160572 A1 6/2011 McIntosh et al.
2011/0160616 A1 6/2011 Stein et al.
2011/0160738 A1 6/2011 McIntosh et al.

(56) References Cited

U.S. PATENT DOCUMENTS

| | | | |
|---|---|---|---|
| 2011/0208093 | A1* | 8/2011 | Gross .................... A61B 90/10 600/587 |
| 2011/0213275 | A1 | 9/2011 | Boos et al. |
| 2011/0218458 | A1 | 9/2011 | Valin et al. |
| 2011/0218543 | A1 | 9/2011 | van der Walt |
| 2011/0218546 | A1 | 9/2011 | De La Fuente Klein et al. |
| 2011/0275957 | A1 | 11/2011 | Bhandari |
| 2012/0022406 | A1 | 1/2012 | Hladio et al. |
| 2012/0029389 | A1 | 2/2012 | Amiot et al. |
| 2012/0053488 | A1 | 3/2012 | Boutin et al. |
| 2012/0053594 | A1 | 3/2012 | Pelletier et al. |
| 2012/0093377 | A1 | 4/2012 | Tsougarakis et al. |
| 2012/0110810 | A1 | 5/2012 | Houser et al. |
| 2012/0130279 | A1 | 5/2012 | Stone |
| 2012/0157887 | A1 | 6/2012 | Fanson et al. |
| 2012/0172712 | A1 | 7/2012 | Bar-Tal |
| 2012/0172762 | A1 | 7/2012 | Boyer et al. |
| 2012/0172884 | A1 | 7/2012 | Zheng et al. |
| 2012/0203140 | A1 | 8/2012 | Malchau et al. |
| 2012/0209117 | A1 | 8/2012 | Mozes et al. |
| 2012/0232429 | A1 | 9/2012 | Fischer et al. |
| 2012/0239555 | A1 | 9/2012 | Seethaler et al. |
| 2012/0283599 | A1 | 11/2012 | Borja |
| 2012/0290088 | A1 | 11/2012 | Amirouche et al. |
| 2012/0316567 | A1 | 12/2012 | Gross et al. |
| 2012/0330367 | A1 | 12/2012 | Roche et al. |
| 2013/0023794 | A1 | 1/2013 | Stein et al. |
| 2013/0023795 | A1 | 1/2013 | Stein et al. |
| 2013/0046310 | A1 | 2/2013 | Ranawat et al. |
| 2013/0053859 | A1 | 2/2013 | Penenberg |
| 2013/0064478 | A1 | 3/2013 | Sold et al. |
| 2013/0066323 | A1 | 3/2013 | Nycz et al. |
| 2013/0079668 | A1 | 3/2013 | Stein et al. |
| 2013/0079669 | A1 | 3/2013 | Stein et al. |
| 2013/0079670 | A1 | 3/2013 | Stein et al. |
| 2013/0079671 | A1 | 3/2013 | Stein et al. |
| 2013/0079675 | A1 | 3/2013 | Stein et al. |
| 2013/0079678 | A1 | 3/2013 | Stein et al. |
| 2013/0079679 | A1 | 3/2013 | Roche et al. |
| 2013/0079680 | A1 | 3/2013 | Stein et al. |
| 2013/0079790 | A1 | 3/2013 | Stein et al. |
| 2013/0079791 | A1 | 3/2013 | Stein et al. |
| 2013/0079793 | A1 | 3/2013 | Stein et al. |
| 2013/0079884 | A1 | 3/2013 | Stein et al. |
| 2013/0096567 | A1 | 4/2013 | Fisher et al. |
| 2013/0102929 | A1 | 4/2013 | Haight et al. |
| 2013/0103038 | A1 | 4/2013 | Fischer et al. |
| 2013/0110250 | A1 | 5/2013 | Li |
| 2013/0190887 | A1 | 7/2013 | Fanson et al. |
| 2013/0203031 | A1 | 8/2013 | McKinnon et al. |
| 2013/0226034 | A1 | 8/2013 | Stein et al. |
| 2013/0226035 | A1 | 8/2013 | Stein et al. |
| 2013/0226036 | A1 | 8/2013 | Stein et al. |
| 2013/0226190 | A1 | 8/2013 | McKinnon et al. |
| 2013/0261758 | A1 | 10/2013 | Claypool et al. |
| 2013/0274633 | A1 | 10/2013 | Hladio et al. |
| 2013/0296860 | A1 | 11/2013 | Chana et al. |
| 2013/0331850 | A1 | 12/2013 | Bojarski et al. |
| 2014/0005531 | A1 | 1/2014 | Taylor |
| 2014/0005673 | A1 | 1/2014 | Pelletier et al. |
| 2014/0018707 | A1 | 1/2014 | Sherman et al. |
| 2014/0031672 | A1 | 1/2014 | McCaulley et al. |
| 2014/0052149 | A1* | 2/2014 | van der Walt ........ A61F 2/4657 606/130 |
| 2014/0094715 | A1 | 4/2014 | Stein et al. |
| 2014/0107796 | A1 | 4/2014 | Stein et al. |
| 2014/0114179 | A1 | 4/2014 | Muller et al. |
| 2014/0134586 | A1 | 5/2014 | Stein et al. |
| 2014/0135624 | A1 | 5/2014 | Stein et al. |
| 2014/0135655 | A1 | 5/2014 | Stein et al. |
| 2014/0135658 | A1 | 5/2014 | Hladio et al. |
| 2014/0135744 | A1 | 5/2014 | Stein et al. |
| 2014/0135773 | A1 | 5/2014 | Stein et al. |
| 2014/0136143 | A1 | 5/2014 | Stein et al. |
| 2014/0148676 | A1 | 5/2014 | Stein et al. |
| 2014/0165796 | A1 | 6/2014 | Gauthier et al. |
| 2014/0171754 | A1 | 6/2014 | Stein et al. |
| 2014/0182062 | A1 | 7/2014 | Aghazadeh |
| 2014/0222007 | A1 | 8/2014 | Rock et al. |
| 2014/0224685 | A1 | 8/2014 | Carnevali |
| 2014/0228851 | A1 | 8/2014 | Guloy, Jr. et al. |
| 2014/0268516 | A1 | 9/2014 | Fathollahi et al. |
| 2014/0270583 | A1 | 9/2014 | Anderson |
| 2014/0275940 | A1 | 9/2014 | Hladio et al. |
| 2014/0276000 | A1 | 9/2014 | Mullaney et al. |
| 2014/0276240 | A1 | 9/2014 | Stein et al. |
| 2014/0276241 | A1 | 9/2014 | Stein et al. |
| 2014/0276860 | A1 | 9/2014 | Stein et al. |
| 2014/0276861 | A1 | 9/2014 | Stein et al. |
| 2014/0276863 | A1 | 9/2014 | Stein et al. |
| 2014/0276864 | A1 | 9/2014 | Aghazadeh |
| 2014/0276885 | A1 | 9/2014 | Stein et al. |
| 2014/0276886 | A1 | 9/2014 | Stein et al. |
| 2014/0277526 | A1 | 9/2014 | Stein et al. |
| 2014/0277542 | A1 | 9/2014 | Stein et al. |
| 2014/0288563 | A1 | 9/2014 | Claypool et al. |
| 2014/0296860 | A1 | 10/2014 | Stein et al. |
| 2014/0303631 | A1 | 10/2014 | Thornberry |
| 2014/0330105 | A1 | 11/2014 | Roche |
| 2014/0330281 | A1 | 11/2014 | Aghazadeh |
| 2014/0364858 | A1 | 12/2014 | Li et al. |
| 2015/0018718 | A1 | 1/2015 | Aghazadeh |
| 2015/0080901 | A1 | 3/2015 | Stein |
| 2015/0100058 | A1 | 4/2015 | van der Walt et al. |
| 2015/0100059 | A1 | 4/2015 | Chana et al. |
| 2015/0106024 | A1 | 4/2015 | Lightcap et al. |
| 2015/0127009 | A1 | 5/2015 | Berend et al. |
| 2015/0142372 | A1 | 5/2015 | Singh |
| 2015/0143781 | A1 | 5/2015 | Agnihotri |
| 2015/0150569 | A1 | 6/2015 | van der Walt et al. |
| 2015/0157335 | A1* | 6/2015 | Rasmussen .......... A61B 17/025 606/62 |
| 2015/0164657 | A1 | 6/2015 | Miles et al. |
| 2015/0238204 | A1 | 8/2015 | Stone |
| 2015/0245914 | A1 | 9/2015 | Langton |
| 2015/0265363 | A1 | 9/2015 | White et al. |
| 2015/0272597 | A1 | 10/2015 | Johannaber |
| 2015/0313723 | A1 | 11/2015 | Jansen |
| 2015/0313725 | A1 | 11/2015 | Fisher et al. |
| 2015/0335448 | A1 | 11/2015 | Lorio et al. |
| 2015/0342516 | A1 | 12/2015 | Nguyen et al. |
| 2016/0030156 | A1 | 2/2016 | Cole |
| 2016/0038242 | A1 | 2/2016 | Lo Iacono et al. |
| 2016/0074053 | A1 | 3/2016 | Hutchison et al. |
| 2016/0081762 | A1 | 3/2016 | Stein et al. |
| 2016/0089079 | A1 | 3/2016 | Stein |
| 2016/0166321 | A1 | 6/2016 | Amsler |
| 2016/0175055 | A1 | 6/2016 | Hook et al. |
| 2016/0206378 | A1 | 7/2016 | Flett et al. |
| 2016/0213383 | A1 | 7/2016 | van der Walt et al. |
| 2016/0220315 | A1 | 8/2016 | Falardeau |
| 2016/0220318 | A1 | 8/2016 | Falardeau et al. |
| 2016/0220385 | A1 | 8/2016 | Falardeau et al. |
| 2016/0242934 | A1* | 8/2016 | van der Walt ........ A61F 2/4684 |
| 2016/0278943 | A1 | 9/2016 | van der Walt et al. |
| 2016/0346044 | A1* | 12/2016 | Brown .................. A61B 34/20 |
| 2017/0035166 | A1 | 2/2017 | Zondervan |
| 2017/0119475 | A1 | 5/2017 | McCabe et al. |
| 2017/0238946 | A1 | 8/2017 | van der Walt et al. |
| 2017/0296203 | A1 | 10/2017 | Stone |
| 2017/0325892 | A1 | 11/2017 | Aghazadeh |
| 2017/0367766 | A1 | 12/2017 | Mahfouz |
| 2018/0028322 | A1 | 2/2018 | Sharkey et al. |
| 2018/0064496 | A1 | 3/2018 | Hladio et al. |
| 2018/0177509 | A1* | 6/2018 | Trabish ................. A61B 90/06 |
| 2018/0193171 | A1 | 7/2018 | van der Walt et al. |
| 2018/0206860 | A1 | 7/2018 | van der Walt et al. |
| 2018/0235762 | A1 | 8/2018 | Radermacher et al. |
| 2019/0350728 | A1 | 11/2019 | van der Walt et al. |
| 2019/0357809 | A1 | 11/2019 | Borja et al. |
| 2020/0352654 | A1 | 11/2020 | van der Walt et al. |
| 2020/0390501 | A1* | 12/2020 | Brown .................. A61B 90/06 |
| 2021/0153880 | A1 | 5/2021 | Nielsen et al. |
| 2021/0153908 | A1 | 5/2021 | van der Walt et al. |

(56) References Cited

U.S. PATENT DOCUMENTS

| | | | |
|---|---|---|---|
| 2021/0186711 A1 | 6/2021 | van der Walt et al. |
| 2021/0220152 A1 | 7/2021 | Nielsen et al. |
| 2021/0315716 A1 | 10/2021 | van der Walt et al. |
| 2022/0071509 A1 | 3/2022 | Borja et al. |
| 2022/0240953 A1 | 8/2022 | Stone |
| 2022/0313455 A1 | 10/2022 | van der Walt et al. |
| 2022/0378516 A1 | 12/2022 | Sierra et al. |
| 2023/0059247 A1 | 2/2023 | Gannoe |
| 2023/0135541 A1 | 5/2023 | Borja et al. |
| 2023/0149185 A1 | 5/2023 | Nielsen et al. |
| 2023/0157727 A1 | 5/2023 | van der Walt et al. |
| 2023/0248447 A1 | 8/2023 | van der Walt et al. |
| 2023/0277335 A1 | 9/2023 | van der Walt et al. |
| 2023/0301685 A1 | 9/2023 | van der Walt et al. |
| 2023/0414292 A1 | 12/2023 | Roger et al. |
| 2024/0099744 A1 | 3/2024 | van der Walt et al. |
| 2024/0197406 A1 | 6/2024 | van der Walt et al. |
| 2024/0299099 A1 | 9/2024 | Walter et al. |
| 2024/0315749 A1 | 9/2024 | Walter et al. |
| 2025/0017745 A1 | 1/2025 | van der Walt et al. |
| 2025/0082413 A1 | 3/2025 | van der Walt et al. |
| 2025/0152039 A1 | 5/2025 | Borja |
| 2025/0152204 A1 | 5/2025 | van der Walt et al. |
| 2025/0345187 A1 | 11/2025 | van der Walt et al. |
| 2025/0352361 A1 | 11/2025 | van der Walt et al. |
| 2025/0366946 A1 | 12/2025 | Olivo et al. |

FOREIGN PATENT DOCUMENTS

| | | |
|---|---|---|
| CA | 2 537 711 | 8/2007 |
| CN | 109846528 | 6/2019 |
| DE | 4 225 112 | 12/1993 |
| DE | 29704393 | 8/1997 |
| DE | 198 30 359 | 1/2000 |
| DE | 20116368 | 12/2001 |
| EP | 0 557 591 | 9/1993 |
| EP | 0 651 968 | 5/1995 |
| EP | 0 675 698 | 10/1995 |
| EP | 1 304 093 | 10/2005 |
| EP | 1 635 705 | 3/2006 |
| EP | 1 814 471 | 3/2010 |
| EP | 1 817 547 | 4/2012 |
| EP | 2 491 873 | 8/2012 |
| EP | 2 567 665 | 3/2013 |
| EP | 2 588 030 | 5/2013 |
| EP | 2 822 481 | 1/2015 |
| EP | 2 957 249 | 12/2015 |
| EP | 3 395 281 | 10/2018 |
| EP | 4 287 980 | 12/2023 |
| GB | 2 197 790 | 6/1988 |
| GB | 2 511 885 | 9/2014 |
| JP | 07-184929 | 7/1995 |
| JP | H08-240611 | 9/1996 |
| JP | 2004-237064 | 8/2004 |
| JP | 2004-529679 | 9/2004 |
| JP | 2006-314775 | 11/2006 |
| JP | 2006-528496 | 12/2006 |
| JP | 2007-503289 | 2/2007 |
| JP | 2007-534351 | 11/2007 |
| JP | 2008-521574 | 6/2008 |
| JP | 2008-537496 | 9/2008 |
| JP | 2009-511136 | 3/2009 |
| JP | 2011-502626 | 1/2011 |
| JP | 2013-000230 | 1/2013 |
| JP | 2014-524815 | 9/2014 |
| JP | 2015-524733 | 8/2015 |
| JP | 2015-226613 | 12/2015 |
| JP | 6980248 | 11/2021 |
| JP | 7180159 | 11/2022 |
| WO | WO 94/020040 | 9/1994 |
| WO | WO 94/027516 | 12/1994 |
| WO | WO 99/60939 | 12/1999 |
| WO | WO 2001/030247 | 5/2001 |
| WO | WO 02/000131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2006/078236 | 7/2006 |
| WO | WO 2006/119387 | 11/2006 |
| WO | WO 2006/136836 | 12/2006 |
| WO | WO 2007/136784 | 11/2007 |
| WO | WO 2008/073999 | 6/2008 |
| WO | WO 2008/129414 | 10/2008 |
| WO | WO 2009/117833 | 10/2009 |
| WO | WO 2010/011978 | 1/2010 |
| WO | WO 2010/030809 | 3/2010 |
| WO | WO 2010/063117 | 6/2010 |
| WO | WO 2011/044273 | 4/2011 |
| WO | WO 2012/006066 | 1/2012 |
| WO | WO 2012/006172 | 1/2012 |
| WO | WO 2012/027815 | 3/2012 |
| WO | WO 2012/027816 | 3/2012 |
| WO | WO 2012/082164 | 6/2012 |
| WO | WO 2012/109361 | 8/2012 |
| WO | WO 2012/113054 | 8/2012 |
| WO | WO 2013/012561 | 1/2013 |
| WO | WO 2013/013094 | 1/2013 |
| WO | WO 2013/044157 | 3/2013 |
| WO | WO 2013/049534 | 4/2013 |
| WO | WO 2013/044165 | 5/2013 |
| WO | WO 2013/044174 | 7/2013 |
| WO | WO 2013/169674 | 11/2013 |
| WO | WO 2013/173700 | 11/2013 |
| WO | WO 2013/188960 | 12/2013 |
| WO | WO 2014/028227 | 2/2014 |
| WO | WO 2014/063181 | 5/2014 |
| WO | WO 2014/197988 | 12/2014 |
| WO | WO 2015/038979 | 3/2015 |
| WO | WO 2015/054745 | 4/2015 |
| WO | WO 2016/070288 | 5/2016 |
| WO | WO 2016/134168 | 8/2016 |
| WO | WO 2016/147153 | 9/2016 |
| WO | WO 2016/154489 | 9/2016 |
| WO | WO 2017/093769 | 6/2017 |
| WO | WO 2018/085900 | 5/2018 |
| WO | WO 2018/119360 | 6/2018 |
| WO | WO 2018/169980 | 9/2018 |
| WO | WO 2018/169995 | 9/2018 |
| WO | WO 2019/036752 | 2/2019 |
| WO | WO 2021/119001 | 6/2021 |
| WO | WO 2021/188798 | 9/2021 |
| WO | WO 2022/165561 | 8/2022 |
| WO | WO 2024/108260 | 5/2024 |
| WO | WO 2025/250681 | 12/2025 |

OTHER PUBLICATIONS 510 (k) Summary of Safety and Effectiveness for BrainLAB knee, in 5 pages.

Anderson MD., Kevin, et al., “Computer Assisted Navigation in Total Knee Arthroplasty”, The Journal of Arthroplasty, 2005, vol. 20, No. 7, Suppl. 3, in 7 pages.

Ang, et al., An Active Hand-Held Instrument for Enhanced Microsurgical Accuracy, Medical Image Computing and Computer-Assisted Intervention, 2000, vol. 1935, pp. 878-887.

Arnold-Moore, et al., Architecture of a Content Management Server for XML Document Applications, RMIT Multimedia Database Systems, Royal Melbourne Institute of Technology, Victoria Australia, in 12 pages.

ArthroCAD, Enhancing orthopedic outcomes through optimal alignment, 2012, pp. in 2 pages.

Bae et al., “Computer Assisted Navigation in Knee Arthroplasty”, Clinics in Orthopedic Surgery, 2011, vol. 3, pp. 259-267.

Bargren, MD., et al.,, Alignment in Total Knee Arthroplasty, Correlated Biomechanical and Clinical Observations, Clinical Orthopaedics and Related Research, Mar. 1, 1983, Issue 173, pp. 178-183, Philadelphia.

Bathis, H. et al., “Alignment in total knee arthroplasty”, The Journal of Bone & Joint Surgery (Br), 2004, 86-B, pp. 682-687, British Editorial.

(56) References Cited

OTHER PUBLICATIONS

Bhandari, Design and Prototype of a Computer Assisted Surgical Navigation System for Total Knee Replacement Surgery, May 12, 2009, pp. in 294 pages.
Biomet Orthopedics, Inc, Vision Acetabular Surgical Techniques, website brochure, p. 16 pages.
Biomet Orthopedics, Inc., Universal Ringlock® Acetabular Series, vol. website brochure, p. 13 pages.
Brainlab, "Position Determination and Calibration in optical tracking systems", Florenus the technology merchants, in 2 pages.
Brainlab, "Tracking and imaging in Navigation", Florenus, in 2 pages.
Brennan, et al., Quantification of Inertial Sensor-Based 3D Joint Angle Measurement Accuracy Using and Instrumented Gimbal, Gait & Posture, May 23, 2011, vol. 34, pp. 320-323.
Chauhan, et al., Computer-Assisted Knee Arthroplasty Versus a Conventional Jig-Based Technique, The Journal of Bone & Joint Surgery, 2004, vol. 86-B, pp. 372-377.
Cutti, et al., Motion Analysis of the Upper-Limb Based on Inertial Sensors: Part 1—Protocol Description, Journal of Biomechanics, Jan. 1, 2007, vol. 40, pp. S250.
Decking, MD., et al., Leg Axis After Computer-Navigated Total Knee Arthroplasty, The Journal of Arthroplasty, 2005, vol. 20, Issue 3, pp. 282-288.
Depuy, Johnson & Johnson, Co.,, Summit Cemented Hip System, website brochure, p. 21 pages.
De Momi, et al., "In-vitro experimental assessment of a new robust algorithm for hip joint centre estimation", Journal of Biomechanics, Feb. 26, 2009, vol. 42, pp. 989-995.
Digioia III, MD., et al., "Comparison of a Mechanical Acetabular Alignment Guide with Computer Placement of the Socket", The Journal of Arthroplasty, Apr. 2002, vol. 17, No. 3, in 6 pages.
Eric Foxlin, Chapter 7. Motion Tracking Requirements and Technologies, Handbook of Virtual Environment Technology, 2002, vol. Kay Stanney, Ed., Issue Lawrence Erlbaum Ass.
European Office Action for Application No. 04776379.2, dated May 4, 2010, in 5 pages.
Extended European Search Report issue in European Patent Application No. 13787733.8, dated Aug. 6, 2015, in 8 pages.
Extended European Search Report issue in European Patent Application No. 13790292.0, dated Oct. 28, 2015, in 7 pages.
Favre, et al., 3D Evaluation of the Knee Joint Using Ambulatory System: Application to ACL-Deficient Knees, Journal of Biomechanics, Jan. 1, 2007, vol. 40, p. S251.
Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.
Favre, et al., Ambulatory Measurement of 3D Knee Joint Angle, Journal of Biomechanics, Jan. 28, 2008, vol. 41, Issue 1029-1035.
Fixed Reference Surgical Technique, SIGMA High Performance Instruments, DePuy Orthopaedics, Inc., 2008, Warsaw, IN, in 52pages.
Ganapathi et al., "Limb Length and Femoral Offset Reconstruction During THA Using CT-Free Computer Navigation", The Journal of Bone and Joint Surgery, 2009, vol. 91-B, Supplement III, p. 399.
Goniometer, AllHeart.com, 2004, website: http://allheart.com/allheart, (1 page).
Haaker et al., "Computer-Assisted Navigation Increases Precision of Component Placement in Total Knee Arthroplasty", Clinical Orthopaedics and Related Research, Apr. 2005, vol. 433, pp. 152-159.
Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.
Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.
iASSIST Knee, Surgical Technique, Zimmer, Inc., 2012.
International Preliminary Report for Application No. PCT/US2004/018244, dated Dec. 13, 2005, in 11 pages.
International Search Report and Written Opinion issued in PCT Application No. PCT/US2013/039770, dated Sep. 25, 2013.
International Preliminary Report on Patentability issued in PCT Application No. PCT/US2013/039770, dated Nov. 11, 2014.
International Search Report and Written Opinion issued in PCT Application No. PCT/US2013/041556, dated Sep. 13, 2013.
International Preliminary Report on Patentability issued in PCT Application No. PCT/US2013/041556, dated Nov. 18, 2014.
International Search Report and Written Opinion issued in PCT Application No. PCT/US2013/053182, dated Nov. 11, 2013.
International Search Report for Application No. PCT/US2004/018244, dated Feb. 15, 2005, in 4 pages.
International Search Report for International Application No. PCT/US2009/051769 dated Nov. 19, 2009, in 11 pages.
International Search Report for International Application No. PCT/US2009/051769 dated Nov. 19, 2009, in 3 pages.
International Search Report for International Application No. PCT/US2011/022162, dated Jun. 16, 2011, in 4 pages.
International Search Report for International Application No. PCT/US2009/056553, dated Nov. 4, 2009, in 12 pages.
International Preliminary Report on Patentability issued in PCT Application No. PCT/US2013/053182, dated Feb. 17, 2015, in 10 pages.
International Search Report and Written Opinion issued in International Application No. PCT/US2016/018508, dated Jun. 22, 2016, in 19 pages.
International Preliminary Report on Patentability issued in International Application No. PCT/US2016/018508, dated Aug. 22, 2017, in 11 pages.
International Search Report and Written Opinion issued in PCT Application No. PCT/US2018/022217, dated Aug. 1, 2018, in 17 pages.
Jenny, et al., Computer-Assisted Implantation of Total Knee Prosthesis: A Case-Control Comparative Study with Classical Instrumentation, Computer Aided Surgery, 2001, vol. 6, pp. 217-220.
Konyves et al., "The importance of leg length discrepancy after total hip arthroplasty", The Journal of Bone & Joint Surgery (Br), Feb. 2005, vol. 87-B, No. 2, pp. 155-157.
Leenders, MD., et al., "Reduction in Variability of Acetabular Cup Abduction Using Computer Assisted Surgery: A Prospective and Randomized Study", Computer Aided Surgery, 2002, vol. 7, pp. 99-106.
Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.
Liebergall, Meir, et al., "Computerized Navigation for the Internal Fixation of Femoral Neck Fractures", The Journal of Bone & Joint Surgery Am, 2006, vol. 88, pp. 1748-1754.
Longo, et al., MIKA Surgical Technique, DJO Surgical, 2008, Austin Texas in 14 pages.
Luinge, Inertial Sensing of Human Movement, Twente University Press, Feb. 15, 1973, pp. in 88 pages.
Mackenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.
Medical Research Ltd, Clinical Goniometer, http://www.mie-uk.com/Gonio, 1997, p. 1 page.
Minimally Invasive TKA Genesis II Anterior Cut First, Surgical Technique, Smith & Nephew, Nov. 2003, Memphis TN, in 16 pages.
Noble et al., "Computer Simulation: How Can it Help the Surgeon Optimize Implant Position?", Clinical Orthopaedics and Related Research, Dec. 2003, vol. 417, pp. 242-252.
Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.
Partial Supplemental European Search Report issued in European Patent Application No. 13829614.0, dated Jun. 13, 2016, in 6 pages.

(56) References Cited

OTHER PUBLICATIONS

PERSEUS Intelligent Cutting Guide, Orthokey, Product Guide, in 8 pages.
PERSEUS Intelligent Cutting Guide, Smart Instruments for Knee Arthroplasty, Orthokey, in 2 pages.
Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.
Rocon, et al., Application of Inertial Sensors and Rehabilitation Robotics, Rehabilitation Robotics 2007, Jun. 1, 2007, pp. 145-150.
Sacks-Davis et. al., Atlas: A nested Relational Database System for Text Applications, IEEE Transations on Knowledge and Data Engineering, v.7, n.3, Jun. 1995, pp. 454-470.
Schep, et al., "Computer assisted orthopaedic and trauma surgery State of the art and future perspectives", Injury Int. J. Care Injured 34, (website: www.elsevier.com/locate/injury), 2003 pp. 299-306.
Scott, M.S., et al., P.F.C. Sigma Knee System, Primary Surgical Technique Part 1 of 2, DePuy International Ltd., 2003, England, (up to p. 44), in 48 pages.
Scott, M.S., et al., P.F.C. Sigma Knee System, Primary Surgical Technique Part 2 of 2, DePuy International Ltd., 2003, England, Part A (up to p. 74), in 31 pages (This reference was split in two due to size exceeding over 25MB).
Scott, M.S., et al., P.F.C. Sigma Knee System, Primary Surgical Technique Part 2 of 2, DePuy International Ltd., 2003, England, Part B (up to p. 104), in 31 pages. (This reference was split in two due to size exceeding over 25MB).
Shah et al., "Is the pelvis stable during supine total hip arthroplasty?", Acta Orthop Belg., Mar. 1, 2017, vol. 83, No. 1, pp. 81-86.
Sikorski et al., "Computer-Assisted Orthopaedic Surgery: Do We Need CAOS?", The Journal of Bone & Joint Surgery (Br), Apr. 2003, vol. 85-B, No. 3, pp. 319-323.
Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.
Stulberg, et al., Computer-Assisted Total Knee Replacement Arthroplasty, Operative Techniques in Orthopaedics, Jan. 2000, vol. 10, Issue 1, pp. 25-39.
Supplementary European Search Report issued in European Patent Application No. 13829614.0, dated Sep. 22, 2016, in 8 pages.
The Academy of Orthopaedic Surgeons, Academy News, http://www.aaos.org/wordhtml/2001news/b6-01.htm, Mar. 1, 2001, p. 1 page.
Tilt Sensors: High Accuracy, Digital Series, Crossbow Technology, Inc., pp. 32-35.
Upadhyay et al., "Medical Malpractice in Hip and Knee Arthroplasty", The Journal of Arthroplasty, 2007, vol. 22, No. 6, Suppl. 2, pp. 2-7.
Visser, et al., 3D Analysis of Upper Body Movements in Bilateral Amputee Gait Using Inertial Sensors, Journal of Biomechanics, Jan. 1, 2007, vol. 40, Issue S509.
Wentzensen et al., "Image-based hip navigation", International Orthopaedics (SICOT), 2003, vol. 27 (Suppl. 1), pp. S43-S46.
Wolfstadt et al., "An intelligent instrument for improved leg length and hip offset accuracy in total hip arthroplasty", Abstract Only.
Written Opinion for International Application No. PCT/US2009/051769, dated Nov. 19, 2009, in 7 pages.
Written Opinion for International Application No. PCT/US2011/022162, dated Jun. 16, 2011, in 9 pages.
Written Opinion of the ISR for Application No. PCT/US2004/018244, received Mar. 14, 2005, in 10 pages.
Wylde et al., "Prevalence and functional impact of patient-perceived leg length discrepancy after hip replacement", International Orthopaedics, 2009, vol. 33, pp. 905-909.
Wylde et al., "Patient-perceived leg length discrepancy after total hip replacement: prevalence and impact on functional outcome", International Orthopaedics, 2008, vol. 24, No. 2, pp. 210-216.
Zheng et al., "Technical Principles of Computer Assisted Orthopaedic Surgery", Suomen Ortopedia ja Traumatologia, Feb. 2008, vol. 31, pp. 135-147.
Zhou, et al., Use of Multiple Wearable Inertial Sensors in Upper Limb Motion Tracking, Medical Engineering & Physics, Jan. 1, 2008, vol. 30, pp. 123-133.
Zimmer NexGen Flexion Balancing Instruments, Surgical Technique, 2007, www.zimmer.com, in 44 pages.
Zorman, David, et al., "Computer-assisted total knee arthroplasty: comparative results in a preliminary series of 72 cases", ActaOrthop. Belg., 2005, 71, pp. 696-702.
https://web.archive.org/web/20151011180848/https:/www.americanphotoimp.com/productos/show/mini-clamp, "American Photo Imp. Mini Clamp", Archived Oct. 11, 2015, at Wayback Machine, in 6 pages.
https://www.youtube.com/watch?v=uKv1PH5A3WI, "FMRevu. Cell Phone DSLR Live Stream Kit | Articulating Arm Smartphone Mount" (Jul. 29, 2016) [Video]. YouTube.
https://www.youtube.com/watch?v=q7q1ce1nOtA, "CELIMA. 11 Inch Articulate Magic Arm" (Jul. 17, 2017) [Video]. YouTube.

* cited by examiner

SOFT TISSUE MEASUREMENT AND BALANCING SYSTEMS AND METHODS

INCORPORATION BY REFERENCE TO ANY PRIORITY APPLICATIONS

This application is a continuation of U.S. patent application Ser. No. 17/111,938, filed Dec. 4, 2020, which is a continuation of U.S. patent application Ser. No. 15/920,202, filed Mar. 13, 2018, which claims benefit under 35 U.S.C. § 119(e) to U.S. Provisional Patent Application No. 62/471,177, filed Mar. 14, 2017, each of which is incorporated in its entirety by reference herein. Any and all applications for which a foreign or domestic priority claim is identified in the Application Data Sheet as filed with the present application is hereby incorporated by reference in its entirety under 37 CFR 1.57.

BACKGROUND

Field

This application is directed to the field of joint replacement, and particularly to surgical tools and methods for soft tissue balancing.

Description of the Related Art

Joint replacement procedures, including knee joint replacement procedures, are commonly used to replace a patient's joint with a prosthetic joint component or components. Such procedures often use a system or systems of surgical tools and devices, including, but not limited to, cutting guides (e.g. cutting blocks) and surgical guides, to make surgical cuts along a portion or portions of the patient's bone.

Current systems and methods often use expensive, complex, bulky, and/or massive computer navigation systems which require a computer or computers, as well as three dimensional imaging, to track a spatial location and/or movement of a surgical instrument or landmark in the human body. These systems are used generally to assist a user to determine where in space a tool or landmark is located, and often require extensive training, cost, and space.

Where such complex and costly system are not used, simple methods are used, such "eyeballing" the alignment of rods with anatomical features, such as leg bones. These simple methods are not sufficiently accurate to reliably align and place implant components and the bones to which such components are attached. Without accurate, reliable placement suboptimal outcomes can result, such as with poor tissue balancing.

SUMMARY

Accordingly, there is a lack of devices, systems and methods that can be used to provide balancing, such as gap balancing and soft tissue balancing during Total Knee Arthroplasty (TKA). There is a need for balancing and alignment systems that can be integrated together to provide both measured resection and balancing. Described herein are devices, system and methods to guide one or more cuts.

In some embodiments, an orthopedic system for orienting a cutting plane during a joint replacement procedure is provided. The system can include a tibial baseplate. The system can include a femoral baseplate. The system can include a surgical orientation device coupled or configured to couple to the at least one of the tibial baseplate and the femoral baseplate. The surgical orientation device can include a housing. The surgical orientation device can include an inertial sensor configured to monitor the orientation of the surgical orientation device in a three-dimensional coordinate reference system while distracting the joint. The inertial sensor can be disposed on or in the housing. The surgical orientation device can include a user interface comprising a display screen configured to display a measurement related to distracting the joint.

In some embodiments, the inertial sensor comprises at least one gyroscopic sensor, accelerometer sensor, tilt sensor, and/or other similar device or devices configured to measure, and/or facilitate determination of, an orientation of the surgical orientation device. In some embodiments, the inertial sensor can be configured to provide measurements relative to a reference point, line, plane, and/or gravitational zero. In some embodiments, the inertial sensor comprises gyroscopic sensors configured to detect angular position changes or accelerometers configured to detect linear position changes. The system can include a drill guide coupled with the tibial baseplate. The system can include a reference sensor device comprising a camera. In some embodiments, the camera is oriented transverse to a longitudinal axis of a housing of the reference sensor device. In some embodiments, the camera is configured to capture an image of a linear scale or otherwise make or confirm the measurement related to the distracting the knee joint.

In some embodiments, an orthopedic orientation system for use in a joint procedure is provided. The system can include a tibial baseplate. The system can include a femoral baseplate. The system can include an adjustment device enabling at least one degree of freedom of the femoral baseplate relative to the tibial baseplate when the tibial baseplate is in a fixed position and orientation relative to the tibia. The system can include the adjustment device enabling at least one additional and different degree of freedom of the femoral baseplate relative to the tibial baseplate when the tibial baseplate is in a fixed position and orientation relative to the tibia. The system can include a first orientation device configured to be coupled to the femoral baseplate. The first orientation device can include a sensor located within the housing, the sensor configured to monitor the position and/or orientation of the first orientation device. The first orientation device can include a display configured to inform a user of the position and/or orientation of the first orientation device. The system can include a second orientation device configured to be coupled to the tibial baseplate.

In some embodiments, the sensor comprises gyroscopic sensors to detect angular position changes and/or accelerometers to detect linear position changes. The sensor can alternatively or additionally include gravitational, magnetic, and/or other inertial sensors in other embodiments. In some embodiments, the system is configured to determine the orientation of the mechanical axis of the joint. In some embodiments, the at least one degree of freedom of the femoral baseplate relative to the tibial baseplate includes or is translation. In some embodiments, the at least one additional degree of freedom of the femoral baseplate relative to the tibial baseplate includes or is rotation.

In some embodiments, a method of performing an orthopedic procedure is provided. The method can include coupling a first orientation device with a portion of the knee joint, the surgical orientation device comprising a first inertial sensor. The method can include coupling a second orientation device with a portion of the knee joint, the second surgical orientation device comprising a second inertial sensor. The method can include collecting an inertial sensor output from the first inertial sensor or the second inertial sensor. The method can include distracting the knee joint. The method can include cutting the femur. The method can include determining with the first orientation device and the first orientation device a location of the mechanical axis of a leg or of a bone adjacent to the knee joint, e.g. the femur or the tibia. The method can include displaying the inertial sensor output from the first inertial sensor or the second inertial sensor. The method can include storing the inertial sensor output from the first inertial sensor or the second inertial sensor. The method can include comparing the inertial sensor output at a first time and a second time during the procedure. The method can include calculating, measuring, detecting and/or collecting a distraction distance. In some embodiments, collecting a distraction distance comprises capturing an image. In other embodiments collecting includes a distraction distance. The method can include inserting one or more pins into the femur. The method can include mounting a cutting block to the one or more pins. The method can include coupling a drill guide to the knee joint.

In some embodiments, an orthopedic system for orienting a cutting plane during a joint replacement procedure is provided. The system can include a tibial member configured to couple to tibia. The system can include a guide coupled to the tibial member, the guide configured to guide the insertion of pins into a femur. The system can include a surgical orientation device coupled or configured to couple to the at least one of the tibia or the femur. The surgical orientation device can include a housing. The surgical orientation device can include an inertial sensor configured to monitor the orientation of the surgical orientation device in a three-dimensional coordinate reference system while distracting the joint. The surgical orientation device can include a user interface comprising a display screen configured to display a measurement related to femur rotation.

In some embodiments, an orthopedic system for orienting a cutting plane during a joint replacement procedure is provided. The system can include a tibial member. The system can include a femoral member. The system can include a surgical orientation device coupled or configured to couple to the at least one of the tibial member and the femoral member. The surgical orientation device can include a housing. The surgical orientation device can include an inertial sensor configured to monitor the orientation of the surgical orientation device in a three-dimensional coordinate reference system while distracting the joint. The surgical orientation device can include a user interface comprising a display screen configured to display a measurement related to distracting the joint.

The system can include a reference sensor device coupled or configured to couple to the at least one of the tibial member and the femoral member. In some embodiments, the surgical orientation device is configured to couple to the femoral member and the reference sensor device is configured to couple to the tibial member. In some embodiments, the inertial sensor comprises at least one gyroscopic sensor, accelerometer sensor, tilt sensor, and/or other similar device or devices configured to measure, and/or facilitate determination of, an orientation of the surgical orientation device. In some embodiments, the inertial sensor can be configured to provide measurements relative to a reference point, line, plane, and/or gravitational zero. In some embodiments, the inertial sensor comprises gyroscopic sensors configured to detect angular position changes or accelerometers configured to detect linear position changes. The system can include a drill guide coupled with the tibial member. The system can include a resection guide coupled with the tibial member. The system can include a reference sensor device comprising a camera. In some embodiments, the camera is oriented transverse to a longitudinal axis of a housing of the reference sensor device. In some embodiments, the camera is configured to capture an image of the measurement related to the distracting the knee joint. In some embodiments, the measurement comprises a distance measurement corresponding to a distance between the tibia and the femur. In some embodiments, the measurement is configured to correspond to a measurement marking on a resection guide. In some embodiments, the measurement comprises a distance measurement to match a gap in extension. In some embodiments, the measurement comprises a distance measurement to facilitate the posterior femoral cut. In some embodiments, the measurement comprises an angle measurement corresponding to an angle between the tibia and the femur. In some embodiments, the measurement comprises an angle measurement to facilitate soft tissue release. The system can include a moveable interface to stabilize the orthopedic system against the tibia. In some embodiments, the moveable interface is configured to limit insertion of the tibial member in the joint space. The system can include a resection guide.

In some embodiments, an orthopedic orientation system, for use in a joint procedure, is provided. The system can include a tibial member. The system can include a femoral member. The system can include an adjustment device enabling at least one degree of freedom of the femoral member relative to the tibial member when the tibial baseplate is in a fixed position and orientation relative to the tibia. In some embodiments, the adjustment device enabling at least one additional and different degree of freedom of the femoral member relative to the tibial member when the tibial member is in a fixed position and orientation relative to the tibia. The system can include a first orientation device configured to be coupled to the femoral baseplate. The first orientation device can include a sensor located within the housing, the sensor configured to monitor the position and/or orientation of the first orientation device. The first orientation device can include a display configured to inform a user of the position and/or orientation of the first orientation device. The system can include a second orientation device configured to be coupled to the tibial member.

In some embodiments, the sensor comprises gyroscopic sensors to detect angular position changes and/or accelerometers to detect linear position changes. In some embodiments, the system is configured to determine the orientation of the mechanical axis of the joint. In some embodiments, the at least one degree of freedom of the femoral member relative to the tibial member is translation. In some embodiments, the at least one degree of freedom of the femoral member relative to the tibial member relates to distraction between the femur and the tibia. In some embodiments, the at least one additional degree of freedom of the femoral member relative to the tibial member is rotation. In some embodiments, the adjustment device comprises a rounded portion of a post configured to move within a rounded guide portion. In some embodiments, the adjustment device comprises a rack and drive pinion. In some embodiments, the adjustment device comprises a pawl and ratchet. In some embodiments, the adjustment device is configured to apply a force between 150 N and 200 N. In some embodiments, the adjustment device comprises a post comprising a portion with a round or circular cross-section. The system can include a bracket, wherein a longitudinal axis of the first orientation device is offset from a longitudinal axis of the second orientation device when the first orientation device is coupled with the bracket. The system can include a bracket which positions the first orientation device to the side of the second orientation device. In some embodiments, the second orientation device comprises a camera configured to capture an image of a marking related to a distraction distance. In some embodiments, the second orientation device comprises a camera configured to capture an image of a portion of a post of the adjustment device.

In some embodiments, a method of performing an orthopedic procedure is provided. The method can include coupling a first orientation device with a portion of the knee joint, the surgical orientation device comprising a first inertial sensor. The method can include coupling a second orientation device with a portion of the knee joint, the second surgical orientation device comprising a second inertial sensor. The method can include collecting an inertial sensor output from the first inertial sensor or the second inertial sensor. The method can include distracting the knee joint. The method can include cutting the femur.

The method can include determining with the first orientation device and the second orientation device a location of the mechanical axis of a bone adjacent to the knee joint. The method can include displaying the inertial sensor output from the first inertial sensor or the second inertial sensor. The method can include storing the inertial sensor output from the first inertial sensor or the second inertial sensor. The method can include comparing the inertial sensor output at a first time and a second time during the procedure. The method can include collecting a distraction distance. In some embodiments, collecting a distraction distance comprises capturing an image. The method can include inserting one or more pins into the femur. The method can include mounting a cutting block to the one or more pins. The method can include coupling a drill guide to the knee joint.

In some embodiments, a method of performing an orthopedic procedure is provided. The method can include coupling a first orientation device with at least one of a tibial member and a femoral member, the first orientation device comprising a first inertial sensor. The method can include coupling a second orientation device with at least one of the tibial member and the femoral member. The method can include inserting the tibial member and the femoral member in the joint space. The method can include distracting the knee joint. The method can include balancing the soft tissue.

The method can include determining with the first orientation device and the second orientation device a location of the mechanical axis of the limb. The method can include displaying a distraction distance on a display of the first orientation device. The method can include displaying a femoral angle on a display of the first orientation device.

The method can include storing a distraction distance in a memory of the first orientation device. The method can include storing a femoral angle in a memory of the first orientation device. The method can include comparing a distraction distance in extension and flexion. The method can include collecting a distraction distance. In some embodiments, collecting a distraction distance comprises capturing an image. In some embodiments, coupling a first orientation device with a portion of the knee joint comprises coupling the first orientation device to a femoral member. In some embodiments, coupling a second orientation device with a portion of the knee joint comprises coupling the second orientation device to a tibial member. In some embodiments, distracting the knee joint comprises distracting the knee joint in extension. The method can include recording an extension gap distance. The method can include distracting the knee joint in flexion after recording an extension gap distance. The method can include matching the extension gap distance with a marking on a resection guide. The method can include performing a posterior femoral cut corresponding to the extension gap measurement. In some embodiments, distracting the knee joint comprises distracting the knee joint in extension and balancing the soft tissue comprises balancing the soft tissue in extension. In some embodiments, balancing the soft tissue comprises balancing the soft tissue only in extension. The method can include measuring a femoral rotation angle in extension and flexion. The method can include recording a femoral rotation angle in flexion.

In some embodiments, an orthopedic system for orienting a cutting plane during a joint replacement procedure is provided. The system can include a tibial member coupled to tibia. The system can include a guide coupled to the tibial member. The system can include a surgical orientation device coupled or configured to couple to the at least one of the tibia or the femur. The surgical orientation device can include a housing. The surgical orientation device can include an inertial sensor configured to monitor the orientation of the surgical orientation device in a three-dimensional coordinate reference system while distracting the joint. The surgical orientation device can include a user interface comprising a display screen configured to display a measurement related to femur rotation.

In some embodiments, the guide is configured to guide the insertion of pins into a femur. In some embodiments, the guide is configured to guide the posterior femoral cut.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments.

DETAILED DESCRIPTION

This application discloses systems and methods that can be used in a knee joint replacement procedure to measure how soft tissue around the knee acts on the bones of the knee joint. These measurements enable a surgeon to be better informed of the dynamics of the patient's knee joint anatomy such that preparation of the bones and application of the prosthetic components can be better adapted to the patient, resulting in superior outcomes.

A. Alignment

1. Femoral and Tibial Systems for Measured Resection

Prior to replacing the knee joint with prosthetic components, surgical cuts commonly called resections are generally made with a cutting tool or tools along a portion or portions of both the proximal tibia and distal femur. These cuts are made to prepare the tibia and femur for the prosthetic components. After these cuts are made, the prosthetic components can be attached and/or secured to the tibia and femur.

The desired orientation and/or position of these cuts, and of the prosthetic components, can be determined pre-operatively and based, for example, on a mechanical axis running through an individual patient's leg. Once the desired locations of these cuts are determined pre-operatively, the surgeon can use the systems and methods described herein to make these cuts accurately. While the systems and methods are described in the context of a knee joint replacement procedure, the systems and/or their components and methods can similarly be used in other types of medical procedures, including but not limited to hip replacement procedures. U.S. Pat. Nos. 8,998,910, 9,339,226 and 8,118,815 disclose additional embodiments of tibial and femoral preparation system, and are incorporated by reference in their entirety. U.S. Pub. No. 2014/0052149 and U.S. Pub. No. 2016/0242934 disclose additional features of surgical orientation device and references devices, as well as other components which may be incorporated into systems described herein, both of which are incorporated by reference.

Figure 1A:
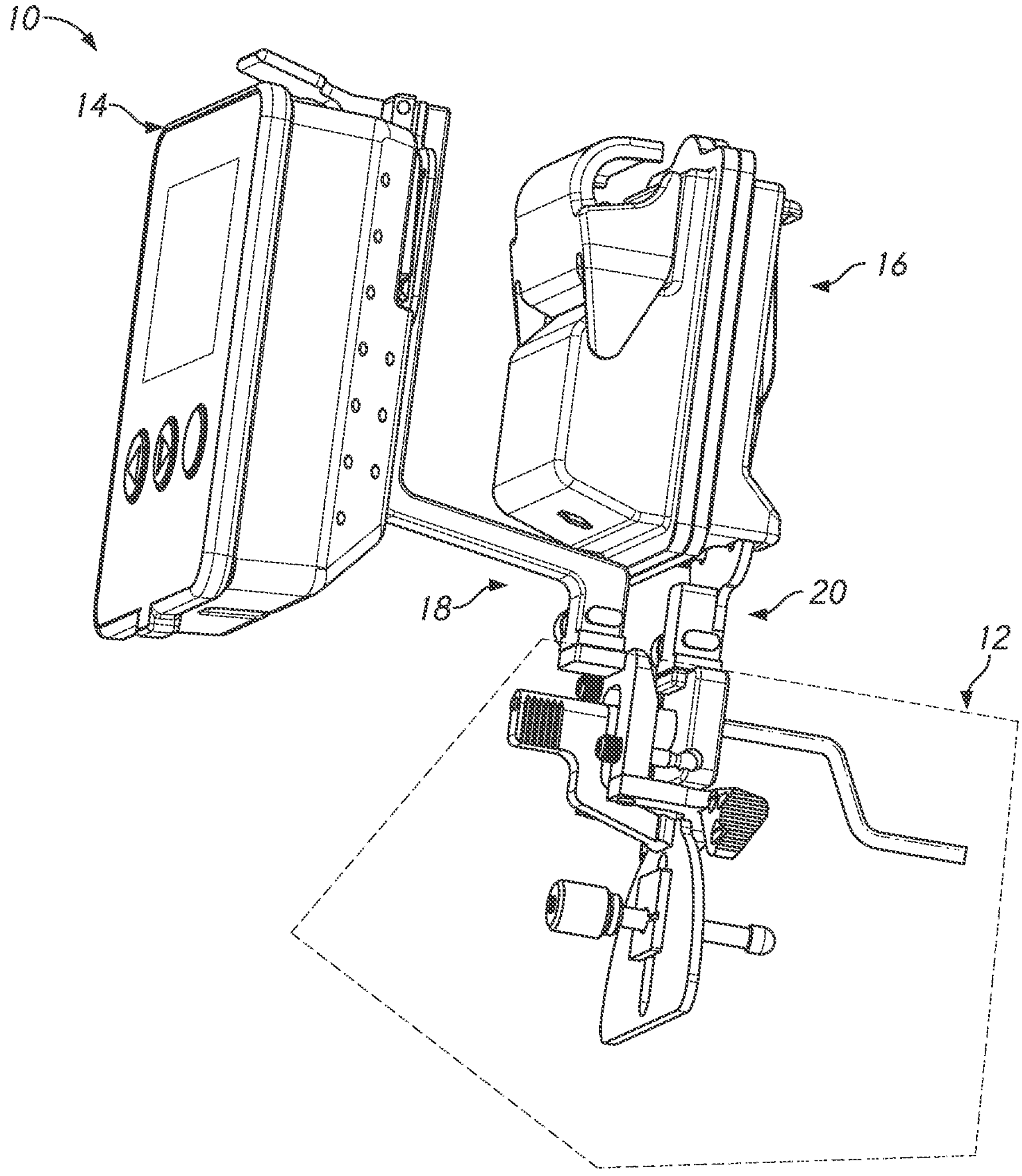
FIGS. 1A-1C illustrate an assembled view of a femoral preparation system.
Figure 1B:
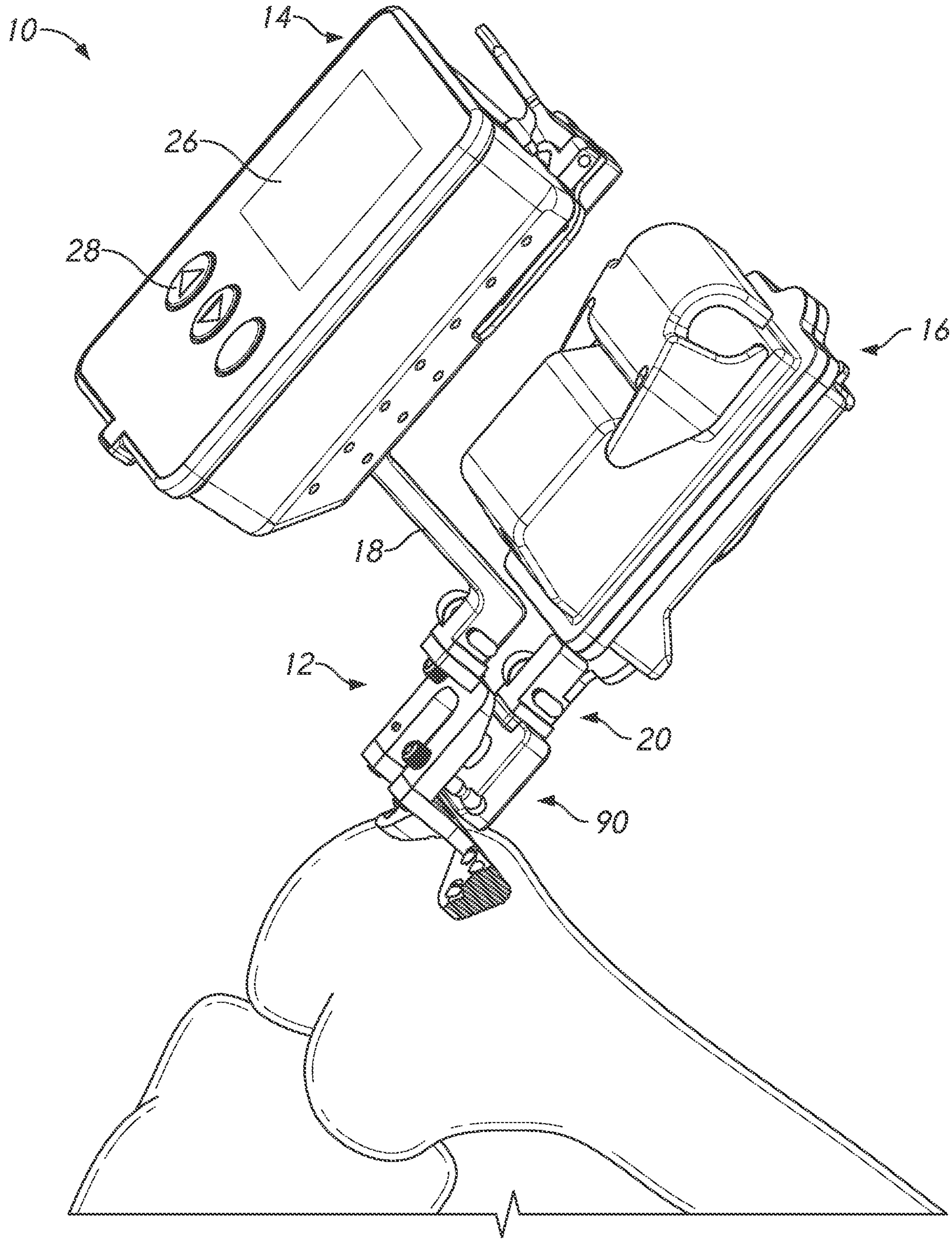

With reference to FIGS. 1A and 1B, a femoral preparation system 10 can be used to modify a natural femur with a distal femoral resection, enabling a prosthetic component to be securely mounted upon the distal end of the femur. The femoral preparation system 10 can comprise, for example, a femoral jig assembly 12, a surgical orientation device 14, a reference device 16, a first coupling device 18, and a second coupling device 20. The first coupling device 18 can be used to attach the surgical orientation device 14 to the femoral jig assembly 12. The second coupling device 20 can be used to attach the reference sensor device 16 with the femoral jig assembly 12.

The surgical orientation device 14 can be used to measure and record the location of anatomical landmarks used in a total knee procedure, such as the location of the mechanical axis of a leg (and femur). "Surgical orientation device" is a broad term and is to be given its ordinary and customary meaning to a person of ordinary skill in the art (i.e. it is not to be limited to a special or customized meaning) and includes, without limitation, any device that can be used to provide orientation information or perform orientation calculations for use in a surgical or other procedure. The mechanical axis of a leg, as defined herein, generally refers to a line extending from the center of rotation of a proximal head of a femur (e.g. the center of the femoral head) through, ideally, the approximate center of the knee, to a center, or mid-point, of the ankle. The mechanical axis of the femur is the same axial line extending from the center of rotation of the proximal head of the femur through the center of the distal end of the femur (the center of distal end of the femur is commonly described as the center of the intercondylar notch). Generally, an ideal mechanical axis in a patient allows load to pass from the center of the hip, through the center of the knee, and to the center of the ankle. The surgical orientation device 14, in conjunction with the reference device 16 described herein, can be used to locate the spatial orientation of the mechanical axis. In certain techniques described herein, the surgical orientation device 14 and the reference device 16 can be used to locate one, two, or more planes intersecting the mechanical axis. The surgical orientation device 14 and the reference device 16 can also be used for verifying an alignment of an orthopedic fixture or fixtures, or a cutting plane or planes, during an orthopedic procedure. The surgical orientation device 14, and the reference device 16, as described herein, can each be used alone or in conjunction with other devices, components, and/or systems.

The surgical orientation device 14 can comprise a display 26. The display 26 can be sized such that a user can readily read numbers, lettering, and/or symbols displayed on the display screen while performing a medical procedure. The surgical orientation device 14 can further comprise at least one user input device 28. The at least one user input device 28 can comprise a plurality of buttons located adjacent the display 26. The buttons can be activated, for example, by a finger, hand, and/or instrument to select a mode or modes of operation of the device 14, as discussed further below. The surgical orientation device 14 includes a user interface with which a clinician can interact during a procedure. The surgical orientation device 14 includes an electrical system. The electrical system can include one or more features including: one or more sensors, an electronic control unit that communicates with one or more sensors, one or more visible alignment indicators, a power supply, the display 26, memory, one or more user input devices 28, one or more processors, program logic, other substrate configurations representing data and instructions, controller circuitry, processor circuitry, processors, general purpose single-chip or multi-chip microprocessors, digital signal processors, embedded microprocessors, microcontrollers, other output devices and/or one or more input/output ("I/O") ports. In certain embodiments, the electronic control unit can be configured to convert the electronic data from a machine-readable format to a human readable format for presentation on the display 26. The electronic control unit can communicate with internal memory and/or the external memory to retrieve and/or store data and/or program instructions for software and/or hardware. The internal memory and the external memory can include random access memory ("RAM"), such as static RAM, for temporary storage of information and/or read only memory ("ROM"), such as flash memory, for more permanent storage of information. In general, the sensor(s) can be configured to provide continuous real-time data to the surgical orientation device 14. The electronic control unit can be configured to receive the real-time data from the sensor(s) and to use the sensor data to determine, estimate, and/or calculate an orientation or position of the surgical orientation device 14. The orientation information can be used to provide feedback to a user during the performance of a surgical procedure, such as a total knee joint replacement surgery, as described in more detail herein.

In some embodiments, in addition or alternatively to the surgical orientation device 14, electronic equipment can include a display. The electronic equipment can include one or more handheld devices such as a computer, desktop computer, laptop computer, or tablet computer such as an iPad®. In some embodiments, the display is located within the surgical field. In some embodiments, the display is located outside the surgical field. In some embodiments, the reference sensor device 16 can include a display. In some embodiments, in addition or alternatively to the surgical orientation device 14, electronic equipment can include at least one user input device 28. The user input device 28 can be activated, for example, by a finger, hand, and/or instrument to select a mode or modes of operation of one or more electronic devices of the system including the surgical orientation device 14 and/or the reference sensor device 16. The electronic equipment can include software and/or hardware for the systems described herein. The electronic equipment can include external memory for the systems described herein. The surgical orientation device 14 and/or the reference sensor device 16 can connect to the internet. The surgical orientation device 14 and/or the reference sensor device 16 can transmit or receive information from the internet. The surgical orientation device 14 and/or the reference sensor device 16 can connect to the cloud. The surgical orientation device 14 and/or the reference sensor device 16 can transmit or receive information from the cloud.

In some arrangements, the one or more sensors can comprise at least one orientation sensor configured to provide real-time data to the electronic control unit related to the motion, orientation, and/or position of the surgical orientation device 14. For example, the sensor module can comprise at least one gyroscopic sensor, accelerometer sensor, tilt sensor, magnetometer and/or other similar device or devices configured to measure, and/or facilitate determination of, an orientation of the surgical orientation device 14. In some embodiments, the sensors can be configured to provide measurements relative to a reference point(s), line (s), plane(s), and/or gravitational zero. Gravitational zero, as referred to herein, refers generally to an orientation in which an axis of the sensor is perpendicular to the force of gravity, and thereby experiences no angular offset, for example tilt, pitch, roll, or yaw, relative to a gravitational force vector. In other embodiments, the sensor(s) can be configured to provide measurements for use in dead reckoning or inertial navigation systems.

In various embodiments, the sensor(s) comprise one or more accelerometers that measure the static acceleration of the surgical orientation device 14 due to gravity. For example, the accelerometers can be used as tilt sensors to detect rotation of the surgical orientation device 14 about one or more of its axes. The one or more accelerometers can comprise a dual axis accelerometer (which can measure rotation about two axes of rotation) or a three-axis accelerometer (which can measure rotation about three axes of rotation). The changes in orientation about the axes of the accelerometers can be determined relative to gravitational zero and/or to a reference plane registered during a tibial or femoral preparation procedure as described herein.

In certain embodiments, a multi-axis accelerometer (such as the ADXL203CE MEMS accelerometer available from Analog Devices, Inc. or the LIS331DLH accelerometer available from ST Microelectronics.) detects changes in orientation about two axes of rotation. For example, the multi-axis accelerometer can detect changes in angular position from a horizontal plane (e.g., anterior/posterior rotation) of the surgical orientation device 12 and changes in angular position from a vertical plane (e.g., roll rotation) of the surgical orientation device 14. The changes in angular position from the horizontal and vertical planes of the surgical orientation device 14 (as measured by the sensor can also be used to determine changes in a medial-lateral orientation (e.g., *varus*/valgus rotation) of the surgical orientation device 14.

In some arrangements, the sensors comprise at least one single- or multi-axis gyroscope sensor and at least one single- or multi-axis accelerometer sensor. For example, the sensor can comprise a three-axis gyroscope sensor (or three gyroscope sensors) and a three-axis accelerometer (or three accelerometer sensors) to provide position and orientation measurements for all six degrees of freedom of the surgical orientation device 14. In some embodiments, the sensors provide an inertial navigation or dead reckoning system to continuously calculate the position, orientation, and velocity of the surgical orientation device 14 without the need for external references In one embodiment, a surgical orientation system includes the surgical orientation device 14 and a reference device 16. The reference device 16 can include any of the features of the surgical orientation device 14. The surgical orientation device 14 and/or the reference device 16 includes in one embodiment one or more sensors that together can form an inertial measurement unit (IMU). In particular, the IMU includes a first sensor for determining acceleration and a second sensor for determining gyroscopic positioning. As discussed herein, the first sensor can be an accelerometer and the second sensor can be a gyroscopic sensor. The reference device 16 also includes a transmitter for sending data from the sensors to the electrical system of the surgical orientation device 14. The information received from the reference device 16 can be fed to an input port, or alternatively, the electronic control unit of the surgical orientation device 14 can itself receive the information wirelessly. The information from the reference device 16 can correspond, for example, to the position and/or orientation of the reference device 16, and can be used by the surgical orientation device 14 to determine an aggregate, relative or overall, position and/or orientation of the surgical orientation device 14.

The reference sensor device 16 can be used to measure and record the location of anatomical landmarks used in a total knee procedure, such as the location of the mechanical axis of a leg (and femur). "Reference sensor device" is a broad term and is to be given its ordinary and customary meaning to a person of ordinary skill in the art (i.e. it is not to be limited to a special or customized meaning) and includes, without limitation, any device that can be used to reference another device, and/or to provide orientation information or perform calculations identically or similar to the surgical orientation device 14 described above. In some embodiments, the reference sensor device 16 can comprise the same or similar components as the surgical orientation device 14 described above. Further description of a reference sensor can be found, for example and without limitation, in paragraphs [0176]-[0178] of U.S. patent application Ser. No. 12/509,388, which is incorporated by reference herein. Additional details of systems, devices, sensors, and methods are set forth in U.S. application Ser. No. 10/864,085 filed Jun. 9, 2004, U.S. application Ser. No. 11/182,528 filed Jul. 15, 2009, U.S. application Ser. No. 12/557,051 filed Sep. 10, 2009, U.S. application Ser. No. 12/509,388 filed Jul. 24, 2009, U.S. application Ser. No. 13/011,815 filed Jan. 21, 2011, U.S. application Ser. No. 13/115,065, filed May 24, 2011; U.S. application Ser. No. 14/399,046 filed Nov. 5, 2014, U.S. application Ser. No. 14/401,274 filed Nov. 14, 2014, U.S. application Ser. No. 13/800,620 filed Mar. 13, 2013, U.S. application Ser. No. 14/643,864 filed Mar. 10, 2015 and U.S. application Ser. No. 15/550,564 filed Aug. 11, 2017, which are all incorporated by reference herein in their entireties for all purposes.

Figure 1C:
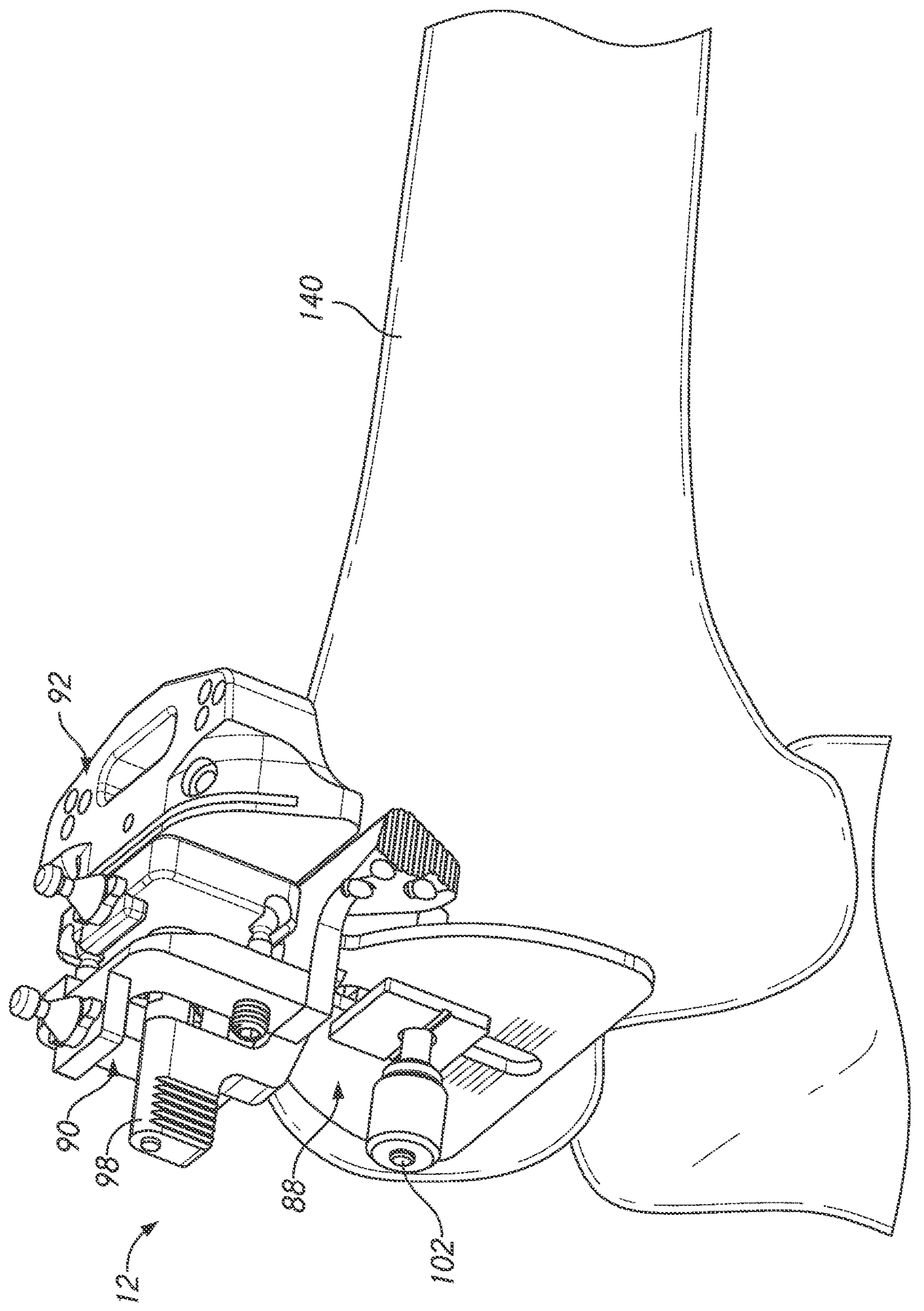

Referring to FIG. 1C, the femoral jig assembly 12 can comprise an orthopedic assembly for femoral preparation during a total knee replacement procedure. In a preferred arrangement, the femoral jig assembly 12 can comprise a distal guide assembly 88, a microblock assembly 90, a cutting block 92, an articulating arm 98, and a midline pin 102. In preparation for the distal femoral resection, the method can begin with locating a distal point that is intersected by the mechanical axis of the femur. The method can comprise installing the femoral jig assembly 12 via the midline pin 102 in the approximate center of the intercondylar notch, which places the femoral jig assembly 12 in an approximate center position of the distal end portion of the femur.

The reference sensor device 16 and/or orientation device 14 can be used to determine the relative coordinates of a center pivot point on the femur. By determining the coordinates of the pivot point of the femoral head, the reference sensor device 16 and/or surgical orientation device 14 can calculate the location and/or orientation of the mechanical axis that extends through the femur.

In order to determine the coordinates of the pivot point of the femoral head (i.e. the pivot point of the mechanical axis), the leg can be moved (e.g. swung). For example, the leg can be moved in several different directions and/or planes, with the reference sensor device 16 and/or surgical orientation device 14 attached. Readings such as angular rate and acceleration ("surgical orientation device 14 and/or reference sensor device 16 data") of the femur 140 can be obtained by the reference sensor device 16 and/or surgical orientation device 14 until the location and/or orientation of the mechanical axis of the leg and the femur 140 ("femoral mechanical axis") is found. In one embodiment, where one or more multi-axis (e.g., two-axis) accelerometers and gyroscopes are used, surgical orientation device 14 and/or reference sensor device 16 data for each movement of the femur 140 can be numerically integrated over time to obtain a trajectory of position and velocity points (one point for each IMU data). The IMU data can be integrated without imposing any plane trajectory constraints on movements of the femur 140.

The acceleration and angular rate sensed by the reference sensor device 16 and/or surgical orientation device 14 during the leg movement can be processed while the leg is moved about its pivot point. The reference sensor device 16 and/or surgical orientation device 14 can provide an output vector representing the center of the rotation with respect to the inertial sensor axes of the reference sensor device 16 and/or surgical orientation device 14.

In some embodiments, prior to determining the location and/or orientation of the center of rotation of the mechanical axis, an error correction technique can be used to remove biases in the surgical orientation device 14 and/or reference sensor device 16. For example, an error correction technique can include assessing 1) static bias; 2) gyroscopic bias; and 3) accelerometer bias in the surgical reference sensor device 16 and/or surgical orientation device 14.

At least one purpose of the surgical orientation device 14 and/or reference device 16 and systems described herein is to provide guidance to the surgeon as to how to position a cutting block on the bone in order to achieve a cutting plane that is perpendicular to the load bearing axis of the bone (or some number of degrees off of that perpendicular plane if desired). A jig, such as that described above, can be fixed to the bone to be cut and the reference sensor device 16 and surgical orientation device 14 can be attached to that jig (one device is attached to a fixed portion of the jig to act as a reference to the bone's orientation and the other device is attached to an articulating arm of the jig to provide the surgeon a means to find and set the desired cutting plane). The articulating arm of the jig can be constrained to only be moved in two dimensions, e.g., pitch and yaw (not rotation).

These two axes form a plane that can be adjusted to guide the placement of the cutting block which guides the saw to cut the bone on that plane.

Once biases have been removed, and the reference sensor device 16 and/or surgical orientation device 14 has calculated the pivot point of the mechanical axis as described above and located the mechanical axis, the user can begin adjusting and orienting the cutting block 92 relative to the location of the mechanical axis. For example, the surgical orientation device 14 can display the varus/valgus and flexion/extension angle adjustments needed for the surgical orientation device 14 (and the femoral jig assembly 12) to reach neutral alignment with the mechanical axis that passes through the femoral head.

Advantageously, in some embodiments the reference sensor device 16 can enable the procedure to proceed without fixation of the leg being operated upon because the reference sensor device 16 can track the relative positions of the leg, e.g. of the femur. For example, at least one of the reference sensor device 16 and the surgical orientation device 14 can communicate with the other, such that any relative movement of one of the devices can be tracked by the other, and the resulting overall orientation of the reference sensor device 16 and/or surgical orientation device 14 can be displayed on display 26 of the surgical orientation device 14. In some embodiments, the reference sensor device 16 can track movement of the leg (i.e. femur or tibia), such that if the leg moves during a procedure, the overall orientation of the surgical orientation device 14 can remain accurate.

Figure 2A:
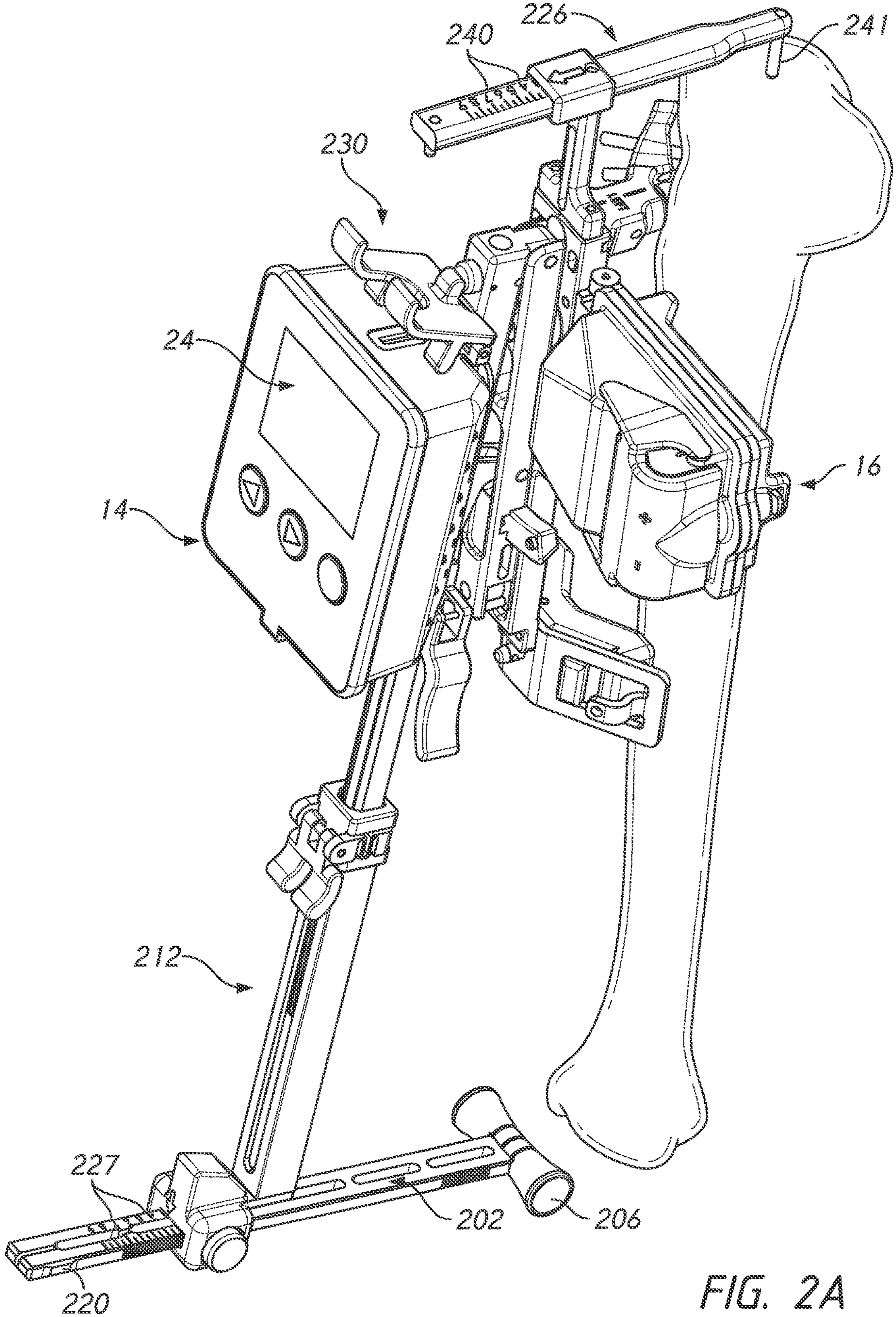
FIGS. 2A-2C illustrate an assembled view of a tibial preparation system.

Referring to FIG. 2A, a tibial preparation system 210 can be used for modifying a natural tibia with a proximal tibial resection to enable a prosthetic component to be securely mounted upon the proximal end of the tibia. The tibial preparation system 210 can comprise, for example, a tibial jig assembly 212, a landmark acquisition assembly 214, the surgical orientation device 14, and the reference sensor device 16.

The tibial jig assembly 212 can comprise an orthopedic assembly for use in preparing a tibia for a prosthetic component, and in particular for making angular adjustments relative to an anatomical feature.

In a preferred arrangement, the tibial jig assembly 212 can comprise a component for adjusting a posterior/anterior slope of the surgical orientation device 14 and/or a cutting block. In a preferred arrangement, the tibial jig assembly 212 can also comprise a component for adjusting the varus/valgus slope of a cutting block.

FIG. 2A illustrate various features of the landmark acquisition assembly 214. The landmark acquisition assembly 214 can comprise a structure that is configured to contact and/or obtain information about anatomical landmarks on the human body. The landmark acquisition assembly 214 can be attached to or form part of the tibial jig assembly 212.

Referring to FIG. 2A, the probe assembly 202 can include an elongate member 220. The probe assembly 202 can comprise a probe member 206 that is located on at least one end of the elongate member 220. The probe member 206 can be configured to contact an anatomical landmark, such as for example a malleolus on a patient's ankle. The elongate member 220 can further comprise a series of markings 227, indicating distance and/or length. The markings can be used to measure, for example, an AP offset of the probe member 206.

The midline reference probe assembly 226 can be positioned at an appropriate anatomical location at the proximal tibia, for example at a point just posterior to the insertion of the anterior cruciate ligament (ACL), or at another suitable anatomical landmark. For example, a tip 241 of the midline reference probe assembly 226 can be resting over the insertion point of the anterior cruciate ligament in the knee, and/or a soft point on the top of the tibia commonly referred to as the A/P point of the mechanical axis. This point is generally located along a tibial spine on top of the tibia, and marks the location of a point along the mechanical axis of the leg. Indicia of distance on an upper surface of the midline reference probe assembly 226 (e.g. via markings 240) can be noted and a corresponding A/P offset position can be set in the landmark acquisition assembly 214 (e.g. via markings 227 described above).

FIG. 2A illustrates the tibial jig assembly 212 fully assembled with a reference sensor device 16 coupled to the reference sensor device interface 228 and with a surgical orientation device 14 coupled with the orientation device interface 230.

Figure 2B:
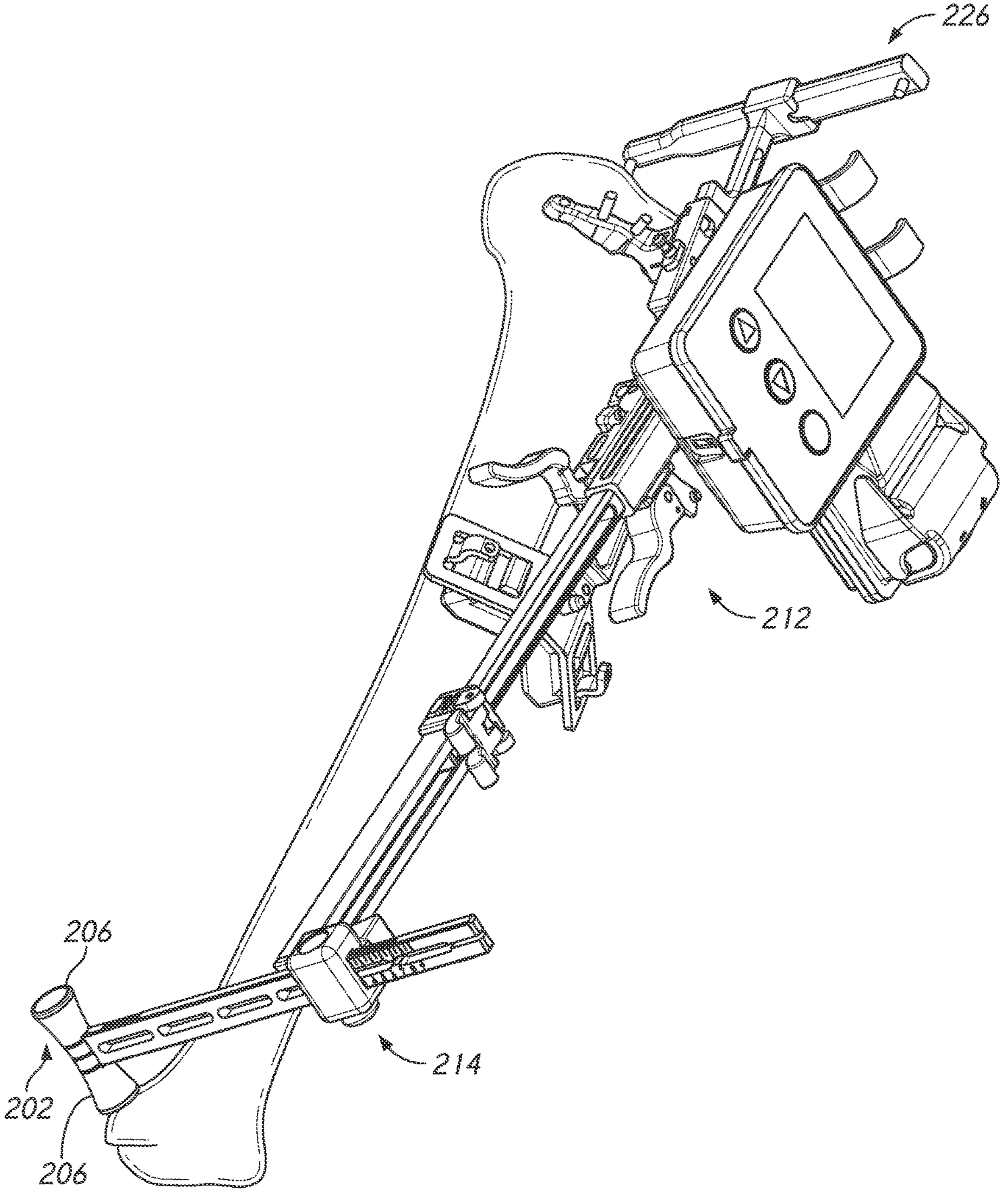

Referring to FIG. 2B, the method can further comprise acquiring landmarks to determine the location of the mechanical axis passing through the tibia. For example, landmarks can be acquired by engaging the probe member 206 of probe assembly 202 first with a medial malleolus, and then with the lateral malleolus (or vice versa). FIG. 2B illustrates acquisition of one malleolus. Acquisition of the other malleolus can similarly be accomplished by swinging a portion or portions of the tibial jig assembly 212 such that the probe member 206 contacts the other side of the leg. Thereafter, the surgical orientation device 14 can determine the location of the mechanical axis, e.g., by locating sagittal and coronal planes extending through the mechanical axis. In some embodiments, the surgical orientation device can calculate the location of the mechanical axis by assuming that the mechanical axis extends from the point of contact of the midline reference probe assembly 226 with the proximal tibia through a point that is halfway between the two malleolus points contacted by the probe member 206 on either side of the leg, or any other appropriate point.

In some embodiments, the user can activate the surgical orientation device 14, such as by pressing one of the user inputs 28 on the surgical orientation device 14, during each landmark acquisition. Once activated, the, surgical orientation device 14 can register (e.g. record) the orientation of the surgical orientation device 14 as a reference position (e.g. a first reference position). For example, the surgical orientation device 14 can register and/or calculate the current orientation of the surgical orientation device 14 based on data collected from the sensor(s) inside the surgical orientation device 14. The orientation of the surgical orientation device 14 in a first reference position can be used to identify and register the orientation of a coronal plane which contains the mechanical axis of the leg, as well as to determine a first reference point for identifying the location and/or orientation of a sagittal plane containing this same mechanical axis.

The user can then swing the probe member 206 over to the other (e.g. medial) side of the leg, such that the reference probe 206 is located adjacent the other malleolus. During each landmark acquisition, the user can palpate the ankle. Once the location of the other (e.g. medial) malleolus is identified, the user can press one of the user inputs 28 on the surgical orientation device 14 to cause the surgical orientation device 14 to determine the orientation of the surgical orientation device 14 in a second reference position. For example, the surgical orientation device 14 can register and/or calculate the current orientation of the surgical orientation device 14 based on data collected from the sensor(s) inside the surgical orientation device 14.

The orientation of the surgical orientation device 14 in the second reference position can again be used to identify the orientation of a coronal plane extending through the tibia that contains the mechanical axis of the leg, and/or can be used to locate a second reference point for identifying the location and/or orientation of a sagittal plane containing the same mechanical axis.

When using the surgical orientation device 14 to determine the first and second reference positions, output of the sensor(s) in the surgical orientation device 14 can be monitored in a manner that minimizes error in the reading. For example, a transient phase can be eliminated in the output of the sensors to arrive at an accurate estimation of the given anatomical landmark.

Once information about both the first and second reference positions has been acquired and registered in the surgical orientation device 14, the surgical orientation device 14 can determine (e.g. calculate) the location of a desired plane between the lateral malleolus and the medial malleolus. The desired plane can correspond to the sagittal plane containing the mechanical axis. The desired plane can vary, depending on factors such as the patient's specific anatomy and the surgeon's training and experience. For example, the desired plane can be located midway between the lateral malleolus and medial malleolus, or 55% toward the medial malleolus from the lateral malleolus, or at some other predetermined location.

The user can use one or more user inputs 28 to direct the surgical orientation device 14 to calculate the location of and/or orientation of the sagittal plane. Once the surgical orientation device 14 has calculated where the sagittal plane is, the surgical orientation device 14 can provide location feedback to the user, for example in the form of a visual signal or signals on the display 26, indicating that the location of the sagittal plane has been calculated.

Figure 2C:
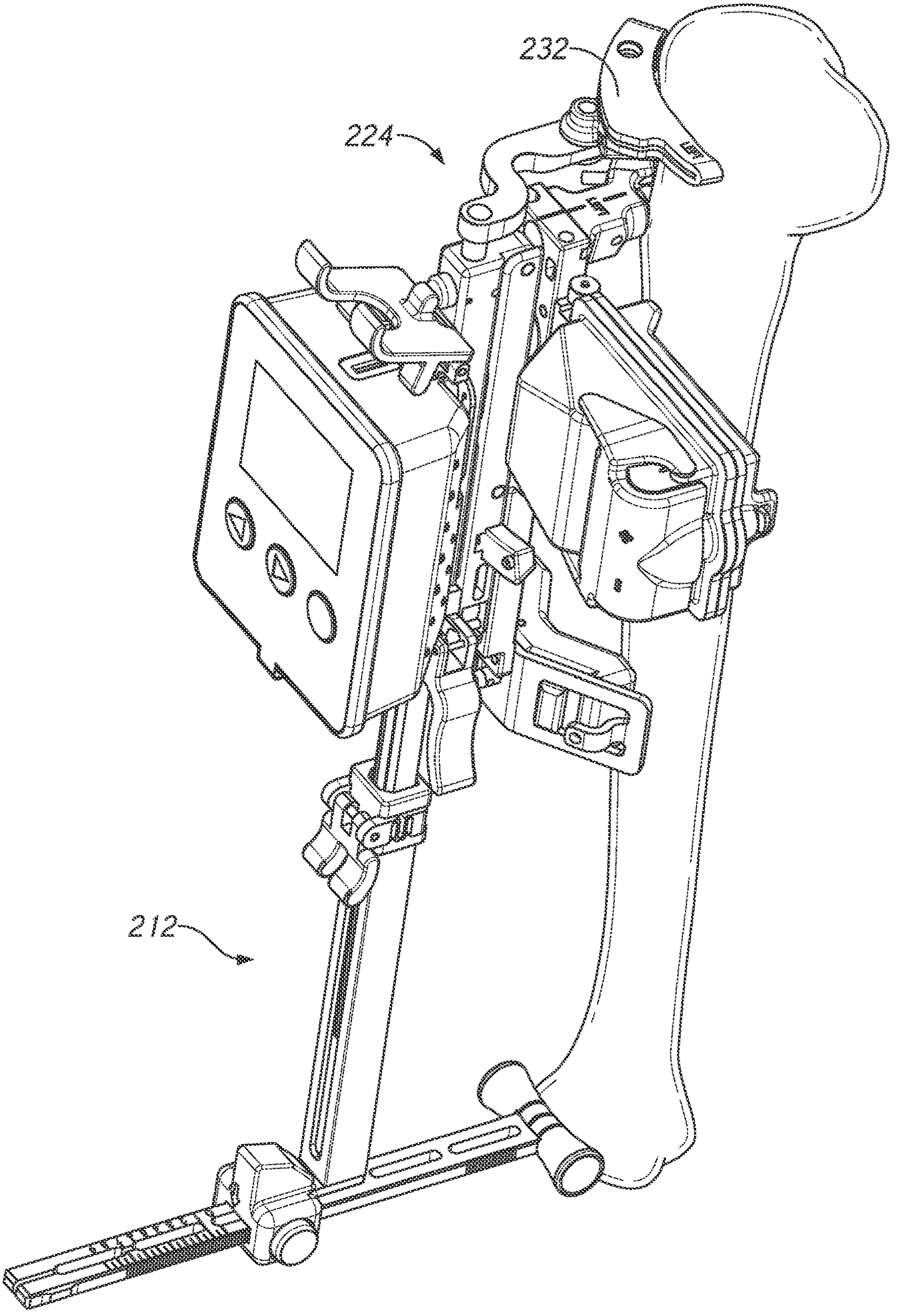

Referring to FIG. 2C, once the mechanical axis has been identified, the tibial cutting block assembly 224 can be utilized. The cutting block assembly 224 can be positioned such that the cutting block 232 is spaced away from anterior surface of the tibia. The surgical orientation device 14, and tibial assembly 212, can be used to adjust the cutting block 232 in order to obtain a desired orientation for resection of the top of the tibia. For example, a posterior slope assembly 216 and a varus/valgus assembly can each be independently adjusted to change the angle of the cutting block 232, and subsequently, the angle of the intended resection. During this adjustment, the surgical orientation device 14 can provide a reading or readings on its display 26 indicating whether the surgical orientation device 14 (and likewise the cutting block 232) is aligned with the sagittal plane and/or coronal plane containing the mechanical axis.

Once the cutting block is in position, the cutting block 232 can be mounted to an anterior surface of a proximal portion of the tibia by a plurality of pins. The surgical orientation device 14 can be removed, as can the tibial assembly 212. After the cutting block 232 has been mounted to the tibia, a proximal portion of the tibia can be resected.

B. Femoral Preparation and Knee Distraction System

FIGS. 3A-3E show an embodiment of a resection plane orienting system 310. The system 310 can be configured to distract the knee joint during a knee replacement procedure. The system 310 can be configured to distract the knee joint during a knee replacement procedure and measure the native or pre-surgical rotation of the femur relative to the tibial resection. The system 310 can additionally or alternatively be configured to facilitate attachment of a drill guide to the distal femur for alignment of locating holes in the distal femur for the implant's "4-in-1" cutting block. When the knee is sufficient distracted, the system 310 provides information about how to resect the femur in a way that helps to balance the soft tissue and/or ligaments within the knee joint. The system 310 can comprise the surgical orientation device 14 and the reference sensor device 16. As described herein, the surgical orientation device 14 and the reference sensor device 16 can be used for alignment, for distraction or for both alignment and distraction. The system 310 can further comprise one or both of a tibial system 312 and a femoral system 352, as described herein. While the tibial system 312 and a femoral system 352 are described as discrete subsystems, the system 310 can be considered one instrument. In some embodiments, the system 310 can be pre-connected on a surgical kit, e.g. implemented as an inseparable assembly.

1. Tibial System

Figure 4A:
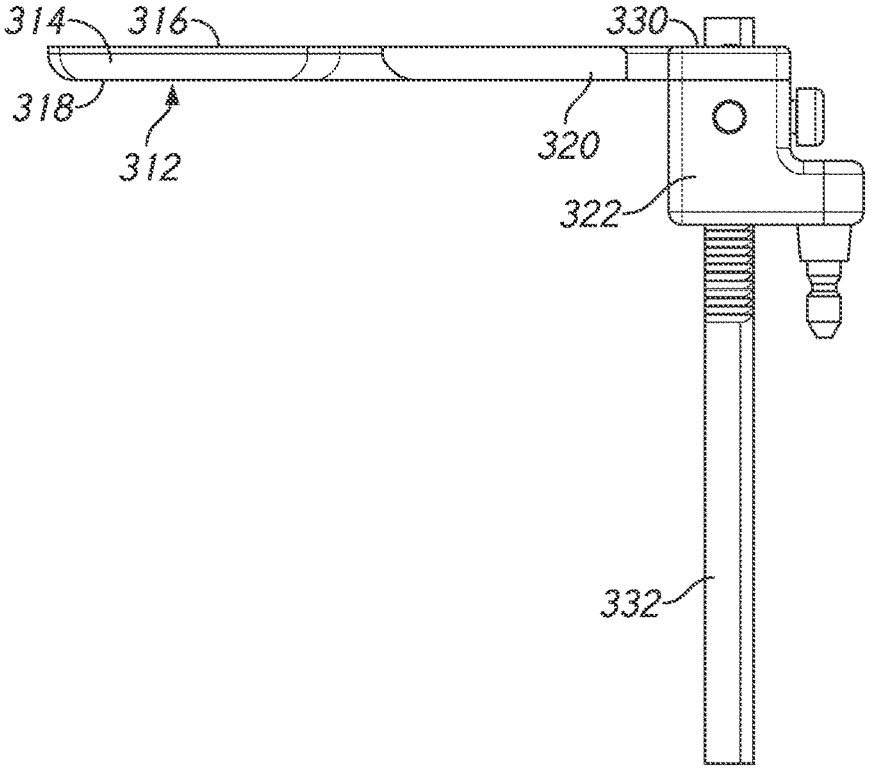
FIGS. 4A-4B illustrate views of a tibial system of the femoral preparation and knee distraction system of FIG. 3A.
Figure 4B:
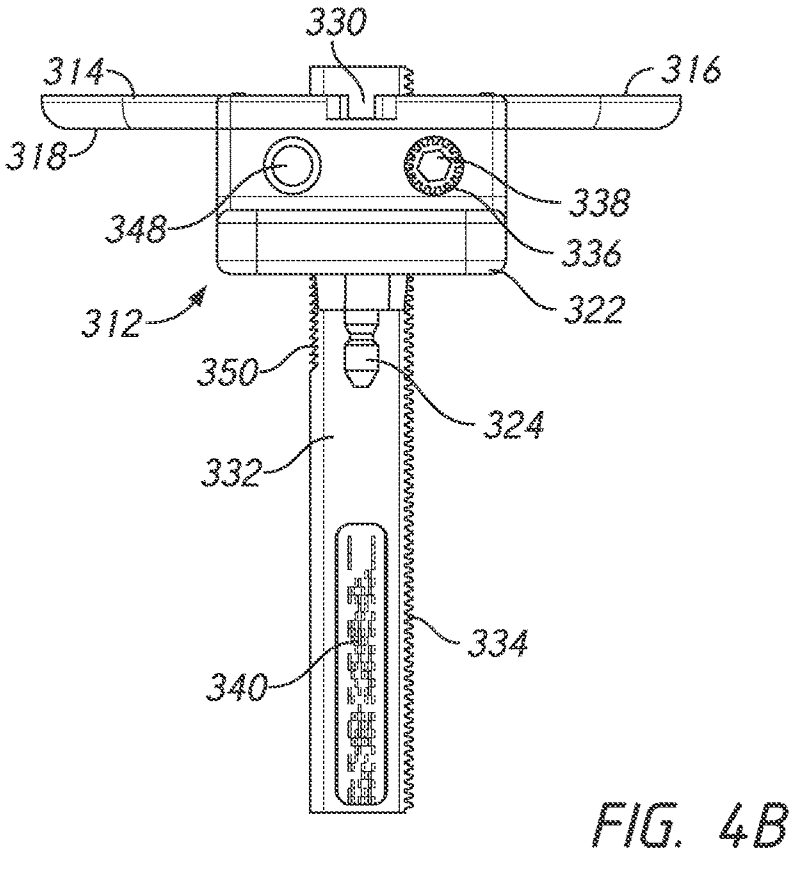

FIGS. 4A and 4B illustrate the tibial system 312. The tibial system 312 can include a tibial baseplate 314. The tibial baseplate 314 can be considered a reference feature. The tibial baseplate 314 can be configured to be positioned on a tibial plateau or on a resection plane formed on the proximal tibia. The tibial baseplate 314 can comprise a planar member. The tibial baseplate 314 can comprise a first surface 318 configured to align with the flat surface of the resected tibia. The tibial baseplate 314 can include a second surface 316, opposite the first surface 318 positioned toward the femur. The tibial system 312 can include an extension member 320. The tibial system 312 can include a mounting block 322. The extension member 320 can span between the mounting block 322 and the tibial baseplate 314. The extension member 320 can position the mounting block 322 away from, e.g., anteriorly of, the knee joint.

In some embodiments, the extension member 320 can be integrally or monolithically formed with the tibial baseplate 314. In some embodiments, the extension member 320 and the tibial baseplate 314 form a unitary structure. In some embodiments, the extension member 320 can be integrally or monolithically formed with the mounting block 322. In some embodiments, the extension member 320 and the mounting block 322 form a unitary structure. In some embodiments, one or more of the extension member 320, the tibial baseplate 314, and the mounting block 322 are separate components.

The mounting block 322 can include a first coupler 324. The first coupler 324 can be configured to couple with the surgical ordination device 14 and/or the reference sensor device 16. The first coupler 324 can include an elongate post. In some embodiments, the first coupler 324 can have a regular shape (e.g., cylindrical). In some embodiments, the first coupler 324 have an irregular shape (e.g., triangular, teardrop, elliptical, rectangular). The irregular shape may facilitate alignment of the reference sensor device 16 in one orientation relative to the mounting block 322. In the illustrated embodiment, the first coupler 324 is positioned on a bottom surface of the mounting block 322. In the illustrated embodiment, the first coupler 324 is positioned perpendicular to the tibial resection. In some methods of use, the tibial resection is the reference feature. In the illustrated embodiment, the first coupler 324 is positioned such that the longitudinal axis of the reference sensor device 16 aligns with the longitudinal axis of the tibia. The axis of the tibia can be perpendicular to the tibial resection. In the illustrated embodiment, the first coupler 324 is positioned such that the longitudinal axis of the reference sensor device 16 aligns with a mechanical axis associated with the knee joint, e.g., of the tibia or the leg.

In some embodiments, the mounting block 322 can include one or more additional couplers 326. The one or more additional couplers 326 can be identical to the first coupler 324. The one or more additional couplers 326 can be positioned on any surface of the mounting block 322. An additional coupler 326 can be positioned such that the longitudinal axis of the reference sensor device 16 is perpendicular to the longitudinal axis of the tibia. See FIG. 11B. An additional coupler 326 can be positioned such that the longitudinal axis of the reference sensor device 16 is perpendicular to the mechanical axis. An additional coupler 326 can be positioned perpendicular to the tibial resection plane. An additional coupler 326 can be positioned at any known angle from the tibia resection plane. One or more of the couplers 324, 326 can be parallel to the tibial resection plane. One or more of the couplers 324, 326 can be perpendicular to the tibial resection plane. The coupler 324 can arrange the reference sensor 16 perpendicular to the tibial resection plane. The couple 326 can arrange the reference sensor 16 parallel to the tibial resection plane. The orientation of the reference sensor 16 relative to the tibial resection plane can be an input in the system 310. The user can input the orientation of the reference sensor 16 as an input in the surgical orientation device 14. The couplers 324, 326 can work with different software versions that accommodate their arrangement. In some embodiments, the coupler 326 can be provided without also providing the coupler 324.

The mounting block 322 can include a guide portion 330. In some embodiments, the guide portion 330 can extend through the mounting block 322. In some embodiments, the guide portion 330 is a slot or other opening. The guide portion 330 can guide a post 332 through the mounting block 322. The guide portion 330 can be configured to allow the post 332 to slide through the mounting block 322. The post 332 can provide for movement of the femoral system 352 relative to the tibial system 312.

The system 310 can include an adjustment device 336. The adjustment device 336 can be positioned anywhere within the system 310. In the illustrated embodiment, the tibial system 312 can include the adjustment device 336. The adjustment device 336 is configured to translate the post 332 relative to the mounting block 322. The adjustment device 336 can include a gear. The post 332 can include a corresponding gear, screw, ramp, rack, etc. The adjustment device 336 can include a pinion. The post 332 can include a corresponding rack. In the illustrated embodiment, the adjustment device 336 is a drive pinion. The adjustment device 336 can include any mechanical feature configured to cause translation of the post 332. In some embodiments, the adjustment device 336 can be rotated to cause translational movement of the post 332. In some embodiments, the adjustment device 336 can be translated to cause translational movement of the post 332. Other adjustment devices are contemplated. The adjustment device 336 can include an interface 338. The interface 338 can allow the user to move the adjustment device 336. The interface 338 can include a knob. The interface 338 can include a recess. In the illustrated embodiment, the interface 338 is a hex recess. The interface 338 can allow rotation of the adjustment device 336 by the user.

FIGS. 4A and 4B illustrate the tibial system 312 and the post 332. FIGS. 5A-5D illustrates internal components of the tibial system 312 and the post 332. In some embodiments, the post 332 is substantially straight along its length. The post 332 can be translated by the adjustment device 336. The post 332 can include a rack 334. The rack 334 can extend along an edge of the post 332. The rack 334 can extend along the length of the post 332, or a portion thereof. The adjustment device 336 can be drive pinion. The adjustment device 336 can interact with the rack 334 such that rotation of the adjustment device 336 causes translation of the post 332. The adjustment device 336 can be free to rotate within the mounting block 332. The adjustment device 336 can be prevented from translation within the mounting block 332.

Figure 5A:
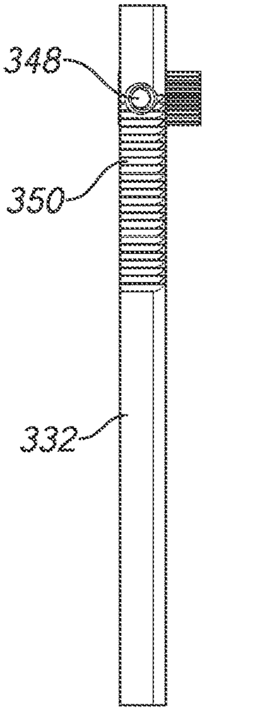
FIGS. 5A-5D illustrate views of an actuation system of the femoral preparation and knee distraction system of FIG. 3A.
Figure 5B:
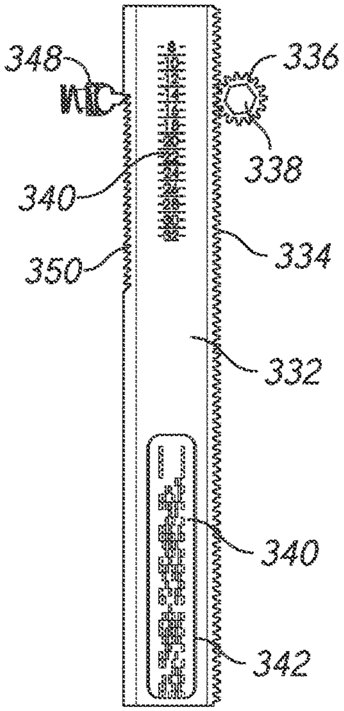
Figure 5C:
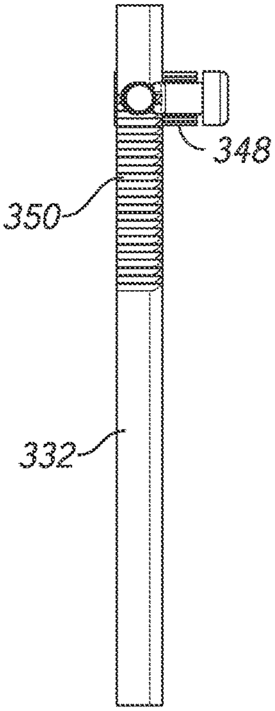
Figure 5D:
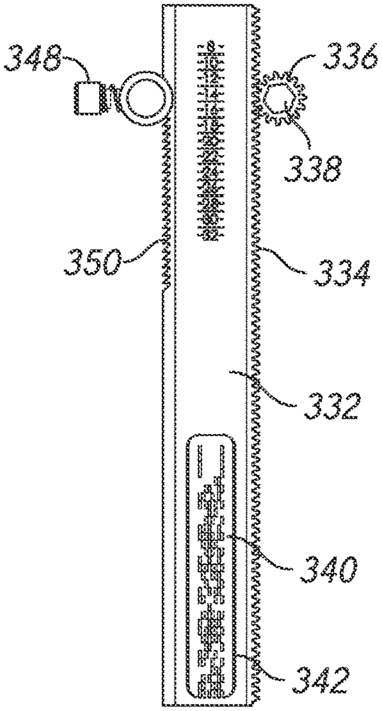

The post 332 can include one or more markings 340. The marking 340 can indicate length or extension of the post 332. The marking 340 can indicate a distraction distance of the system 310, as described herein. The marking 340 can include a scale. The marking 340 can include a machine readable scale. The marking 340 can include a scale visible to the user. The scale visible to the user is shown in FIGS. 4B, 5B and 5D. The scale extends beyond the mounting block 332. The user can view the scale to indicate the distraction distance. The mounting block 332 can include indicia, such as an arrow, to direct the user visually toward the measurement. As the post 332 translates upward, the numbers of the scale visible to the user increases (e.g., 8 mm, 9 mm, 10 mm, etc.). The distraction distance can correspond to the measurement visible to the user on the scale. In some embodiments, the marking 340 can be over a range of from about 0.5 inches to 3 inches, approximately 0-5 inches, etc. The marking 340 can be printed on the post 332. In some embodiments, the marking 340 can be on a separate component such as an inlay 342. The inlay 342 can be received within a portion of the post 332. In some embodiments, the inlay 342 is separated a distance from the distal end of the post 332. In some embodiments, the inlay 342 is separated a distance from the proximal end of the post 332.

Figure 3A:
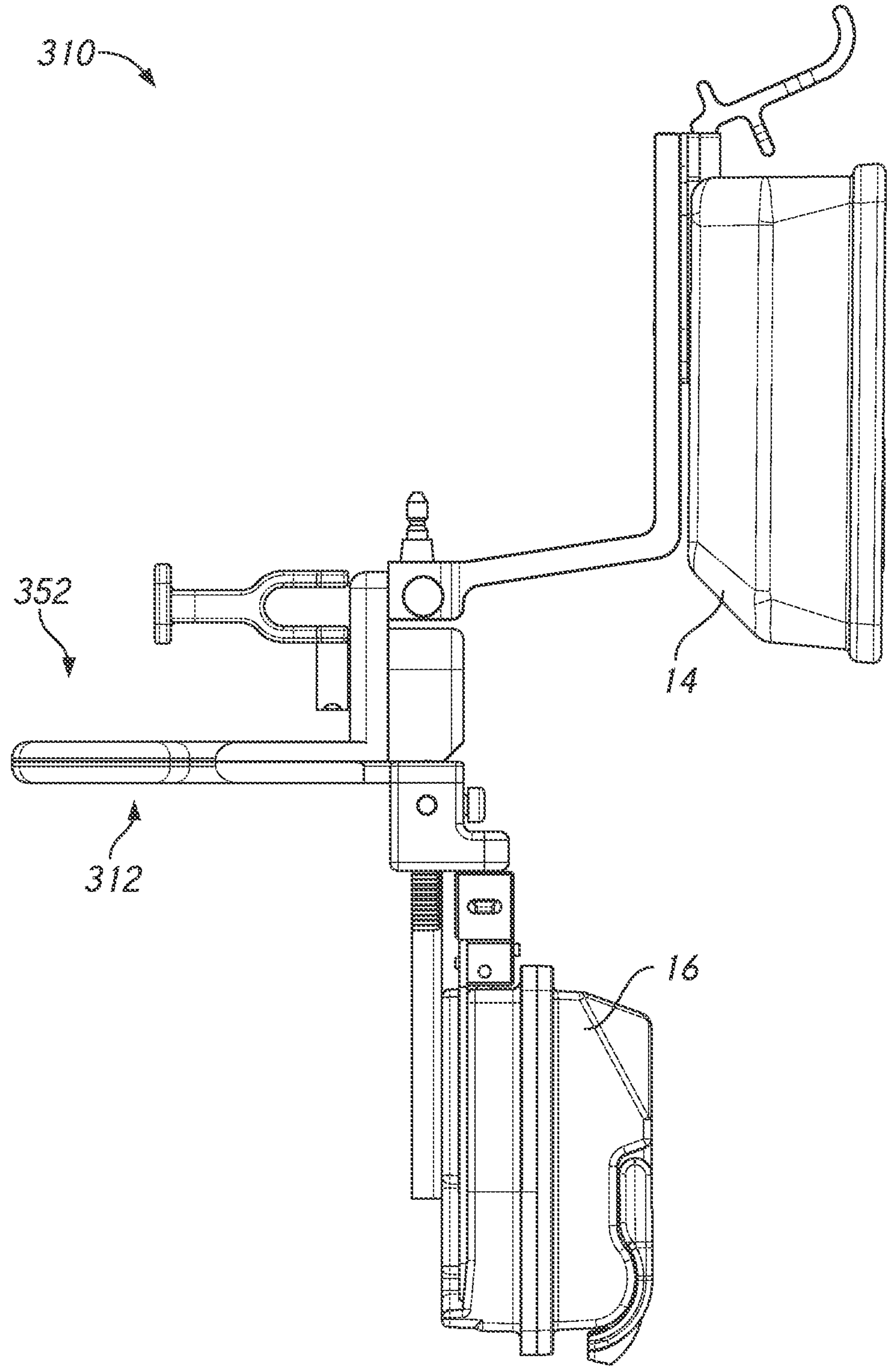
FIGS. 3A-3E illustrate views of a femoral preparation and knee distraction system.
Figure 3B:
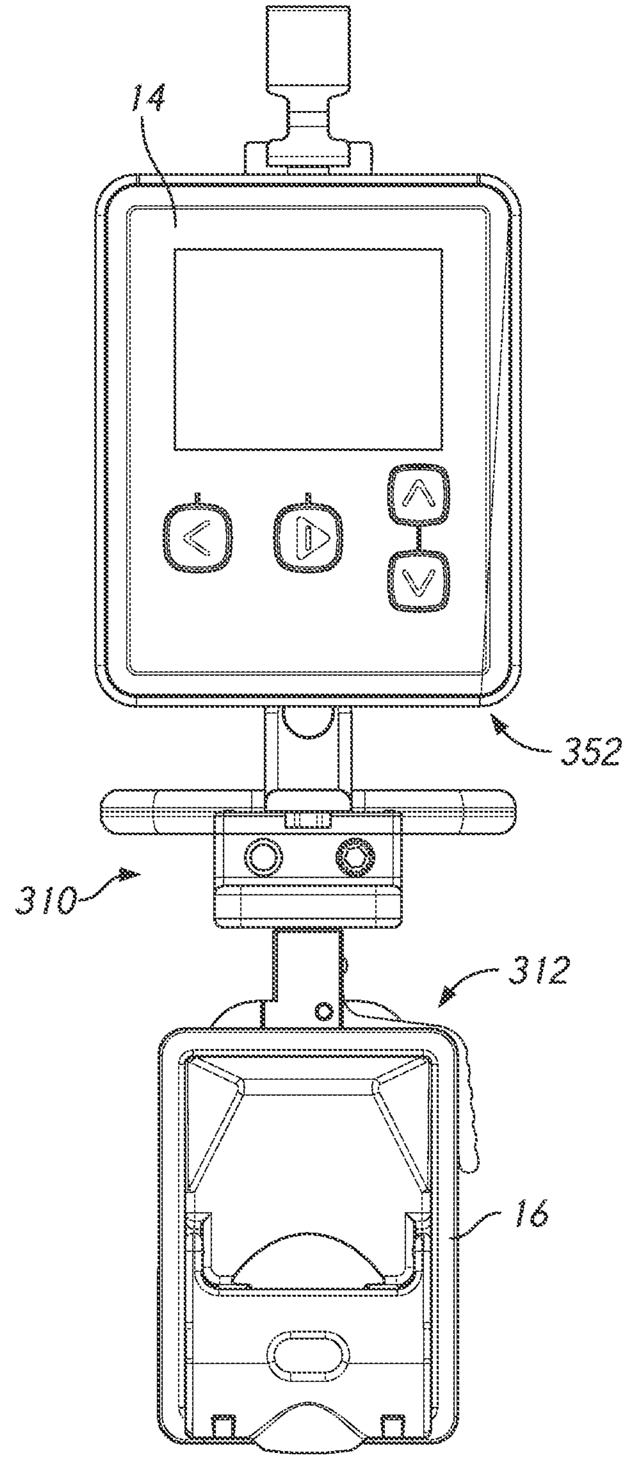
Figure 3C:
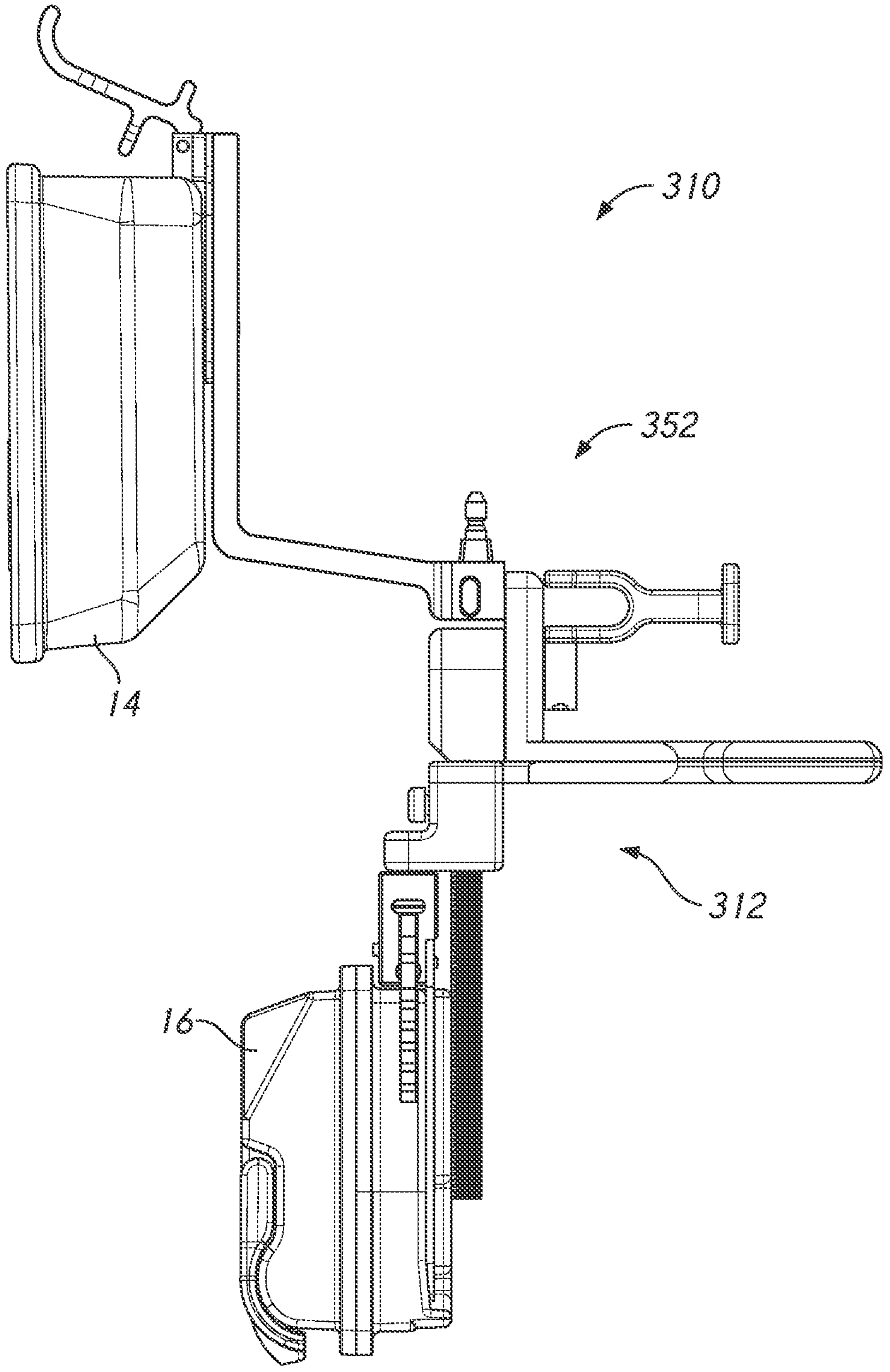
Figure 3D:
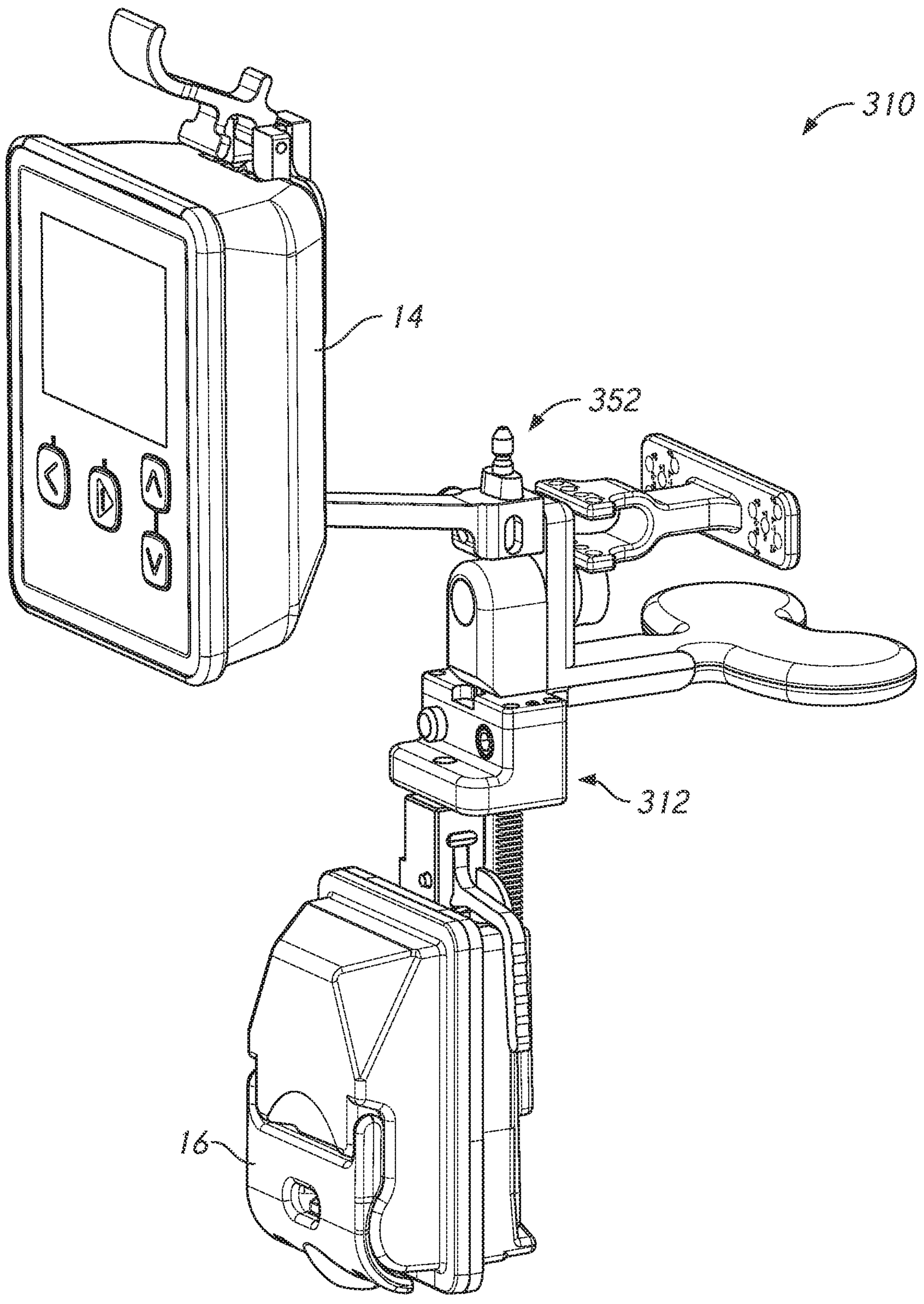

In some embodiments, the marking 340 can include a machine readable feature disposed on a surface of the post 332. In some embodiments, the machine readable feature comprises a binary code, a two dimensional bar code, or other symbol. In some embodiments, the reference sensor device 16 shown, in FIG. 3A, is configured to be positioned to read the markings 340. The reference sensor device 16 can be adapted to optically detect the machine readable feature of the markings 340. The markings 340 can include a binary code or other symbol that the reference sensor device 16 can read. The markings 340 can include a scale. In some embodiments, the scale can be read by the reference sensor device 16. In some embodiments, the scale is obstructed from the user. The distance indicated on markings 340 can be an input into the system 310 in any of the manners discussed herein (e.g., manual or sensed).

Figure 6A:
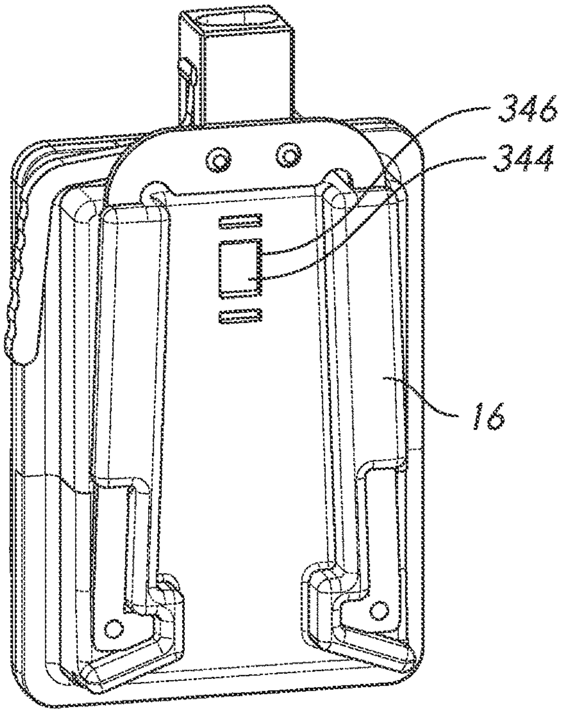
FIGS. 6A-6B illustrate views of a reference sensor device of the femoral preparation and knee distraction system of FIG. 3A.
Figure 6B:
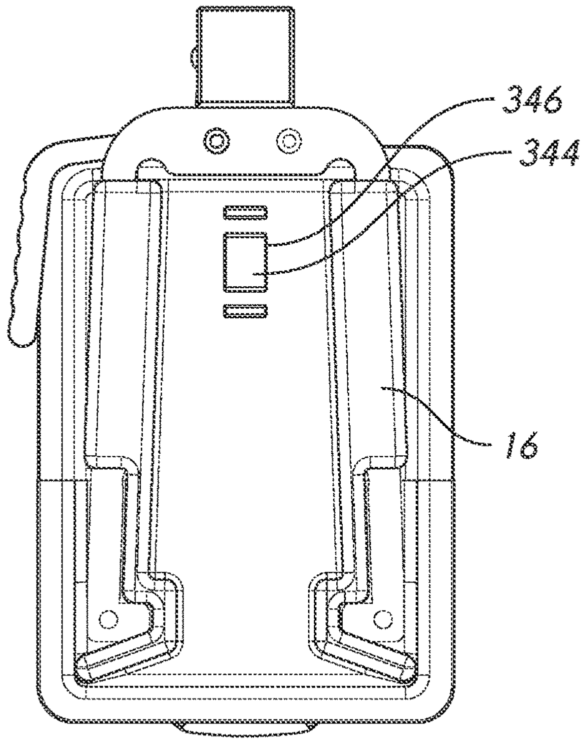

FIGS. 6A and 6B illustrate an embodiment of the reference sensor device 16. The reference sensor device 16 can includes a camera 344. In some embodiments, the camera 344 and the reference sensor device 16 are separate components. In some embodiments, the camera 344 and the reference sensor device 16 are coupled together. In some embodiments, the camera 344 is integrally formed with the reference sensor device 16. In some embodiments, the camera 344 is a separate component from the reference sensor device 16. The reference sensor device 16 can include a window 346 to enable the camera 344 to view there through. The camera 344 can capture images of the marking 340. In some embodiments, the camera 344 and/or the reference sensor device 16 can include a light to illuminate the marking 340. In some embodiments, the light is a LED. In some embodiments, the mounting block 322 includes a window to permit the camera 344 to capture images. In other embodiments, the camera 344 captures images of the marking 340 extending beyond the mounting block 322.

The image of the marking 340 can provide accurate determination of the translational position of the post 332. The marking 340 can be positioned on the post 332 adjacent to the camera 344 when the reference sensor device 16 is coupled to the mounting block 322. The camera 344 can be fixed relative to the mounting block 322 when the camera 344 captures images. The camera 344 can be oriented such that the camera 344 faces the marking 340. The camera 344 can capture an image of the markings 340. The image can correspond with a distraction distance. The distraction distance changes as the post 332 slides through the mounting block 322.

In some embodiments, the camera 344 can capture an image of a binary code of the marking 340. In some embodiments, the camera 344 can capture an image of a scale or other markings 340. The distraction distance can be based on images captured by the camera 344 of the marking 340, as described herein. In some embodiments, the image can be captured automatically by the camera 344. In some embodiments, the image can be captured by the camera 344 when prompted by the user (e.g., interaction with the user input 28).

In some embodiments, the system 310 can measure the distraction distance using one or more sensors. The reference sensor device 16 can include one or more inertial sensors capable of determining a distance measurement. The surgical orientation device 14 can include one or more inertial sensors capable of determining a distance measurement. In some embodiments, the system 310 can measure a reference distance from the surgical orientation device 14 and/or the reference sensor device 16. In some embodiments, the system 310 can record or store a reference distance from the surgical orientation device 14 and/or the reference sensor device 16. During distraction, the system 310 can measure changes in distance from the reference distance. The inertial sensor output can be used to measure distance in addition to or alternatively to the camera 344 reading the markings 340. The system 310 can perform one or more calculations to determine the distraction distance from the inertial sensor output.

Referring back to FIGS. 4A-5D, the system 310 can include a catch 348. The catch 348 can be positioned anywhere within the system 310. In the illustrated embodiment, the tibial system 312 can include the catch 348. The catch 348 is configured to maintain the position of the post 332 relative to the mounting block 322. The catch 348 can include a gear. The catch 348 can include a detent. The catch 348 can include a pin. The post 332 can include a corresponding gear, screw, ramp, rack or ratchet. The catch 348 can include any mechanical feature configured to limit movement of the post 332. In some embodiments, the catch 348 can include any mechanical feature configured to limit unidirectional movement of the post 332.

The post 332 can include a ratchet 350. The ratchet 350 can extend along the length of the post 332, or a portion thereof. The catch 348 can interact with the ratchet 350 such that translation of the post 332 can be limited. In some embodiments, when the catch 348 is engaged with the ratchet 350, the translation of the post 332 can be limited in both directions. When the catch 348 is disengaged with the ratchet 350, the post 332 can translate in both directions via the adjustment device 336. In some embodiments, the catch 348 can be engaged or disengaged by the user interacting with an interface, such as by turning a knob. In some embodiments, the catch 348 limits movement in only one direction. When the catch 348 is engaged with the ratchet 350, the translation of the post 332 can be limited to movement in one direction. In some embodiments, the one direction increases the distraction distance. When the catch 348 is disengaged with the ratchet 350, the post 332 can translate in both directions via the adjustment device 336.

In some embodiments, the catch 348 can include a spring. In some embodiments, the catch 348 can be biased into engagement with the ratchet 350. The user interacts with the interface to move the catch 348 away from the ratchet 350. In some embodiments, the catch 348 can be biased out of engagement with the ratchet 350. The user interacts with the interface to move the catch 348 toward the ratchet 350. Other configurations are contemplated.

In some embodiments, the movement of the post 332 can be tracked or monitored. For example, the system 310 can provide audible and/or visual feedback to the user, indicating the degree or extent to which the post 332 has been moved relative to an initial starting position. In some embodiments, a feedback system can be coupled to the post 332. In some embodiments, the catch 348 is the feedback system. In other embodiments, the system 310 can include another feedback system. In some embodiments, the user can hear and/or feel the catch 348 contacting the ratchet 350 as the post 332 moves up and/or down. This contact can produce an audible click, or clicks. This contact can additionally or alternatively provide a force (e.g. frictional) which can hold the post 332 in a desired position, until the adjustment device 336 is turned again.

2. Femoral System

Figure 7A:
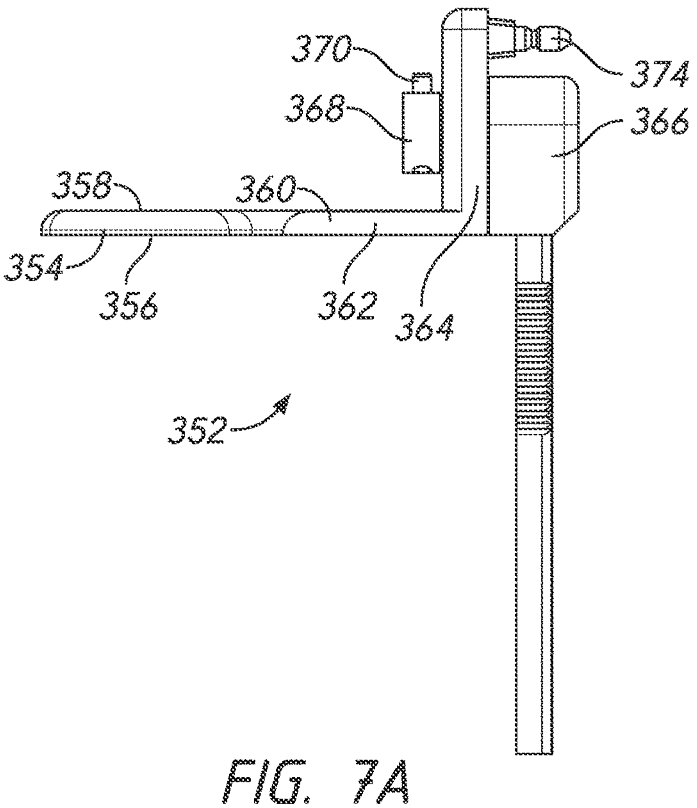
FIGS. 7A-7B illustrate views of a femoral system of the femoral preparation and knee distraction system of FIG. 3A.
Figure 7B:
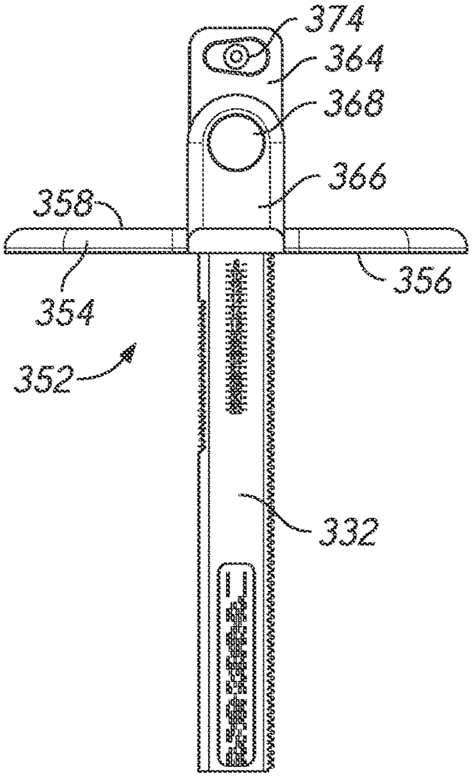

FIGS. 7A and 7B illustrate the femoral system 352. The femoral system 352 can include a femoral baseplate 354. In the illustrated embodiment, the femoral baseplate 354 can include one femoral baseplate 354. In some embodiments, the femoral baseplate 354 can include two or more femoral baseplates 354. In some embodiments, the femoral baseplate 354 is the femur contacting component. The femoral baseplate 354 can comprise a planar member. The femoral baseplate 354 can comprise a first surface 358 configured to be positioned relative to a portion of the femur. For example, the first surface 358 of the femoral baseplate 354 can be configured to engage the bottom of a bony landmark, such as for example a femoral condyle. The femoral baseplate 354 can include a second surface 356, opposite the first surface 358 positioned toward the tibia.

The femoral system 352 can include an extension member 360. In the illustrated embodiment, the extension member 360 is generally L-shaped. The extension member 360 can include a first portion 362 that extends from the femoral baseplate 354. The extension member 360 can include a second portion 364 that extends perpendicularly or generally perpendicularly from the first portion 362. Other configurations of the extension member 360 are contemplated. In some embodiments, the extension member 360 can be integrally or monolithically formed with the femoral baseplate 354. In some embodiments, the extension member 360 and the femoral baseplate 354 form a unitary structure. The rotation of the femoral baseplate 354 can cause corresponding rotation of the extension member 360 as described herein.

The femoral system 352 can include a post mount 366. The extension member 360 can span between the post mount 366 and the femoral baseplate 354. The extension member 360 can position the post mount 366 away from the knee joint. The femoral system 352 can include the post 332 described herein. In some embodiments, the post mount 366 can be coupled to the post 332. In some embodiments, the post mount 366 can be integrally or monolithically formed with the post 332. In some embodiments, the post mount 366 and the post 332 form a unitary structure. The translation of the post 332 can cause corresponding translation of the post mount 366 as described herein.

The post mount 366 can be coupled to the extension member 360. The post mount 366 can be coupled to the second portion 364 of the extension member 360. The post mount 366 can be mounted to allow rotation of the extension member 360 relative to the post mount 366. The post mount 366 can be mounted to allow rotation of the femoral baseplate 354 relative to the post 332. The femoral system 352 can include a rotational interface 368. The rotational interface 368 can be a pin. The extension member 360 can rotate about the rotational interface 368 relative to the tibial baseplate 314. The femoral baseplate 354 can rotate about the rotational interface 368 relative to the tibial baseplate 314. The rotational interface 368 can be positioned in the middle of the femur and/or tibia. The rotational interface 368 can be aligned with an anatomical feature, such as the intercondylar notch, Whiteside's Line, or the mechanical axis of the tibia.

The rotational interface 368 can include a mounting feature 370. The mounting feature 370 can allow one or more drill guides or other instruments to mount to the system 310. The mounting feature 370 can be parallel to the tibial baseplate 314. The mounting feature 370 can be coupled to the post 332. In some embodiments, the mounting feature 370 remains in position as the femoral baseplate 354 rotates. The mounting feature 370 can be decoupled from the rotation of the extension member 360. The mounting feature 370 can be decoupled from the rotation of the femoral baseplate 354.

The extension member 360 can include a second coupler 374. The second coupler 374 can be configured to couple with the surgical orientation device 14 and/or the reference sensor device 16. The second coupler 374 can include an elongate post. In some embodiments, the second coupler 374 can have a regular shape (e.g., cylindrical). In some embodiments, the second coupler 374 can have an irregular shape (e.g., triangular, teardrop, elliptical, rectangular). The irregular shape may facilitate alignment of the surgical orientation device 14 in one orientation relative to the extension member 360. In the illustrated embodiment, the second coupler 374 is positioned on a side surface of the second portion 364. In the illustrated embodiment, the second coupler 374 is positioned such that the longitudinal axis of the surgical orientation device 14 aligns with the femoral baseplate 354. As the femoral baseplate 354 rotates relative to the tibial baseplate 314, the surgical orientation device 14 rotates. As the femoral baseplate 354 translates relative to the tibial baseplate 314, the surgical orientation device 14 translate.

Referring back to FIG. 3E, the femoral system 352 can include a bracket 376. The second coupler 374 can be configured to couple with the bracket 376. The surgical orientation device 14 can be configured to couple with the bracket 376. The bracket 376 can include a third coupler 378. The third coupler 378 can be configured to couple with the surgical orientation device 14 and/or the reference sensor device 16. The third coupler 378 can have the same shape and/or configuration as the first coupler 324 and/or the second coupler 374. In the illustrated embodiment, the third coupler 378 is positioned on a side surface of the bracket 374.

In some method of use, the surgical orientation device 14 is coupled with the second coupler 374 and the reference sensor device 16 is coupled to the third coupler 378. The surgical orientation device 14 and reference sensor device 16 at a fixed angle and both coupled to the femur. The surgical orientation device 14 and the reference sensor device 16 can be calibrated relative to the femur. The surgical orientation device 14 and the reference sensor device 16 can be zeroed. The role of the third coupler 378 is to hold the surgical orientation device 14 and reference sensor device 16 at some known angle during calibration or zeroing. The user can move the reference sensor device 16 to the first coupler 324 described herein. The reference sensor device 16 is coupled to the tibia via the first coupler 324. Thereafter, the surgical orientation device 14 and/or the reference sensor device 16 can calculate changes in position and/or orientation relative to each other. The surgical orientation device 14 and/or the reference sensor device 16 calculate changes in angle relative to each other. The surgical orientation device 14 and/or the reference sensor device 16 can use gyro propagation to measure the coronal plane angle. The surgical orientation device 14 and/or the reference sensor device 16 can include software and/or hardware to perform the gyro propagation. The surgical orientation device 14 and/or the reference sensor device 16 can include one or more algorithms to calculate the angle of the surgical orientation device 14 as the surgical orientation device 14 rotates with the femoral baseplate 354.

Figure 3E:
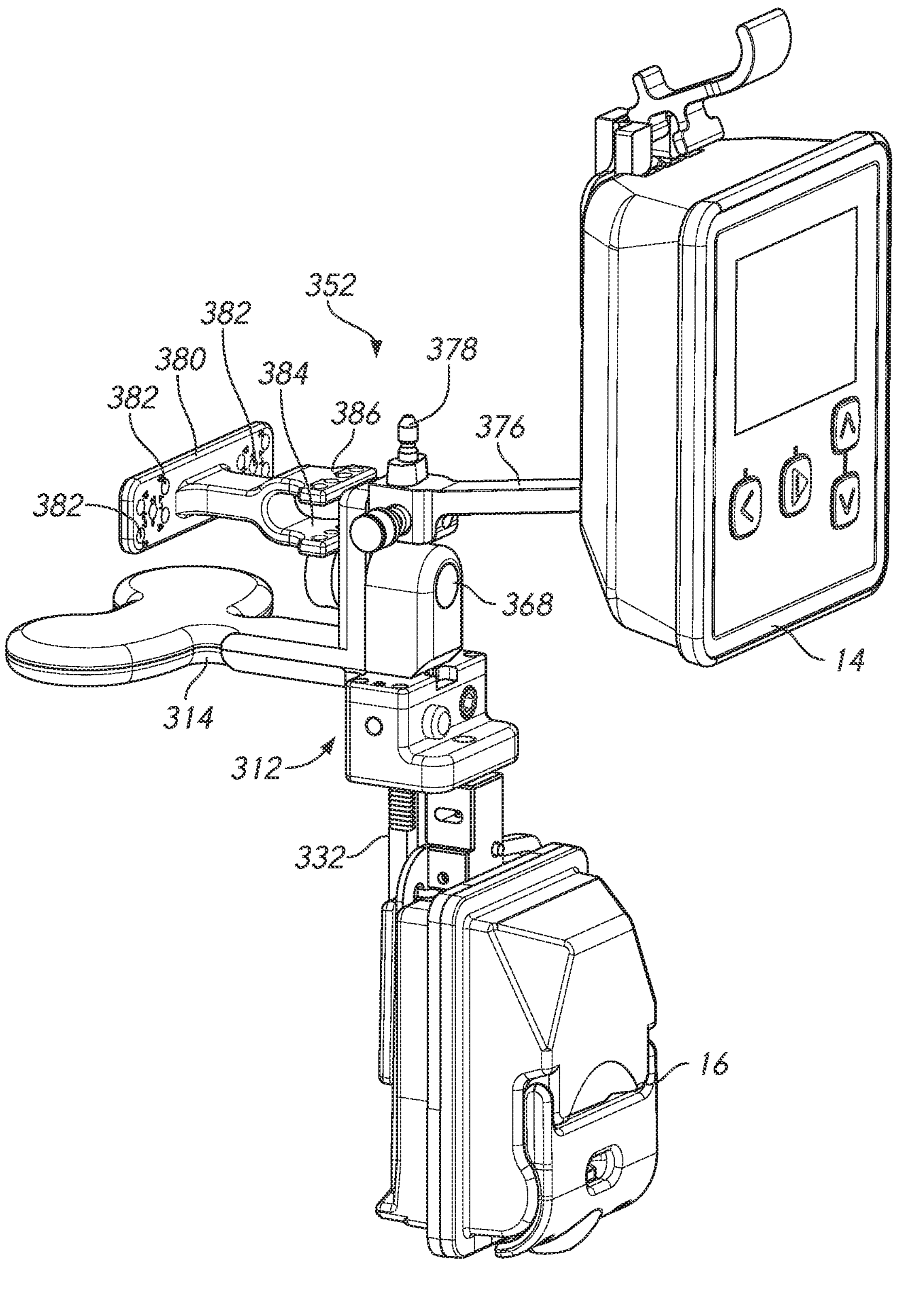
Figure 8A:
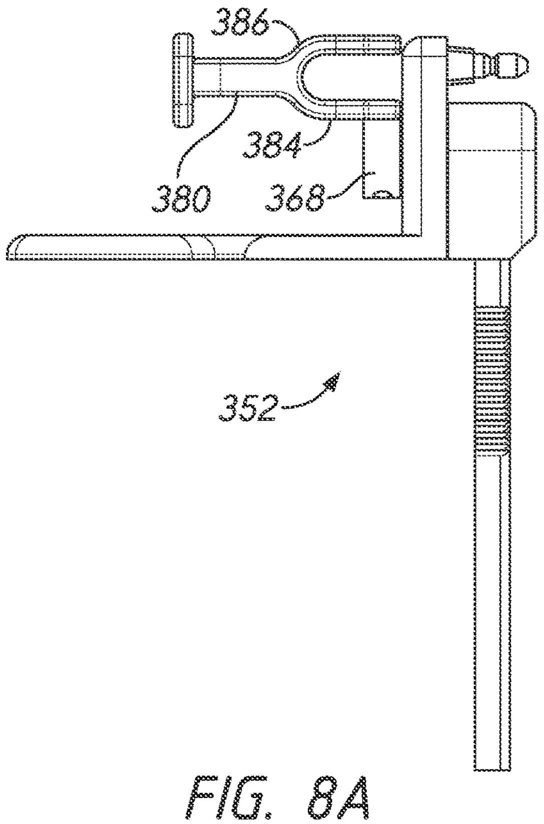
FIGS. 8A-8B illustrate views of a drill guide coupled with the femoral system of FIG. 7A-7B.
Figure 8B:
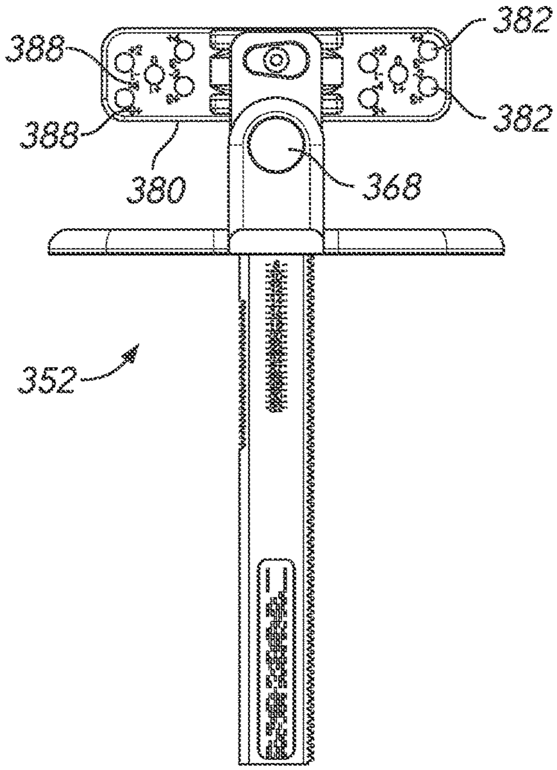

FIG. 3E shows a perspective view of the system 310. As shown in FIGS. 3E, 8A, and 8B, femoral system 352 can comprise a drill guide 380. The drill guide 380 can include one or more openings 382. The openings 382 can extend through the entire drill guide 380. While a plurality of openings 382, different numbers, sizes, shapes, and/or locations of openings 382 can also be used. The openings 382 can be used as guides for drills and/or pins. For example, when the system 310 has distracted a distal femoral condyle or condyles in a knee replacement procedure, a pin or pins (not shown) can be inserted into the distal femur in order to provide a mounting location for a cutting block (not shown). The openings 382 can be used as guides for insertion of these pins.

The openings 382 can be spaced apart from one another in a pattern or patterns. For example, some of the openings 382 along the bottom of the drill guide 380 can be spaced slightly higher, and/or further away from the tibial baseplate 314 than other openings along the bottom of the drill guide 380. Similarly, some of the openings 382 along the top of the drill guide 380 can be spaced slightly higher, and/or further away from the tibial baseplate 314 than other openings 382 along the top of the drill guide 380. In some embodiments, one or more parallel rows of openings 382 are provided. The rows can be parallel to the tibial baseplate 314. The one or more parallel rows of openings 382 can allow the user to adjust the gap, as described herein. The one or more parallel rows of openings 382 can allow the user to adjust the cutting block by a known distance. The one or more parallel rows of openings 382 can be used, for example, to control the orientation of a cutting block which is later attached to the pins.

In some embodiments, the drill guide 380 can have two orientations. The drill guide 380 can provide openings for even measurements (e.g., 2 mm, 4 mm, 6 mm, etc.). The drill guide 380 can be inverted for odd measurements (e.g., 1 mm, 3 mm, 5 mm, etc.). The drill guide 380 can include a first leg 384 and a second leg 386. The first leg 384 can couple with the mounting feature 370. The second leg 386 can couple with the mounting feature 370. In some embodiments, when the first leg 384 is coupled with the mounting feature 370, the user can utilize the even measurements. The first leg 384 is shown coupled to the mounting feature 370 in FIG. 8B. In some embodiments, when the second leg 386 is coupled with the mounting feature 370, the user can utilize the odd measurements. The drill guide 380 can include one or more markings 388. The marking 388 can indicate a value related to the opening 382. The marking 388 can indicate a distance measurement related to the opening 382. In FIG. 8B, the markings 388 for even measurements are inverted for the odd measurements. In some embodiments, each opening 382 has two markings 388. In some embodiments, each opening 382 has two markings 388 and only one is readable to the user. In some embodiments, each opening 382 has two markings 388 and one is inverted. In some embodiments, each opening has two markings 388 and only one is readable based on the orientation of the drill guide 380.

Referring to FIGS. 3E and 7A, the drill guide 380 can be a modular device that can be coupled or decoupled from the mounting features 370. In some embodiments, the mounting features 370 can be coupled to the rotational baseplate 368. In some embodiments, the rotational baseplate 368 is coupled to the post 332. In some embodiments, the post 332 is coupled to the tibial baseplate 314. In some embodiments, the drill guide 380 can be stabilized relative to the tibial baseplate 314. The drill guide 380 can be rotationally coupled to the tibial baseplate 314. The drill guide 380 can be parallel to the tibial baseplate 314. In some embodiments, the rotation of the femoral baseplate 354 is independent of the positioning of the drill guide 380. The system 310 can provide an alignment of the drill guide 380 relative to the tibial baseplate 314 as described herein.

In some embodiments, the system 310 can further comprise a spring or springs (not shown) which can apply a constant spring force to whatever anatomical structure or structures the femoral baseplate 354 are contacting. For example, the system 310 can include a pre-tensioned spring, such that when the system 310 is placed into an anatomical joint (e.g. a knee joint), the pre-tensioned springs can be released, and a pre-determined force can be applied by the femoral baseplate 354 to any contacted anatomical structures (e.g. condyles). In some embodiments, the force applied can be approximately 70-80 N. In other embodiments the force applied by can be approximately 60-90 N. Other forces and/or force ranges are also possible. The force applied by each spring can be different. In some embodiments, the system 310 does not include one or more springs applying the distraction force. The distraction force can be provided solely by the post 332 described herein. Possible disadvantages of springs include that the force is not constant over a range of distraction distance. The post 332 can provide a constant force over a range of distraction distances. Possible disadvantages of springs include that the force is not controlled and/or limited by the surgeon. Possible disadvantages to springs include that springs could more easily cause injury to ligaments. The posts 332 can provide a force that is controlled and/or limited by the user.

The system 310 described above can be biocompatible for short term exposure to the inner anatomy of the knee or other body joint, and can be sterilized by autoclave and/or gas. The system 310, or other similar distraction devices, can be used in joints other than the knee joint. For example, the system 310 can be used in the elbow, or other joint, to distract a joint.

3. Distraction Overview

Figure 9A:
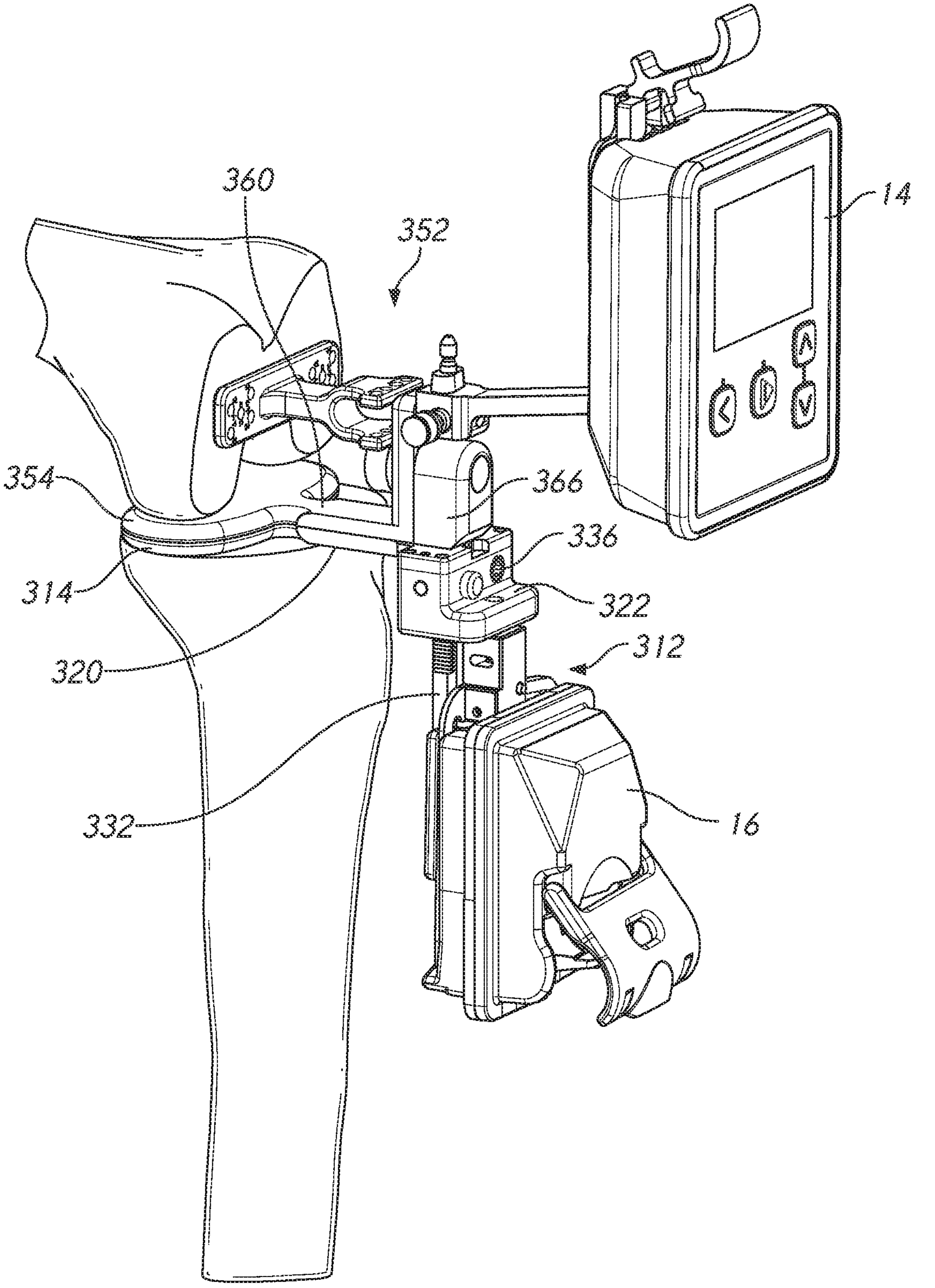
FIG. 9A illustrates the femoral preparation and knee distraction system of FIG. 3A disposed in a joint space between a femur and a tibia, with the femur and tibia placed in flexion.
Figure 9B:
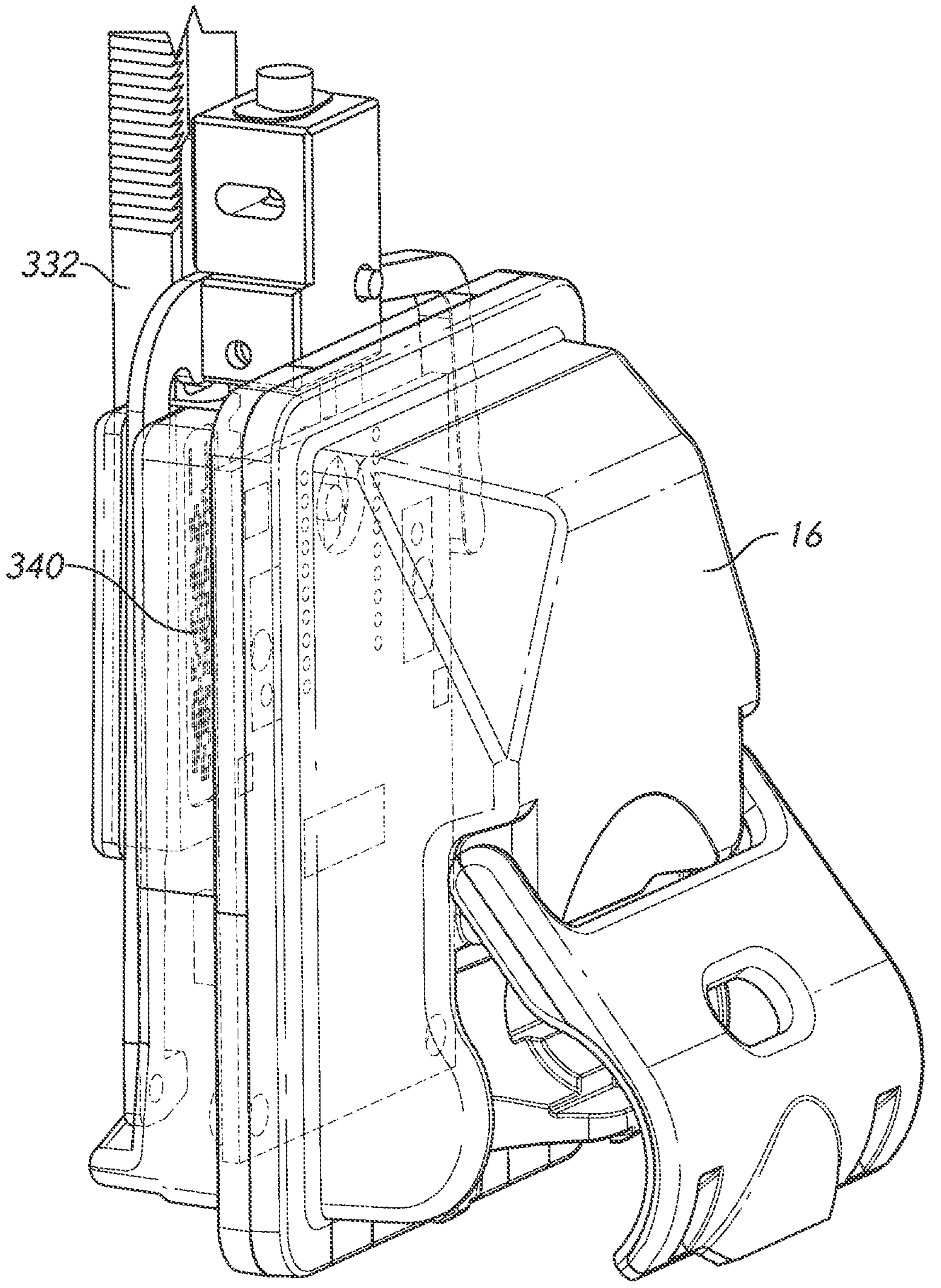
FIG. 9B illustrates a subsystem of the femoral preparation and knee distraction system of 9A including a reference device.
Figure 9C:
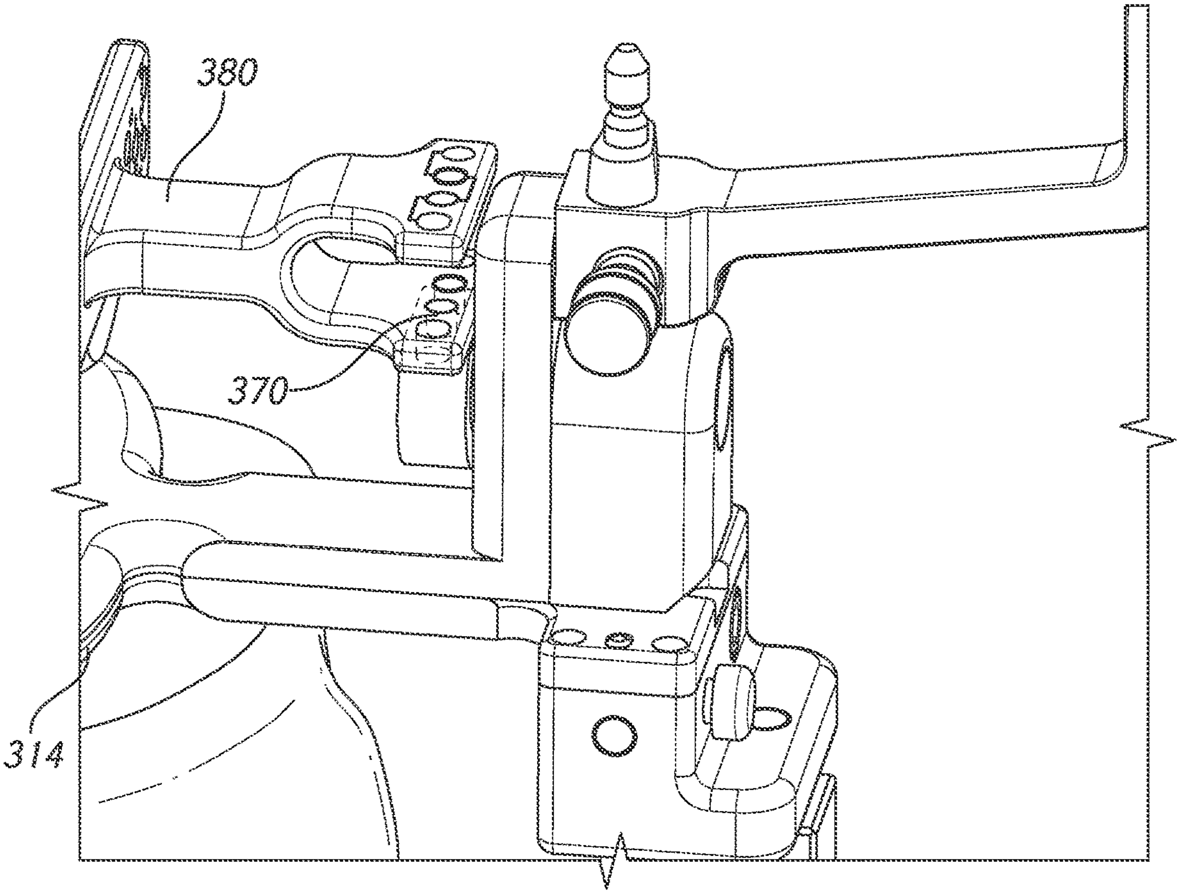
FIG. 9C illustrate a subsystem of the femoral preparation and knee distraction system of 9A including the drill guide.

FIG. 9A-9C illustrate additional views of the system 310 mounted on the tibia and femur of a patient. FIG. 9A illustrates an initial position of the system 310. FIGS. 9B and 9C illustrate subsystems of the system 310. In some embodiments, the tibial baseplate 314 can be adjacent to the femoral baseplate 354. In some embodiments, the extension 320 can be adjacent to the extension 360. In some embodiments, the post mount 366 can be adjacent to the mounting block 322. The surgical orientation device 14 can be coupled to the second coupler 374, see also FIG. 7A. The reference sensor device 16 can be coupled the first coupler 324, see also FIG. 4A. The reference sensor device 16 can be coupled the additional coupler 326, see also FIG. 11A. As noted herein, the first coupler 324, the second coupler 326 and/or the third coupler 378 can be aligned along the mechanical axis. The additional coupler 326 can be at some angle relative to the mechanical axis, such as perpendicular to the mechanical axis.

FIG. 9A illustrate how the tibial system 312 and the femoral system 352 can function together. The femoral system 352 can be moved up and down (e.g. proximally and distally) relative to the tibial baseplate 314 by the adjustment device or devices 336. The adjustment device 336 can be used to dictate and/or facilitate movement of the femoral system 352. The adjustment device 336 can include an interface 338 that allows the user to rotate the adjustment device 336, see FIG. 4A. The adjustment device 336 can be located within the mounting block 322. The mounting block 322 can provide stability to the post 332 as the post 332 translates there through. The adjustment device 336 and the post 332 can form a rack and pinion system as described herein.

The post 332 can span between the tibial system 312 and the femoral system 352. The post 332 can be coupled to the post mount 366 of the femoral system 352. The post mount 366 can be located on one side of the mounting block 322 and the post 332 can extend through the opposite side of the mounting block 322. The movement of the post 332 can cause corresponding movement of the femoral system 352 relative to the tibial system 312. The translation of the post 332 can cause corresponding translation of the femoral system 352 relative to the tibial system 312.

During distraction, the post 332 is translated within the guide portion 330 of the mounting block, 322. See FIG. 4A. As the post 332 is moved, the femoral system 354 moves as well. The post 332 can cause translation of the post mount 366 coupled thereto. The post mount 366 can cause translation of the extension member 360 and the femoral baseplate 354. The femoral system 352 translates as a unit with the post 332.

By translation of the post 332, the femoral baseplate 354 can be moved relative to the tibial baseplate 314 to increase or decrease a gap there between. The femoral baseplate 354 can be moved away from the tibial baseplate 314 (e.g. in a proximal direction). The femoral baseplate 354 can be moved towards the tibial baseplate 314 (e.g. in distal direction). The femoral baseplate 354 can be moved to increase the gap between the tibia and the femur.

For example, the femoral baseplate 354 can be moved in a vertically upwards (e.g. proximal) direction to apply pressure to the distal condyles of a femur or other bony structure in the body. The femoral baseplate 354 can move the condyles of the femur to a desired position. This movement can distract the knee joint, surrounding soft tissue, and/or ligaments. In some embodiments, a pressure or force gauge or gauges can be incorporated in the system 310 to determine the amount of compressive force which is applied by femoral baseplate 354 against the condyles of the femur.

In some embodiments, the femoral baseplate 354 can be rotationally coupled to the post mount 366. The femoral baseplate 354 can adjust relative to the patient's anatomy. For example, the femoral baseplate 354 can rotate relative to the plane containing the tibial baseplate 314. In a preferred arrangement, the femoral baseplate 354 can rotate in one or more directions about the post mount 366. This rotation can facilitate use of the system 310 in knee joints which vary in size, and where for example the femoral condyles in a particular knee joint are spaced significantly far apart. This rotation can also allow the femoral baseplate 354 to be inserted through a relatively narrow incision in the body and then rotate once inside the knee joint to engage the femoral condyles.

Referring to FIG. 9B, the system 310 can include the marking 340 which indicates the distance the post 332 has moved. In some embodiments, the marking 340 is a scale which is visible to the user. In some embodiments, the marking 340 is captured by the camera 344. The post 322, or a portion thereof, that extends beyond the mounting block 322 can include the marking 340. The marking 340 can align with the camera 344 of the reference sensor device 16. The camera 344 can capture an image of the marking 340. The marking 340 can be a distraction distance between the tibial baseplate 314 and the femoral baseplate 354.

In some embodiments, when the system 310 is being used to distract the knee joint, a ligament or ligaments can be released on either or both sides of the knee. The user can modify the ligament(s) of the knee to provide a desired balance of forces around the knee joint.

Referring to FIGS. 9A and 9C, the system 310 can include a drill guide 380 for one or more femoral cuts. In some methods of use, the user can make femoral cuts after distraction. As described herein, the drill guide 380 can be a modular device that can be coupled or decoupled from the mounting features 370, which are shown in FIG. 9C. In some embodiments, the drill guide 380 can be stabilized relative to the tibial baseplate 314. The drill guide 380 can be parallel to the tibial baseplate 314. In some embodiments, the drill guide 380 allows the user to place one or more pins that can aid in mounting a cutting block configured to make one or more cuts in the femur at an angle selected relative to (e.g., parallel to) the tibial baseplate 314.

Figure 10:
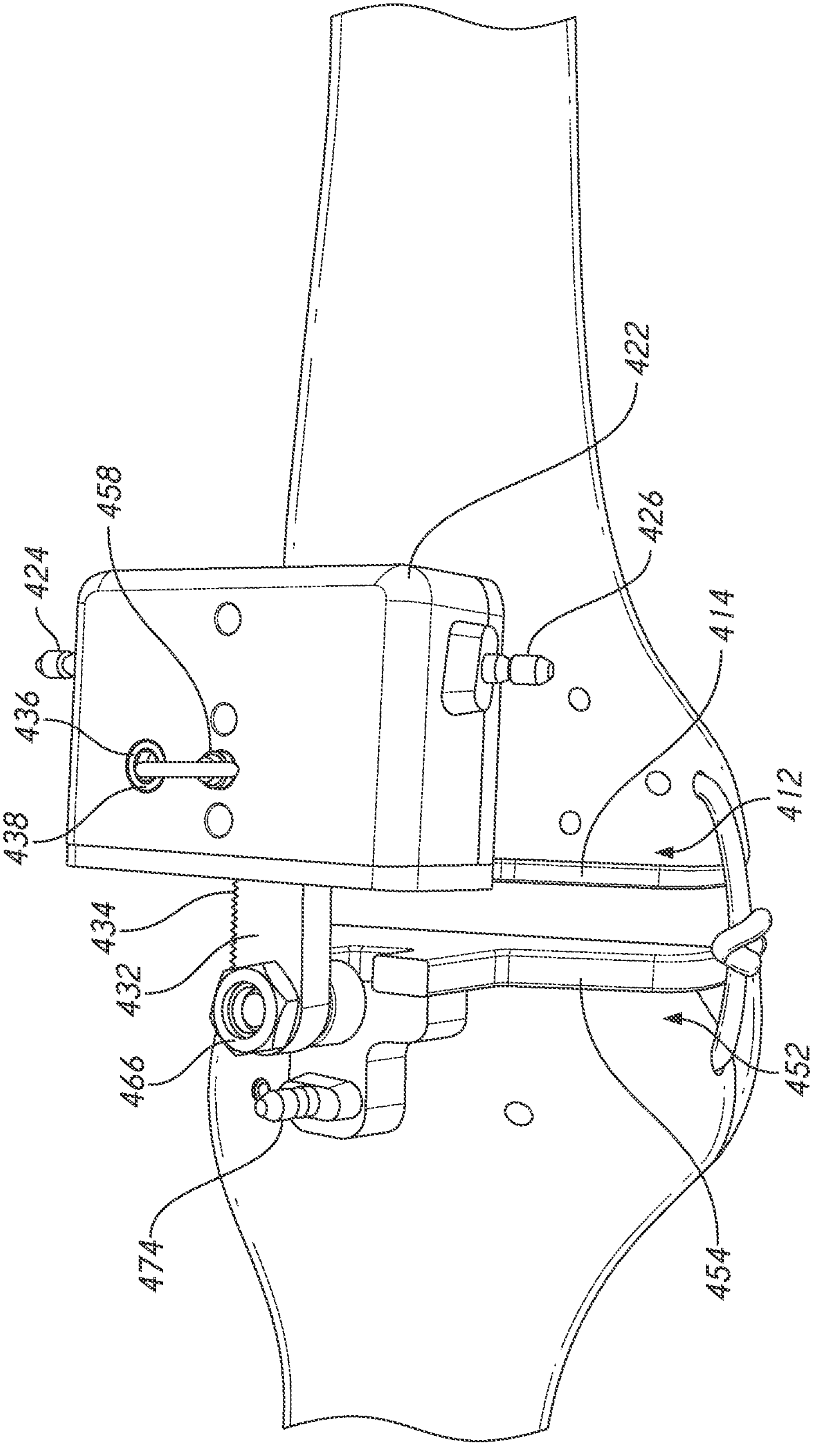
FIG. 10 is a view of another embodiment of a femoral preparation and knee distraction system.

FIG. 10 is an embodiment of a system 410. The system 410 can include any of the features of the system 310 described herein. The system 410 can include a tibial system 412, a tibial baseplate 414, a mounting block 422, a first coupler 424, an additional coupler 426, a post 432, a rack 434, an adjustment device 436, an interface 438, a femoral system 452, a femoral baseplate 454, a catch 458, a post mount 466, a second coupler 474, as shown in FIG. 10. FIG. 10 also shows the system 410 in use with a knee in extension. The system 310 can be used when the knee is in extension, as described herein. The catch 458 is shown with a knob. The user can rotate the knob to limit the movement of the post 432.

4. Distraction in Extension

During a knee joint replacement procedure, the system 310 described above can be used to align and balance the ligamentous structure of the knee joint and/or determine an orientation for a cut or cuts along the femur. The system 410 could be used as well, but for compact description the discussion distraction in extension will be presented in connection with the system 310.

In some methods of use, the proximal (i.e. upper) tibia can be cut. In some methods of use, the tibia is resected prior to using the system 310 and/or prior to resecting the femur. For example, and as described above, a tibial preparation system 210 or other tibial preparation system can be used to resect a portion or portions of the tibia, such that the proximal end of the tibia comprises generally a flat plane or plateau. Based on pre-operative determinations of desired varus/valgus, posterior/anterior, and/or other angles for this tibial resection plane, the plateau can be perpendicular to the mechanical axis, or at an angle other than perpendicular to the mechanical axis.

In some methods of use, the femur can be cut. In some methods of use, the femur is resected prior to using the system 310. For example, and as described above, a femoral preparation system 10 or other femur preparation system can be used to resect a portion or portions of the femur, such that the distal end of the femur comprises generally a flat plane. Based on pre-operative determinations of desired varus/valgus, posterior/anterior, and/or other angles for this femur resection plane, the resection can be perpendicular to the mechanical axis, or at an angle other than perpendicular to the mechanical axis. In some techniques, this cut is referred to as the distal femoral cut (DFC). The DFC removes a distal (i.e., lower) portion of the femur.

In some methods of use, the leg is positioned in full extension (not shown). The tibial baseplate 314 and the femoral baseplate 354 can be inserted into the knee joint. The tibial baseplate 314 can be positioned on the tibial plateau. The femoral baseplate 354 can be positioned above the tibial plateau. In some embodiments, the femoral baseplate 354 is positioned underneath the femoral resection. In some embodiments, the femoral baseplate 354 is positioned underneath the femoral condyles. Once the tibial baseplate 314 and the femoral baseplate 354 are inserted into the knee joint, the femoral baseplate 354 can be moved by turning the adjustment devices 336. For example, the femoral baseplate 354 can be moved away from the tibial baseplate 314. In some embodiments, the femoral baseplate 354 moves into contact with distal aspects of the femoral condyles. In some embodiments, the femoral baseplate 354 moves into contact with resected femur. The movement causes the system 310 to apply an opposing force or forces to the proximal tibia and the distal femur. This force can distract the knee joint and the surrounding soft tissue and/or ligaments. The femoral baseplate 354 can apply a different amount of pressure or force to each femoral condyle. The femoral baseplate 354 can apply the same amount of pressure or force to each femoral condyle. In some methods of use, the femoral baseplate 354 can rotate to provide equal force or pressure to each femoral condyle. In some embodiments, the tibial baseplate 314 can remain stationary while the femoral baseplate 354 is translated and/or rotated.

In some methods of use, the user can distract the knee joint. The user can apply a force until the femur is held in tension. The user can have a visual indication of the gap as the gap increases. In some methods of use, the user can also have a visual indication that a gap, or distance, between one femoral condyle and the tibial plateau is substantially identical to the gap, or distance, between the other femoral condyle and the tibial resection. In some methods of use, the user can also have a visual indication that a gap, or distance, between the femoral resection and the tibial resection is substantially rectangular. In some methods of use, the user can also have a visual indication that the femoral resection is parallel to the tibial resection.

In some embodiments, the user can release one or more ligaments in the knee joint prior to or during the knee distraction in order to facilitate simultaneous symmetry of the gaps, mechanical axis alignment, and/or balancing of the soft tissue and/or ligaments in the knee joint. In some methods of use, the user can modify the soft tissue to align the femoral baseplate 354 and the tibial baseplate 314. The user can nick or cut soft tissue to adjust for laxity of the knee joint. The user performs soft tissue balancing until the femoral baseplate 354 and the tibial baseplate 314 are parallel or approximately parallel. The user can release ligaments when the knee is in extension based on the angle output of the surgical orientation device 14. In some embodiments, the user releases soft tissue until the angle measurement is zero. The zero angle measurement indicates that the femoral baseplate 354 is parallel to the tibial baseplate 314.

The surgical orientation device 14 and/or the reference device 16 can be configured to measure rotation which is related to the relative tension in the medial and lateral soft tissue on the medial and/or lateral sides of the knee joint. In some embodiments, the adjustment device 336 is calibrated such rotation of the interface 338 corresponds to a resulting force. For example, each rotation can correspond to a pre-determined amount of force or pressure on the femoral baseplate 354. In some embodiments, the system 310 can calculate the force from the distraction distance. In some embodiments, the system 310 can calculate the force from the area of the femoral baseplate 354 and/or the tibial baseplate 314. In some embodiments, the system 310 can comprise sensors, or other structures, which can relay information to the surgical orientation device 14 and/or the reference sensor device 16 about the degree of force being exerted upon the femoral baseplate 354. In some embodiments, the system 310 can comprise sensors, or other structures, which can relay information to the surgical orientation device 14 and/or the reference sensor device 16 about the degree of force being exerted upon the tibial baseplate 314.

The surgical orientation device 14 can be configured to display the femur rotation. The femur rotation is detected by the surgical orientation device 14 when the soft tissue is tensioned. The surgical orientation device 14 can be configured to display the rotation of the femoral baseplate 354 relative to the tibia baseplate 314 when the knee is tensioned. The surgical orientation device 14 can display this information, for example, on the visual display located within the surgical field. If the tension, pressure and/or force applied to the soft tissue is too great, the user can change the tension by adjusting (e.g. turning) one or more of the adjustment members 336.

The surgical orientation device 14 and/or the reference device 16 can be configured to measure the distraction distance between the femoral baseplate 354 and the tibial baseplate 314. As described herein, the camera 344 can capture an image corresponding to the distraction distance. The camera 344 can capture an image of the marking 340. The image can correspond with a distance translated by the post 332 during distraction. The distance changes as the post 332 slides through mounting block 322. While the femoral baseplate 354 is being moved and/or rotationally adjusted, and the knee joint is being distracted, the camera 344 can capture an image corresponding to the distraction distance. The image can correspond to the distraction distance between the femoral baseplate 354 and the tibial baseplate 314.

In some methods, the surgical orientation device 14 and/or the reference device 16 converts the image of the camera 344 into a distraction distance. In some methods, the surgical orientation device 14 and/or the reference device 16 converts the image of the camera 344 into an extension measurement of the post 332. In some embodiments, the surgeon will enter an input (e.g., depress a button, interact with user input 28) to collect data from the reference device 16. In some methods, the surgeon will enter an input (e.g., depress a button) to collect data from the camera 344. In some embodiments, the surgeon will enter an input (e.g., depress a button) to collect data from the reference device 16 and the camera 344 simultaneously. In some methods, the reference device 16 and/or the camera 344 will only send data to the surgical orientation device 14 if the reference device 16 is stable or non-moving.

The surgical orientation device 14 can be configured to display information during distraction. The surgical orientation device 14 can display information in real-time. The surgical orientation device 14 can display information as data from the reference device 16 and/or the camera 344 is acquired. The surgical orientation device 14 can display the distraction distance of the femur and the tibia. The information can be a measured distance (e.g., 1 mm, 2 mm, 3 mm, 4 mm, 5 mm, 6 mm, 7 mm, 8 mm, 9 mm, 10 mm, etc.). The information can be any visual indicator (e.g., a bullseye, target, or sliding scale). The surgical orientation device 14 can display this information, for example, on the display 26 located within the surgical field.

The surgical orientation device 14 and/or the reference sensor device 16 can store any data related to the distraction. The surgical orientation device 14 and/or the reference sensor device 16 can be configured to store the distraction distance of the femur and the tibia when the leg is in extension. The surgical orientation device 14 and/or the reference sensor device 16 can be configured to store the extension gap when the leg is in extension. The surgical orientation device 14 and/or the reference sensor device 16 can store the distraction distance in extension for a later comparison to the leg in flexion. The surgical orientation device 14 and/or the reference sensor device 16 can store the distraction distance for post-operative use.

In some methods of use, the femur is resected prior to placing the leg in extension. The system 310 can measure angles relative to the tibia resection. In some methods of use, the femur is resected using the femoral preparation system 10 described herein. The femoral preparation system 10 can position a cutting block at a specific angle relative to the mechanical axis of the femur.

5. Distraction in Flexion

Figure 11A:
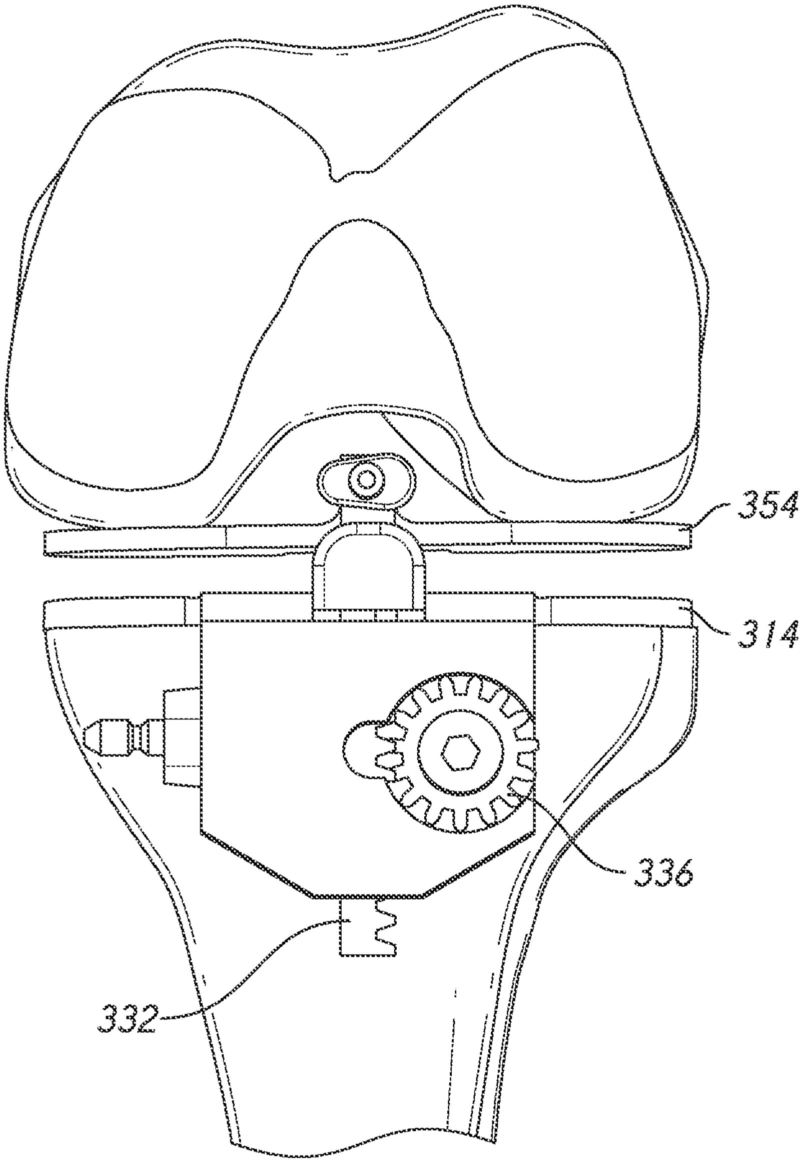
FIGS. 11A-11F are views of a femoral preparation and knee distraction system for soft tissue balancing, illustrating one method of using the system.

In some knee joint procedures, another cut which can be made is a posterior femoral cut (PFC). In preparation for the posterior femoral cut, the leg can be placed in approximately 90 degrees of flexion as shown in FIG. 11A. FIG. 11A shows the leg in flexion, with the tibial baseplate 314 and the femoral baseplate 354 inside the knee joint.

In some methods of use, the proximal (i.e. upper) tibia can be cut as shown in FIG. 11A. The tibial preparation system 210 or other tibial preparation system can be used to resect a portion or portions of the tibia, such that the proximal end of the tibia comprises generally a flat plane or plateau. In some methods of use, the femur can be cut as shown in FIG. 11A. In some embodiments, femoral preparation system 10 or other femur preparation system can be used to resect a portion or portions of the femur, such that the proximal end of the femur comprises generally a flat plane or plateau. In some embodiments, the femur is resected after distraction in extension.

In some methods of use, after completing the tibial resection and the distal femoral resection, the user flexes the knee to 90 degrees and inserts the system 310. In some methods of use, the leg is positioned in flexion. The tibial baseplate 314 and the femoral baseplate 354 can be inserted into the knee joint. The tibial baseplate 314 can be positioned on the tibial plateau. The femoral baseplate 354 can be positioned above the tibial plateau. In some embodiments, the femoral baseplate 354 is positioned underneath the femoral condyles as shown in FIG. 11A.

Once the tibial baseplate 314 and the femoral baseplate 354 are inserted into the knee joint, the femoral baseplate 354 can be moved by turning the adjustment device 336. As described herein, the adjustment device 336 can be rotated to move the femoral baseplate 354 away from the tibial baseplate 314, thereby distracting the knee joint. The adjustment devices 336 can cause translation of the post 332. The post 332 can be coupled to the femoral baseplate 354, such that translation of the post 322 causes translation of the femoral baseplate 354. The femoral baseplate 354 can be moved away from the tibial baseplate 314 as shown in FIG. 11A. In some embodiments, the femoral baseplate 354 moves into contact with posterior aspects of the femoral condyles. The movement causes the system 310 to apply an opposing force or forces to the proximal tibia and the distal femur. This force can distract the knee joint and the surrounding soft tissue and/or ligaments. The system 310 can apply individual opposing force or forces to the tibial plateau and the femoral condyles. Each condyle can be distracted individually, simultaneously, and/or consecutively.

Figure 11B:
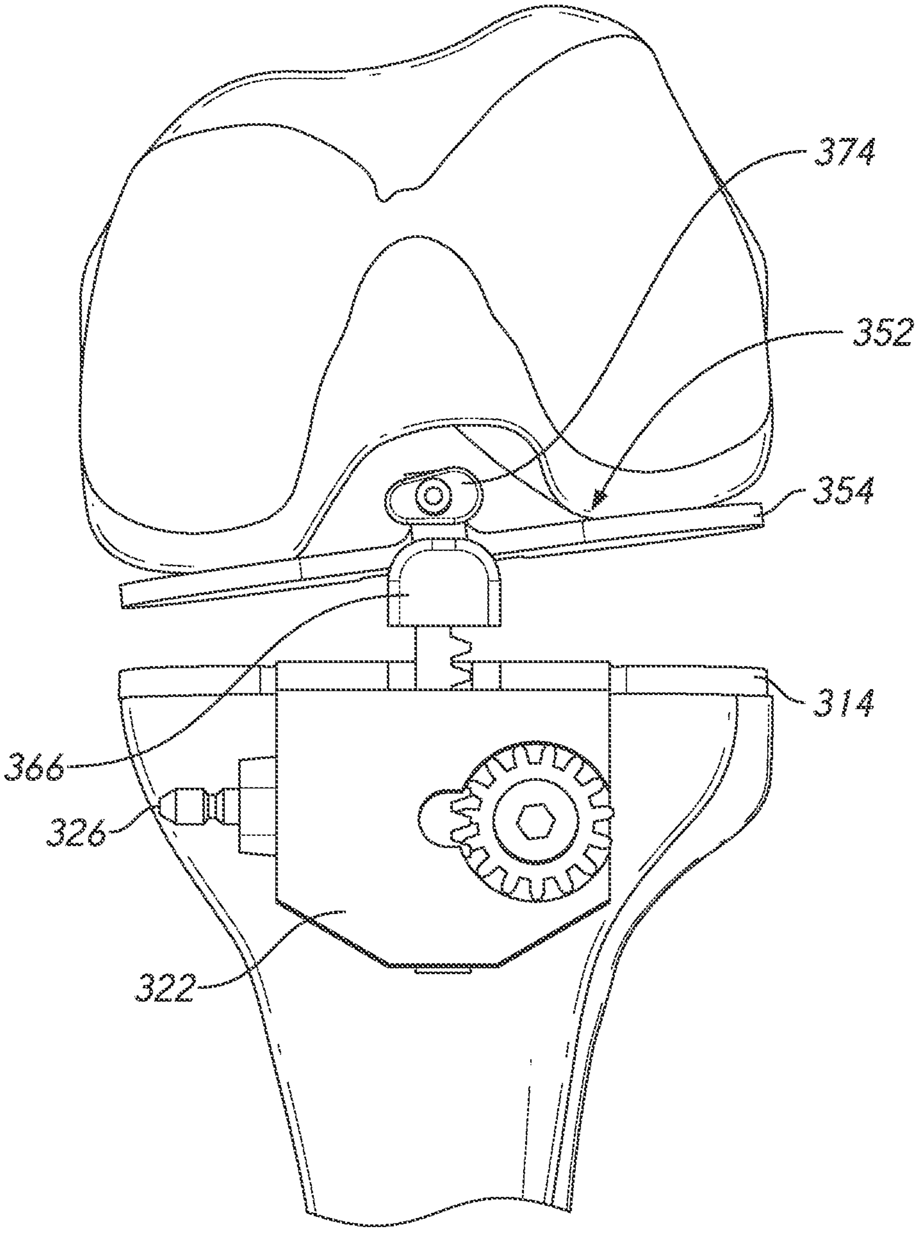

In some embodiments, the femoral baseplate 354 can rotate as shown in FIG. 11B. The femoral baseplate 354 can rotate as the post 332 translates. The femoral system 352 can include the post 332 described herein. The femoral system 352 can include a post mount 366 coupled to the post 322. In some embodiments, the post mount 366 and the post 332 form a unitary structure. The translation of the post 332 can cause corresponding translation of the post mount 366 as described herein. The post mount 366 can allow rotation of the femoral baseplate 354 relative to the post 322. The femoral system 352 can include a rotational interface 368, not shown in FIG. 11B. The rotational interface 368 can be a pin. The femoral baseplate 354 can rotate about the rotational interface 368 relative to the post 322. The femoral baseplate 354 can rotate about the rotational interface 368 relative to the tibial baseplate 314.

The femoral baseplate 354 can apply a different amount of pressure or force to each femoral condyle. The femoral baseplate 354 can apply the same amount of pressure or force to each femoral condyle. The femoral baseplate 354 can rotate in order to put both femoral condyles in tension. The post 332 can be translated until both femoral condyles are under tension by the system 310. The post 332 can be translated until both femoral condyles experience a predetermined force. The adjustment device 336 can be rotated to distract the joint. The adjustment device 336 can be rotated until both collateral ligaments are under tension. In some embodiments, the tibial baseplate 314 can remain stationary while the femoral baseplate 354 is rotated.

Figure 11C:
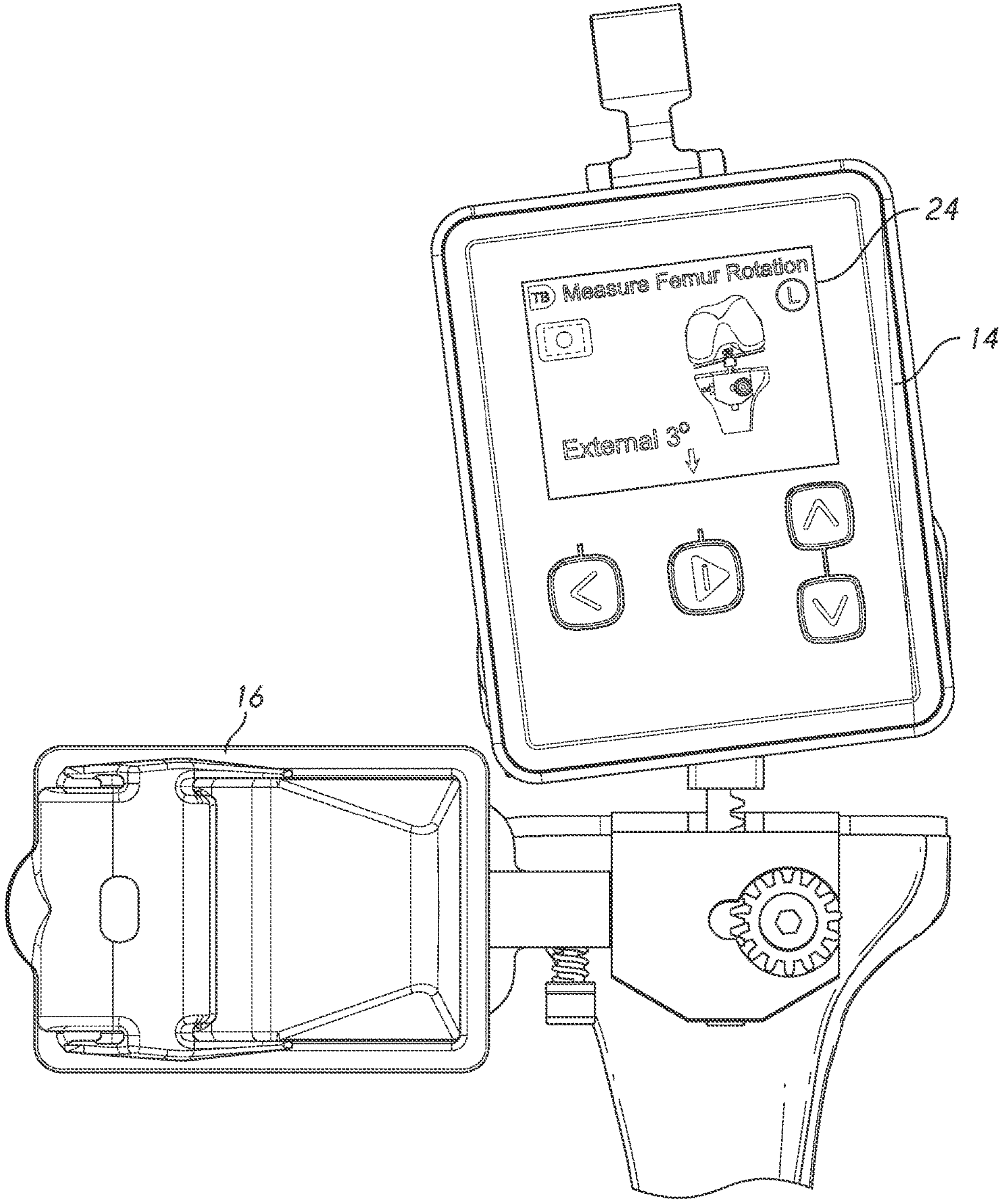

FIG. 11B illustrates the additional coupler 326 and the second coupler 374. FIG. 11C illustrates the surgical orientation device 14 and the reference sensor device 16 coupled to the system 310. As described herein, the mounting block 322 can include one or more additional couplers 326. The additional coupler 326 can be configured to couple with the reference sensor device 16. The one or more additional couplers 326 can be positioned on any surface of the mounting block 322. The additional coupler 326 can be positioned such that the longitudinal axis of the reference sensor device 16 is perpendicular to the longitudinal axis of the tibia. The additional coupler 326 can be positioned such that the longitudinal axis of the reference sensor device 16 is perpendicular to the mechanical axis.

The femoral system 352 can include a second coupler 374. The second coupler 374 can be configured to couple with the surgical orientation device 14. The second coupler 374 can be positioned such that the longitudinal axis of the surgical orientation device 14 aligns with the longitudinal axis of the tibia. The second coupler 374 can be positioned such that the longitudinal axis of the surgical orientation device 14 aligns with the mechanical axis.

FIG. 11C illustrates the surgical orientation device 14 and the reference sensor device 16. The surgical orientation device 14 can be coupled to the second coupler 374. The reference sensor device 16 can be coupled to the additional coupler 326. As described herein, the surgical orientation device 14 is rotationally coupled to the femoral baseplate 354. As the femoral baseplate 354 rotates, the surgical orientation device 14 can rotate as well.

As described herein, the reference sensor device 16 can measure the distraction distance. The reference sensor device 16 can include the camera 344. The camera 344 can provide a measurement of distraction when then leg is in extension. The camera 344 can provide an indication of the extension of the post 332. For example, while the femoral baseplate 354 is being moved and/or rotationally adjusted, and the knee joint is being distracted, the camera 344 can provide a distance measurement. The distance measurement can correspond to the distraction distance between the femoral baseplate 354 and the tibial baseplate 314. In some embodiments, the camera 344 can capture an image of the marking 340, described herein. In some embodiments, the camera 344 can read marking 340, such as a machine readable marking. The surgical orientation device 14 can be configured to display the flexion gap. In some methods of use, the user can read the display 24 of the surgical orientation device 14. In some methods of use, the user can read the markings 340. The system 310 can calculate the anterior-posterior shift needed to match flexion and extension gaps. In some embodiments, the user can compare two numbers shown on the display 24 of the surgical orientation device 14. In some embodiments, the display can show the difference in gaps.

The surgical orientation device 14 can be configured to display distraction distance, as described herein. The surgical orientation device 14 can provide a visual indication of the gap as the gap increases. The surgical orientation device 14 and/or the reference sensor device 16 can convert the image of the camera 344 into a distance measurement. The user can refer to the display 26 of the surgical orientation device 14 for the distraction distance. The distraction distance can be displayed in real-time. The user can read the distraction distance on the display 26 of the surgical orientation device 14.

The surgical orientation device 14 can be configured to display the rotation angle of the surgical orientation device 14 relative to the tibial baseplate 314. The rotation angle of the surgical orientation device 14 can correspond to the posterior condyle angle. The display 26 can indicate the angle of rotation of the femoral baseplate 354. The user can read the rotation angle on the display 26 of the surgical orientation device 14. In some methods of use, the surgical orientation device 14 can provide a visual indication whether a rotation angle is within a pre-determined range. In some methods of use, the surgical orientation device 14 can provide a visual indication of the femur rotation. In some methods of use, the surgical orientation device 14 can provide a visual indication of the soft-tissue balancing. In some methods of use, the surgical orientation device 14 can provide a visual indication that the femur condyles are angled relative to the tibial plateau. The display 26 can provide a digital readout of the rotation angle.

The surgical orientation device 14 and/or the reference sensor device 16 can record the angle of rotation. The surgical orientation device 14 and/or the reference sensor device 16 can store the angle of rotation. The surgical orientation device 14 can provide an angle reading in real-time. The rotation angle of the surgical orientation device 14 can correspond to the posterior condyle angle. The rotation angle of the surgical orientation device 14 can correspond to the posterior condyle angle input to a drill guide or cutting guide. The user can set the angle of a cutting block 394 or drill guide 380 based on the rotation angle displayed on the surgical orientation device 14. The cutting block 394 or drill guide 380 provided with the implant can be adjustable based on the posterior condyle angle. The system 310 provides an accurate reading of the posterior condyle angle.

In some methods of use, the surgical orientation device 14 can provide a visual indication of the medial distraction distance. In some methods of use, the surgical orientation device 14 can provide a visual indication of the lateral distraction distance. In some methods of use, the surgical orientation device 14 and/or the reference sensor device can calculate the medial/lateral distraction distance based on the rotation angle of the surgical orientation device 14. In some methods of use, the surgical orientation device 14 and/or the reference sensor device can calculate the medial/lateral distraction distance based on the distraction distance. In some methods of use, the surgical orientation device 14 and/or the reference sensor device can calculate the medial/lateral distraction distance based on the parameters of the femoral baseplate 354. In some methods of use, the surgical orientation device 14 can provide a visual indication of the difference in a gap, or distance, between one femoral condyle and the tibial plateau is substantially identical to the gap, or distance, between the other femoral condyle and the tibial plateau. In some methods of use, the surgical orientation device 14 can provide a visual indication of rotation angle. In some methods of use, the surgical orientation device 14 can provide a visual indication of distraction distance. In some methods of use, the surgical orientation device 14 can provide a visual indication of baseplate parameters. In some methods of use, the surgical orientation device 14 can provide a visual indication of medial and lateral distraction distances. In some methods of use, the distraction distance is an input to the system 310. In some methods of use, one or more parameters of the tibial baseplate 314 is an input to the system 310. In some methods of use, one or more parameters of the femoral baseplate 354 is an input to the system 310. In some methods of use, the condylar width of the femur is an input to the system 310. In some methods of use, the surgical orientation device 14 can provide a visual indication of a measurement of the condylar width of the femur itself. The measurement of the condylar width can be useful in calculating the medial and lateral distraction distances. In some methods of use, the surgical orientation device 14 can provide a visual indication that a gap, or distance, between the femoral posterior condyles and the tibial plateau is angled. In some methods of use, the surgical orientation device 14 can provide a visual indication that the femoral posterior condyles is angled relative to the tibial plateau. In some methods of use, the surgical orientation device 14 can provide a visual indication that the femoral posterior resection is angled relative to the tibial plateau, once it is executed. The visual indication of the posterior condyles could be a useful final check after the cut is made. The visual indication of the femoral posterior resection could be a useful final check after the cut is made.

In some methods of use, the surgical orientation device 14 can provide a visual indication of a comparison between the distraction distance in flexion and the distraction distance in extension. The display 26 can provide a digital readout of the distraction distance. The user can visually confirm the digital readout of the distraction distance with one or more additional markings 340, such as scale visible to the user. The display 26 can provide a digital readout of the comparison in distraction distance.

In some methods of use, the user can mount drill guide 380 and drill holes with the appropriate anterior-posterior shift based on the anterior-posterior shift calculated by the surgical orientation device 14. The anterior-posterior shift can be difference between the gap in extension and flexion. The user can use selected openings 382 in the drill guide 380 based on the comparison in distraction distance between flexion and extension. For instance, if the difference is 2 mm between the distraction distance in flexion and extension, the user can select a different parallel row of openings, for instance one that increases or decreases the height of the cutting plane of the cutting block by 2 mm. For instance, if the difference is 4 mm between the distraction distance in flexion and extension, the user can select a different parallel row of openings, for instance one that increases or decreases the height of the cutting plane of the cutting block by 4 mm. In some embodiments, the user matches the gap in flexion with the gap in extension. In some embodiments, the user is unable to match the distraction gap in flexion with the distraction gap in extension, for instance due to constraints on the anatomy. The system 310 can calculate the difference in the gap. The user can select a parallel row of openings 382 in the drill guide 382 that correspond to this difference in the gap. The parallel row of openings 382 in the drill guide 382 can adjust the femoral cut in a direction parallel to the tibial baseplate 314. The parallel row of openings 382 in the drill guide 382 can adjust the femoral cut so that the gaps in flexion and extension can match. The user can mount the implant sizing/drill guide on the distal resection surface of the femur. The user can select the appropriate 4-in-1 cutting block 394. The user can remove the implant sizing/drill guide. The user can mount the 4-in-1 cutting block 394. The user can complete resections. The 4-in-1 cutting block 394 will be located with posterior resection slot parallel to tibial resection by correct alignment of drilled guide holes.

In some, alternative methods, the user can measure posterior condyle angle on surgical orientation device 14. The posterior condyle angle can be determined from accelerometer measurements. The user can mount the implant sizing/drill guide on the distal resection surface of the femur. The user can set the implant sizing/drill guide to this angle. The surgical orientation device 14 provides an accurate way to measure the posterior condyle angle. The user can drill holes. The user can select the appropriate 4-in-1 cutting block 394. The user can remove the implant sizing/drill guide. The user can mount the 4-in-1 cutting block 394. The user can complete resections. The 4-in-1 cutting block 394 will be located with posterior resection slot parallel to tibial resection by correct alignment of drilled guide holes.

The surgical orientation device 14 and/or the reference sensor device 16 can be configured to measure the tension within the soft tissue on the medial and/or lateral sides of the knee joint. In some embodiments, the surgical orientation device 14 and/or the reference sensor device 16 can be configured to measure the tension from the distraction distance. In some embodiments, the system 310 can comprise sensors, or other structures, which can relay information to the surgical orientation device 14 and/or the reference sensor device 16 about the degree of tensile force being exerted. The surgical orientation device 14 can be configured to display the force.

In some embodiments, the user can release one or more ligaments in the knee joint prior to or during the knee distraction in order to facilitate simultaneous symmetry of the gaps, mechanical axis alignment, and/or balancing of the soft tissue and/or ligaments in the knee joint. In some methods of use, the user can modify the soft tissue to align the femoral baseplate 354 and the tibial baseplate 314 to alter the angle. The far more common scenario is that soft tissue is modified only in extension. The user can nick or cut soft tissue to adjust for laxity of the knee joint. The user performs soft tissue balancing until the femoral baseplate 354 and the tibial baseplate 314 are at the desired angle.

The surgical orientation device 14 and/or the reference sensor device 16 can store any data related to the distraction. The surgical orientation device 14 and/or the reference sensor device 16 can be configured to store the distraction distance of the femur and the tibia. The surgical orientation device 14 and/or the reference sensor device 16 can be configured to store the distraction distance of the femur and the tibia when the leg is in flexion. The surgical orientation device 14 can compare the distraction distance in flexion and extension. The surgical orientation device 14 can store data for a post-operative comparison. The surgical orientation device 14 can store data for post-operative record of parameters used during the procedure.

After distraction, holes can be drilled into the femur, and reference pins can be inserted. As described herein the drill guide 380 can include one or more openings 382. The openings 382 can be used to guide a drill and/or pins. For example, when the system 310 has distracted a distal femur in a knee replacement procedure, a pin or pins can be inserted into the resected surface in order to provide a mounting location for a cutting block. The openings 382 can be used as guides for insertion of these pins.

The openings 382 can be spaced apart from one another in a pattern or patterns. For example, some of the openings 382 can be spaced slightly higher, and/or further away from the tibial baseplate 624 than other openings 646. This spacing can be used, for example, to control the orientation of a cutting block which is attached to the pins. The reference pins can be inserted into various openings 382 of the drill guide 380, again depending on the desired angle of resection. For example, and as described above, some of the openings 382 can be located at slightly different levels or elevations on the drill guide 380. Depending on where the reference pins are inserted, a slightly different angle of resection can be achieved (e.g. zero degrees, plus three degrees, minus three degrees relative to the tibial resection).

Figure 11D:
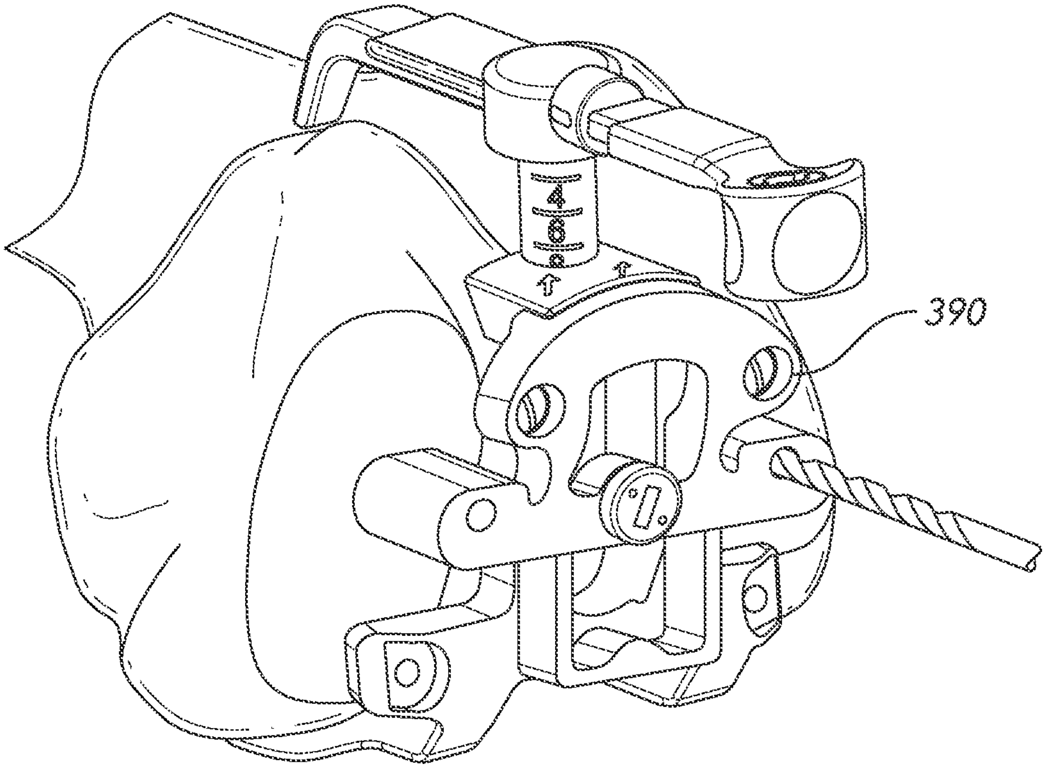
Figure 11E:
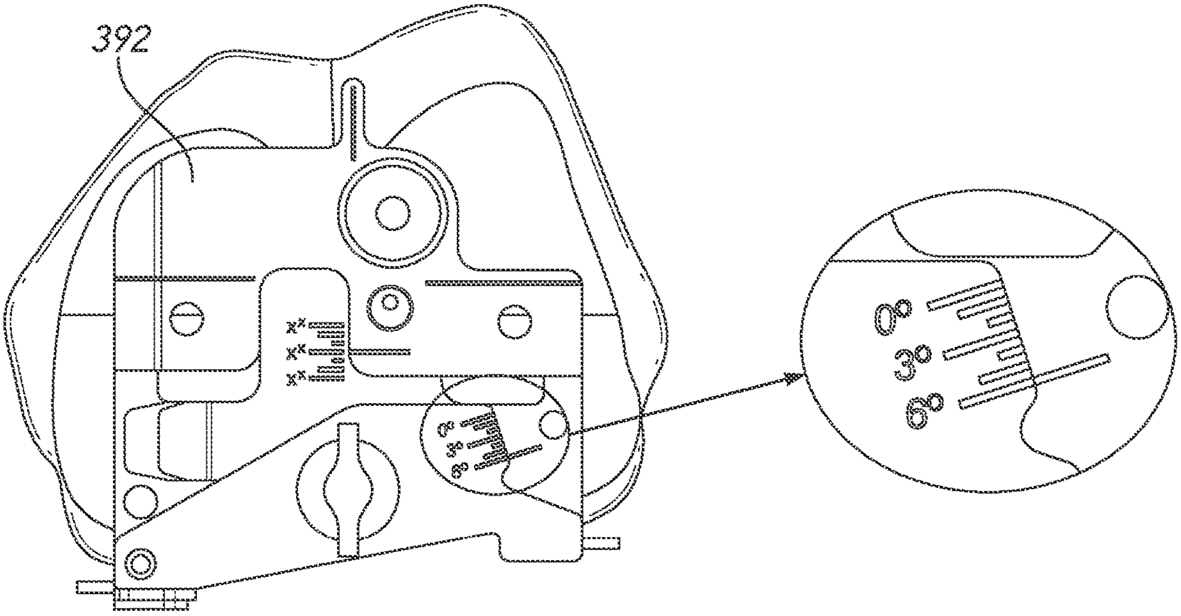
Figure 11F:
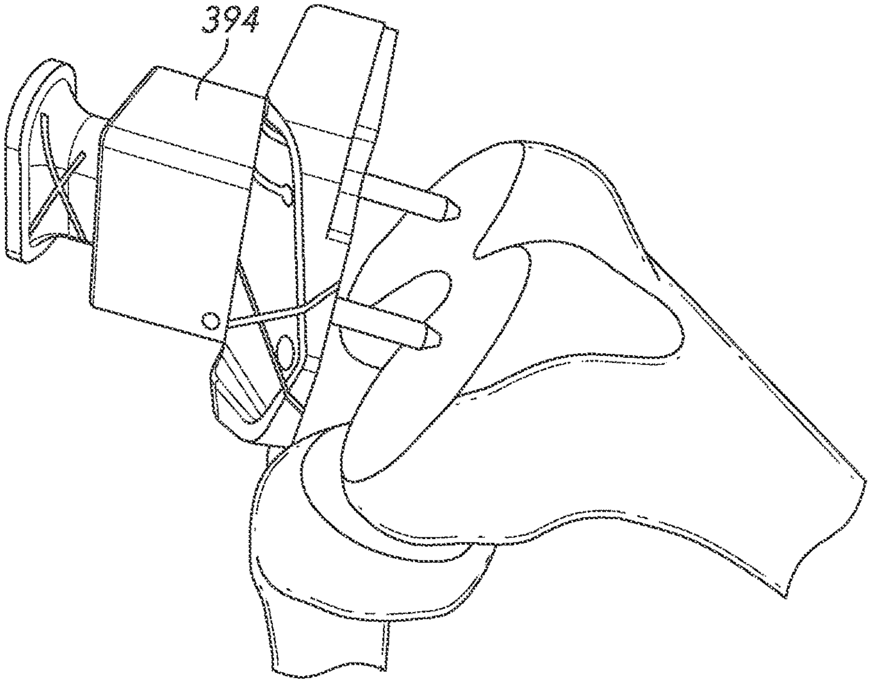

FIG. 11D illustrates the use of a sizing guide 390. The system 310 can be removed as shown in FIG. 11D. The sizing guide can correspond to the selected implant. The sizing guide 390 can be adjusted to the rotation angle displayed on the surgical orientation device 14 during distraction in flexion. The system 310 can set pin locations for the femur cutting block. The system 310 can set the rotational alignment for the femur cutting block. The sizing guide 390 is an example of a typical sizing/drill guide from an implant instrument set. There are other commercial examples. FIG. 11E is an alternative sizing guide 392. FIG. 11F is an embodiment of a 4-in-1 cutting block 394.

Once the reference pins are inserted, a cutting block 394 can be placed onto or coupled with the reference pins. A saw or other cutting device can then make appropriate PFC cut or cuts (e.g. an anterior, additional posterior, and/or chamfer along the femur. Once all of the tibial and/or femoral cuts are made with the systems and/or methods described above, a knee joint prosthetic or prosthetics can be attached to the distal femur and/or proximal tibia. The knee joint prosthetic devices can comprise a replacement knee joint. The replacement knee joint can be evaluated by the user to verify that alignment of the prosthetic components in the replacement knee joint does not create any undesired wear, interference, and/or damage to the patient's anatomy, or to the prosthetic components themselves.

Figure 12A:
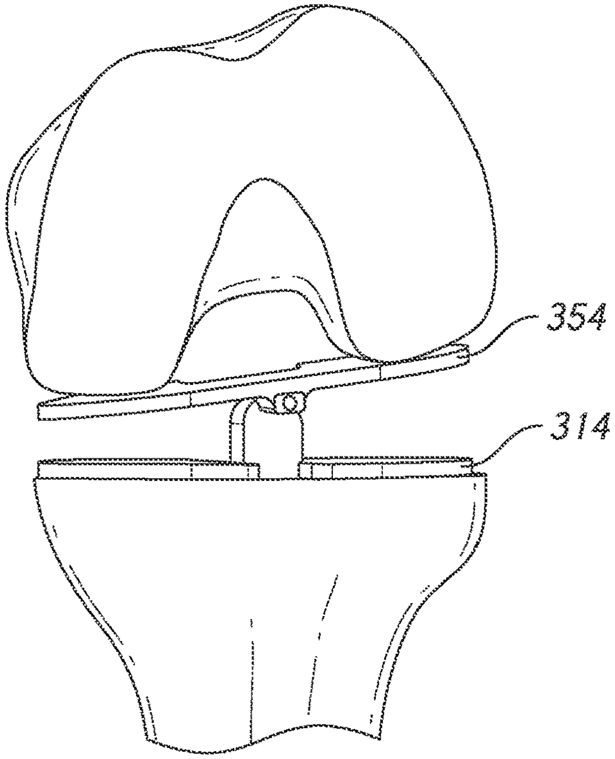
FIGS. 12A-12E are views of a femoral preparation and knee distraction system for soft tissue balancing.
Figure 12B:
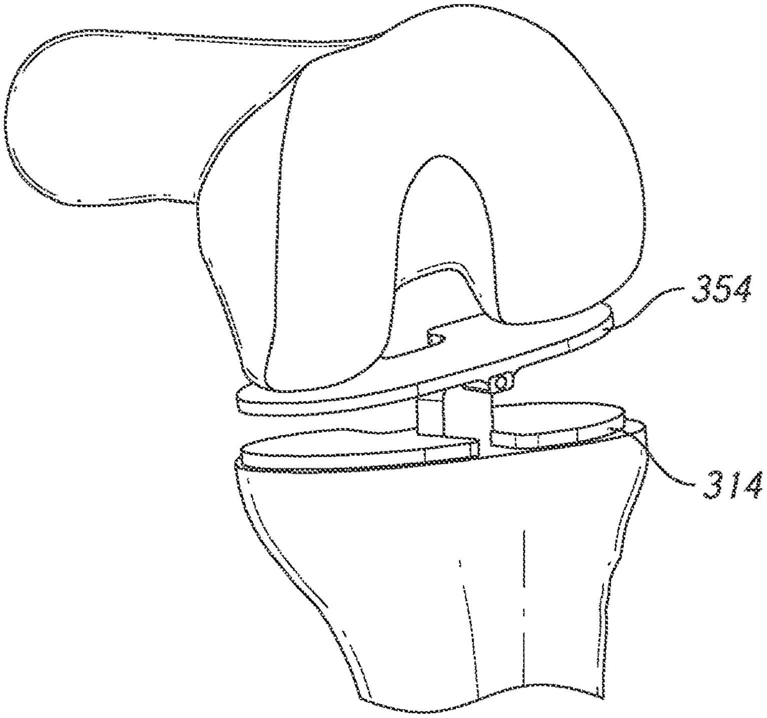
Figure 12C:
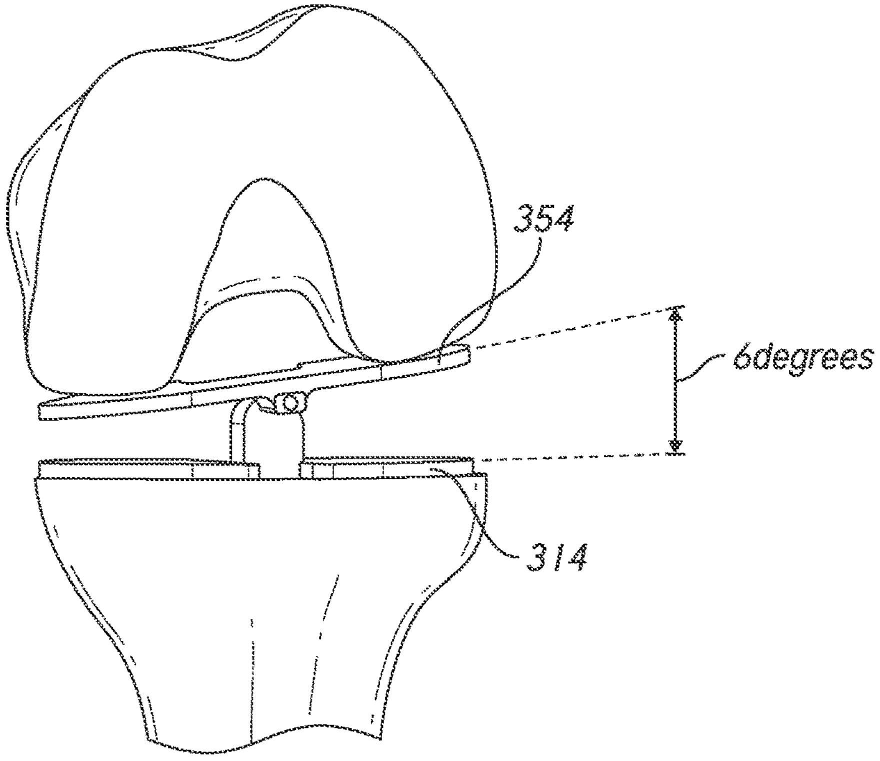
Figure 12D:
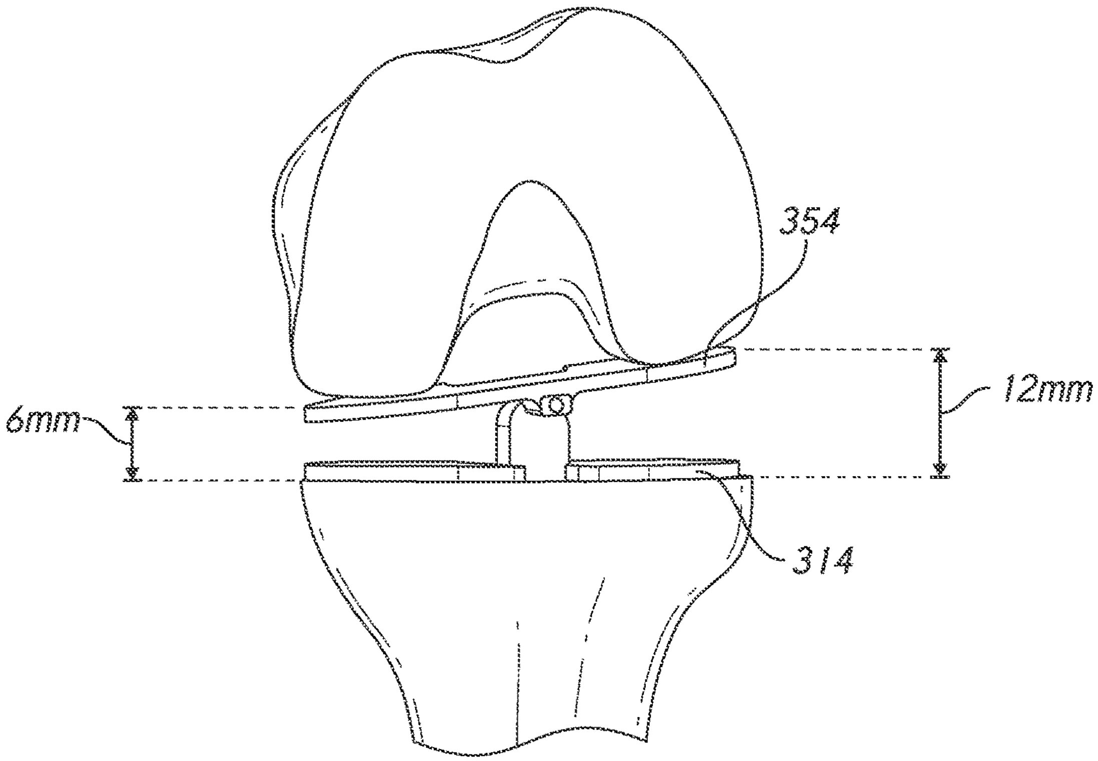
Figure 12E:
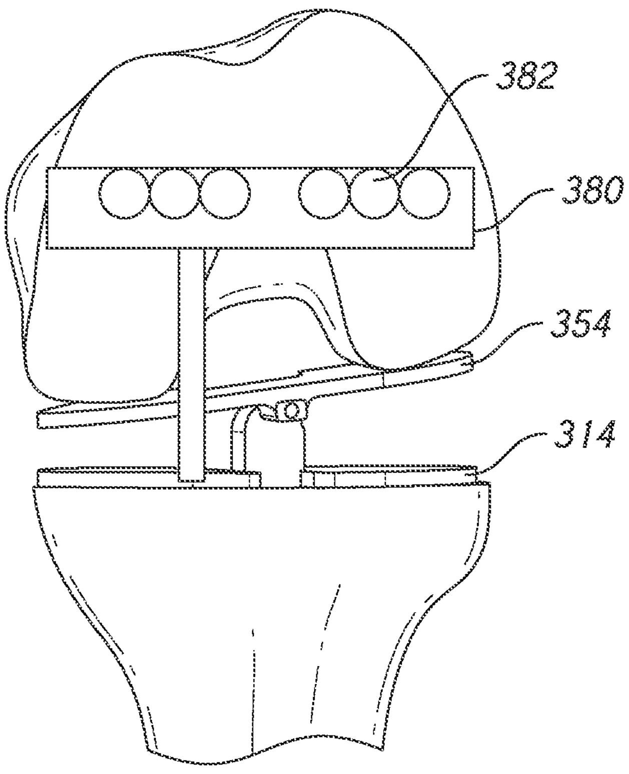

FIG. 12A-12D illustrate additional views of the femoral baseplate 354 and the tibial baseplate 314. The femoral baseplate 354 can be rotated relative to the tibial baseplate 314. The system 310 can measure the angle of rotation of the femoral baseplate 354 as shown in FIG. 12C. The system 310 can measure the distraction distance of the medial and/or lateral sides of the knee joint as shown in FIG. 12D. FIG. 12E is a schematic illustration of the drill guide 380 comprising openings 382. The drill guide 380 can be coupled to the tibial baseplate 314 as described herein. The drill guide 380 can remain parallel to the tibial baseplate 314 during rotation of the femoral baseplate 354.

C. Alternative Femoral Preparation and Knee Distraction System

FIGS. 13A-13E show an embodiment of a system 510. The system 510 can be used to perform many functions, as described herein. The system 510 can include any of the features of any other system described herein including system 310. The system 510 can be configured to distract the knee joint during a knee replacement procedure. The system 510 can be configured to measure the rotation of the femur relative to the tibial resection. The system 510 can be configured to orient a resection plane. The system 510 can be configured to guide posterior resection. The system 510 can be used to prepare the femur, such as facilitate the posterior femoral cut. The system 510 can be configured to provide information about how to resect the femur.

Figure 13A:
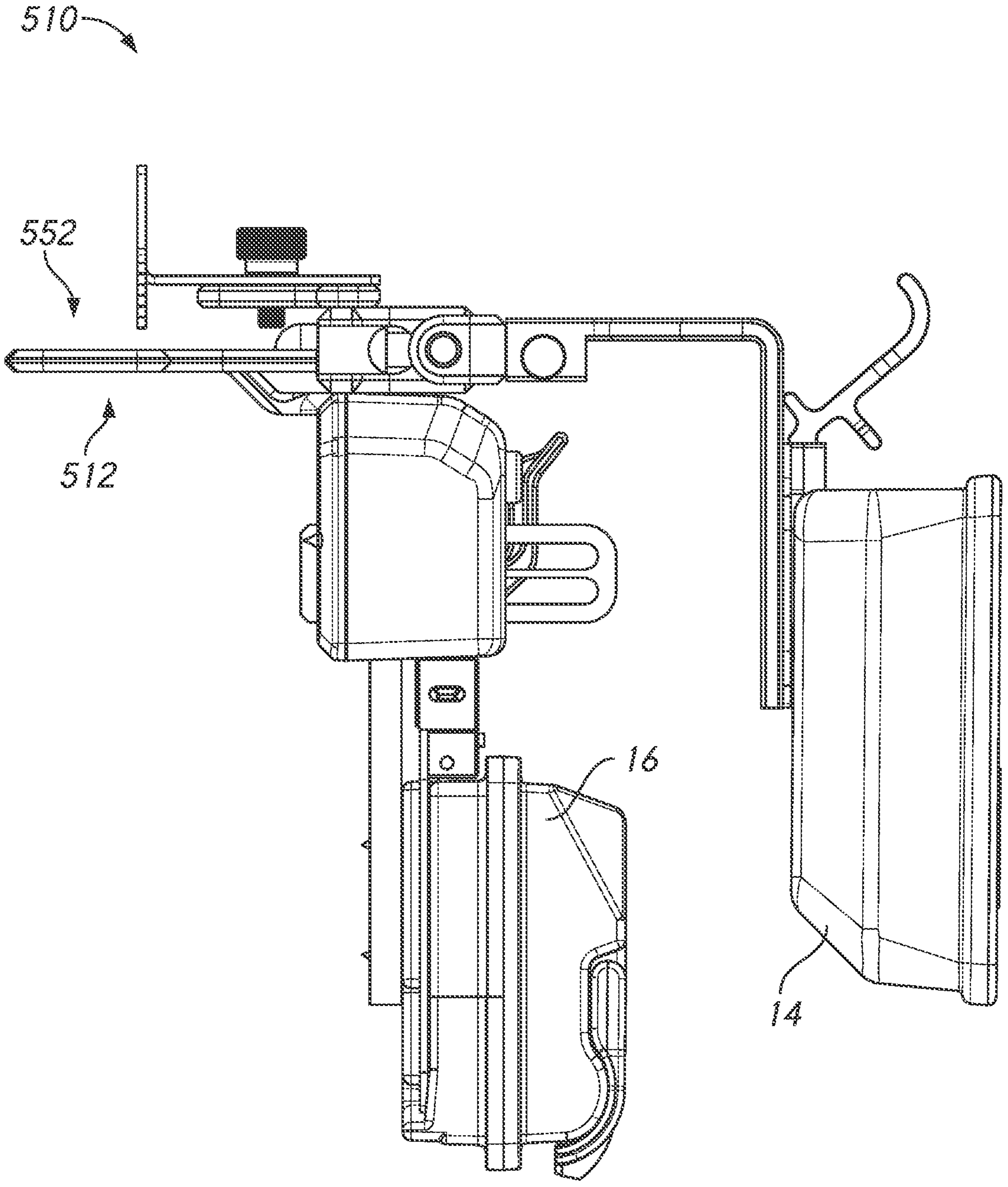
FIGS. 13A-13E illustrate views of another embodiment of a femoral preparation and knee distraction system.
Figure 13B:
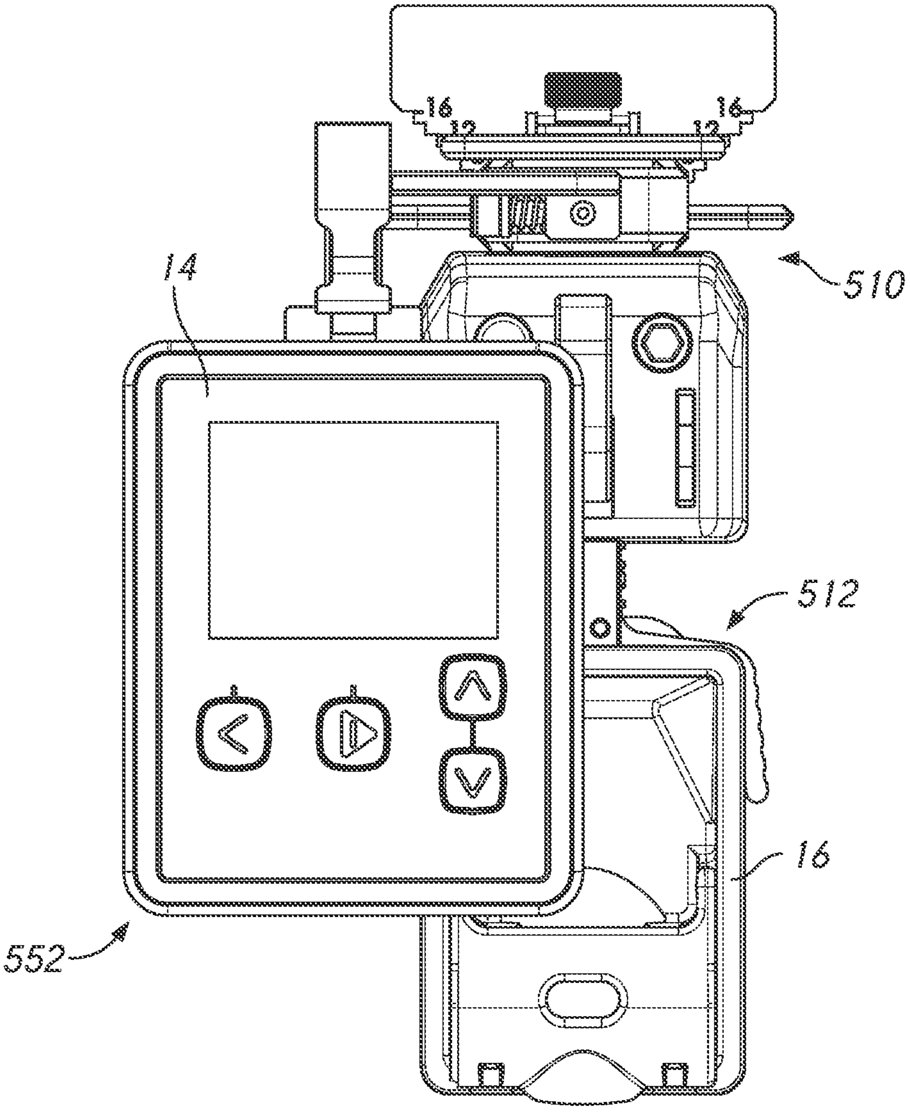
Figure 13C:
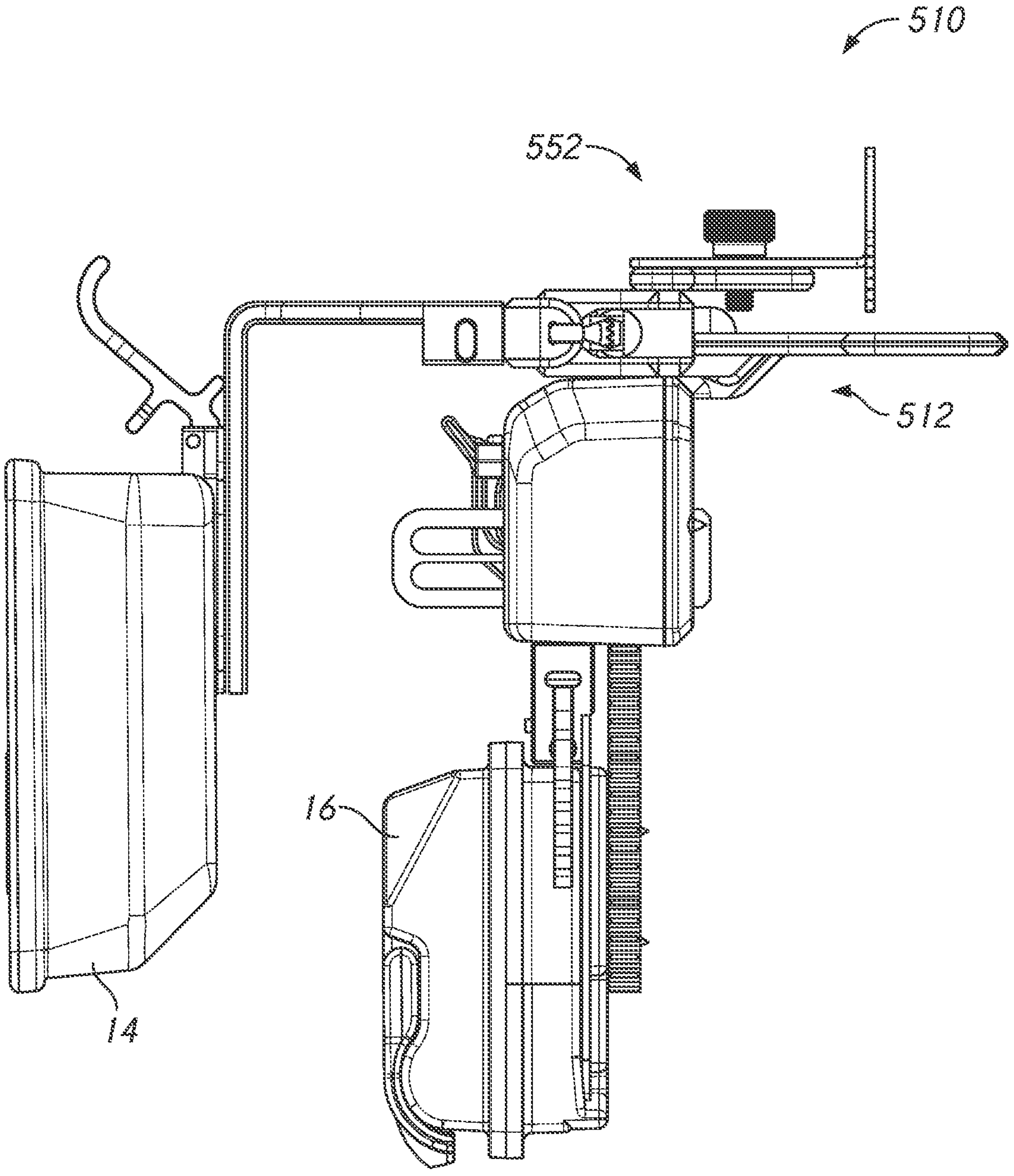
Figure 13D:
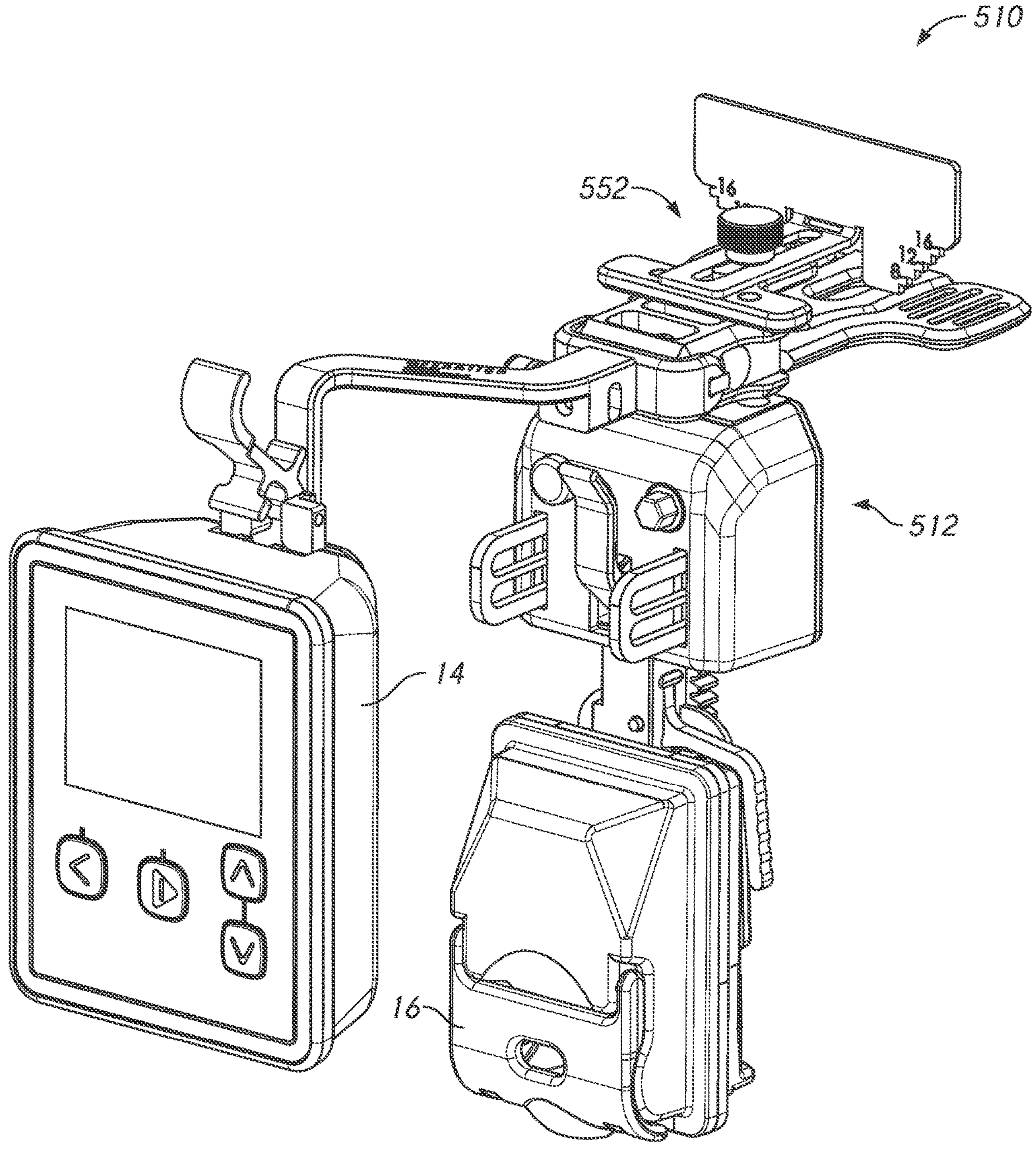
Figure 13E:
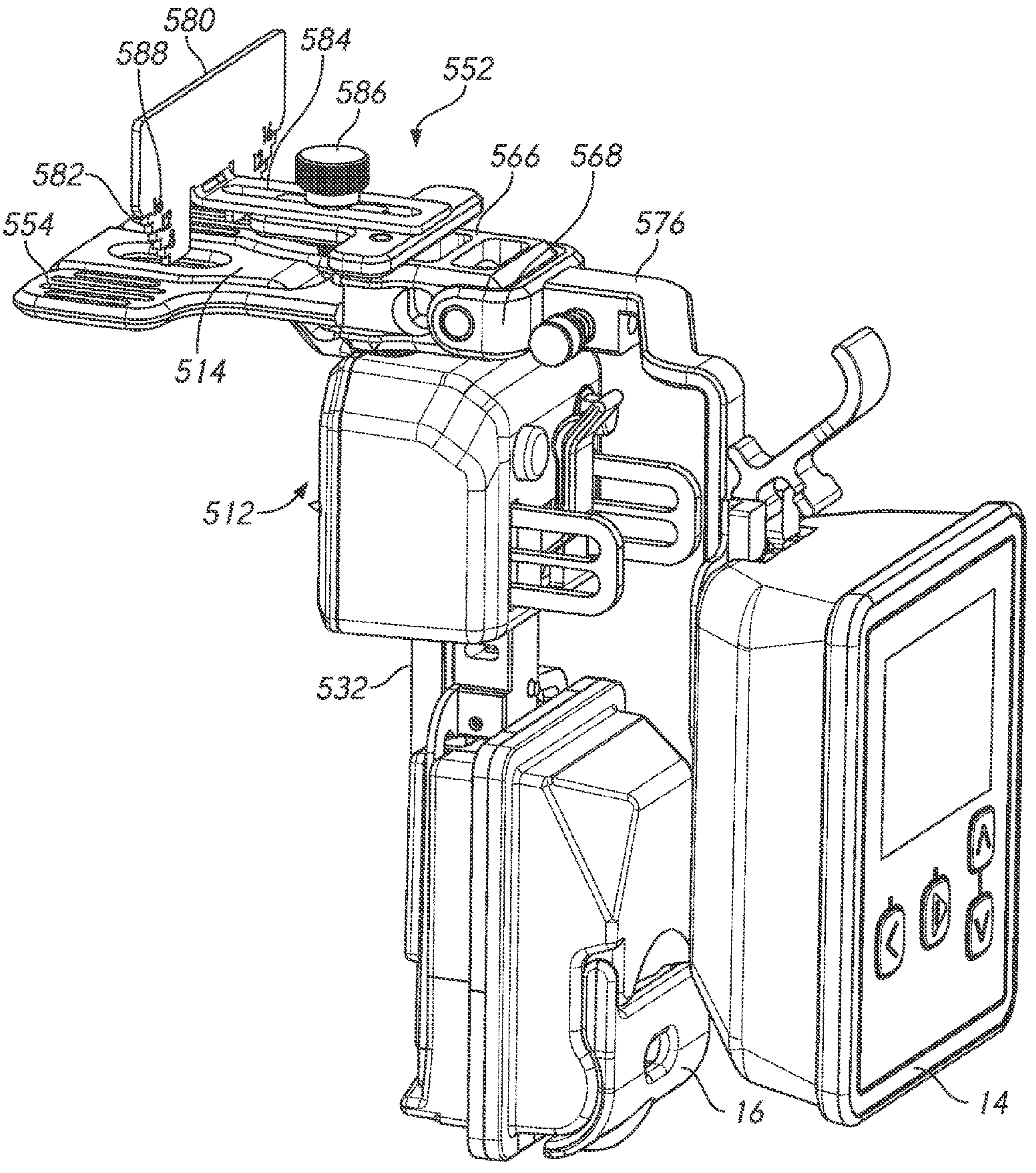

The system 510 can comprise the surgical orientation device 14 and the reference sensor device 16 as described herein. The system 510 can further comprise one or both of a tibial system 512 and a femoral system 552, as described herein. While the tibial system 512 and the femoral system 552 are described as discrete subsystems, the system 510 can be considered one instrument. In some embodiments, the system 510 can be implanted as an inseparable assembly. In some embodiments, the discrete subsystems of the system 510 can be positioned on or in the patient separately. In some embodiments, the discrete subsystems of the system 510 can be positioned on or in the patient simultaneously. FIG. 13E shows additional features as described herein.

1. Tibial System

Figure 14A:
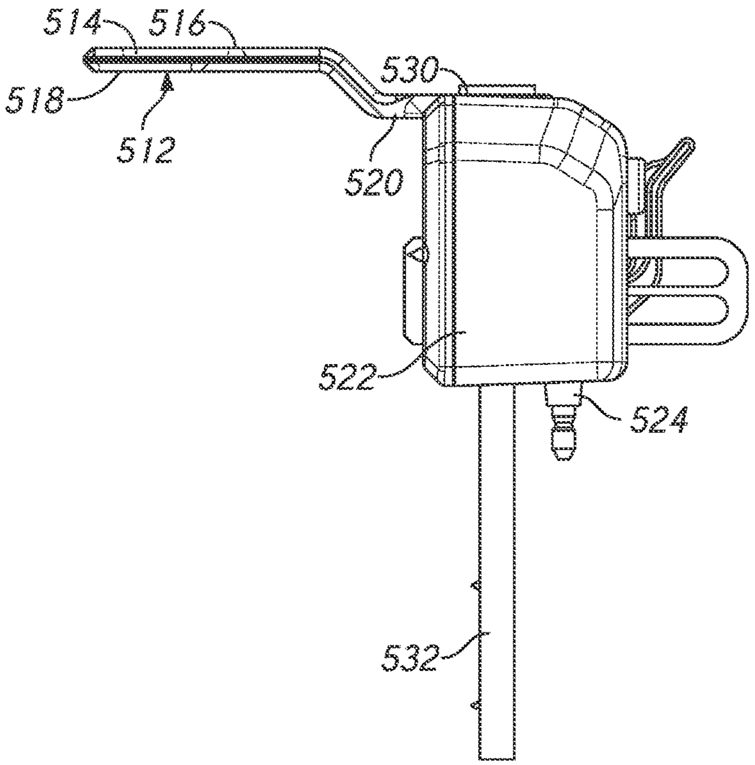
FIGS. 14A-14B illustrate views of a tibial system of the femoral preparation and knee distraction system of FIG. 13A.
Figure 14B:
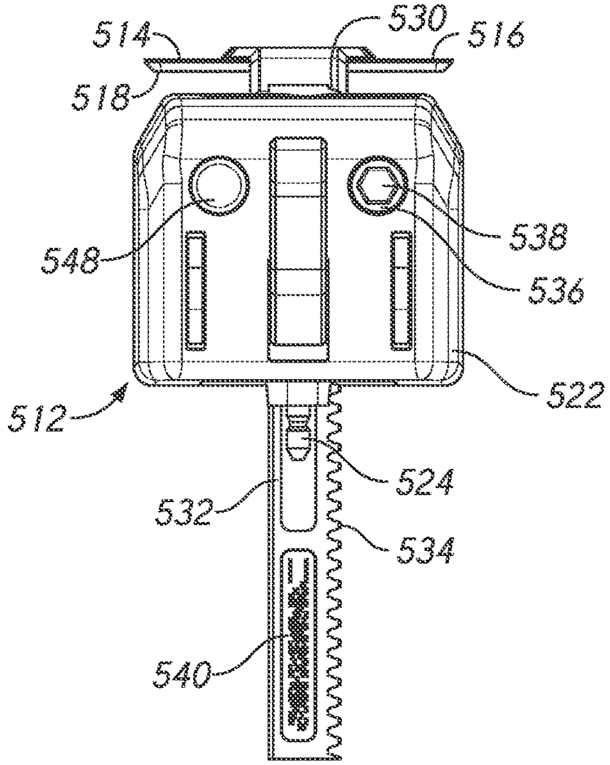

FIGS. 14A and 14B illustrate the tibial system 512. The tibial system 512 can include any of the features of the tibial system 312. The tibial system 512 can include a tibial baseplate 514. The tibial baseplate 514 can comprise a first surface 518 configured to align with the flat surface of the resected tibia. The tibial baseplate 514 can include a second surface 516, opposite the first surface 518 positioned toward the femur. The tibial system 512 can include an extension member 520. The tibial system 512 can include a mounting block 522. The extension member 520 can span between the mounting block 522 and the tibial baseplate 514. The extension member 520 can position the mounting block 522 away from, e.g., anteriorly of, the knee joint.

The mounting block 522 can include a first coupler 524. The first coupler 524 can be configured to couple with the surgical ordination device 14 and/or the reference sensor device 16. The first coupler 524 can include any of the features of the couplers described herein. In the illustrated embodiment, the first coupler 524 is positioned on a bottom surface of the mounting block 522. In the illustrated embodiment, the first coupler 524 extends perpendicular to the tibial resection. In the illustrated embodiment, the first coupler 524 is positioned such that the longitudinal axis of the reference sensor device 16 aligns with the longitudinal axis of the tibia. The axis of the tibia can be perpendicular to the tibial resection. In the illustrated embodiment, the first coupler 524 is positioned such that the longitudinal axis of the reference sensor device 16 aligns with a mechanical axis associated with the knee joint, e.g., of the tibia or the leg. In some embodiments, the mounting block 522 can include one or more additional or alternative couplers as described herein.

The mounting block 522 can include a guide portion 530. The guide portion 530 can extend entirely through the mounting block 522 or a portion thereof. The guide portion 530 can include at least an opening on the bottom of the mounting block 522. In some embodiments, the guide portion 530 can include an opening on the bottom of the mounting block 522 and on the top of the mounting block. The guide portion 530 can include at least two diametrically opposed openings. In some embodiments, the guide portion 530 can be a channel through the mounting block 522. In some embodiments, the guide portion 530 can include a round or circular channel through the mounting block 522. Other configurations for the guide portion 530 are contemplated including a triangular, elliptical, rectangular, or polygonal channel.

The mounting block 522 can be configured to facilitate movement of a post 532 of the femoral system 552 therethrough. The post 532 and the guide portion 530 can a have complementary or corresponding cross-sectional profile. The post 532 and the guide portion 530 can have corresponding cross-sectional dimension or diameter. In some embodiments, the guide portion 530 and the post 532 are substantially similar in cross-sectional dimensions. The post 532 and the guide portion 530 can be shaped to allow metered movement of the post 532 through the guide portion 530. The guide portion 530 can guide the post 532 through the mounting block 522. The guide portion 530 can be configured to allow the post 532 to slide through the mounting block 522. As described herein, the post 532 can be coupled to the femoral system 552. The post 532 can be a portion of an actuation system that provides for movement of the femoral system 552 relative to the tibial system 512.

In some embodiments, a portion of the post 532 and the guide portion are rounded. An advantage of a rounded or circular post 532, or a rounded or circular portion thereof, can include tighter tolerances between the mounting block 522 of the tibial system 512 and the post 532 of the femoral system 552. An advantage can include better alignment between the tibial system 512 and the femoral system 552. An advantage can include more precision in aligning a scale or marking located on the post 532 with the camera 334 of the reference sensor device 16. An advantage can include higher precision movement between the tibial system 512 and the femoral system 552. An advantage can include reduction or prevention of unwanted movement, for example, side to side movement between the tibial system 512 and the femoral system 552. An advantage can include reduced manufacturing costs associated with manufacturing the rounded guide portion 530 and the rounded post 532.

FIG. 14B illustrates the post 532 relative to the mounting block 522 in one position. The post 532 can include a marking 540 which can extend below the mounting block 522. The post 532 can include a rack 534 which can extend below the mounting block 522 in the illustrated position. The post 532 can extend from below the mounting block 522 to above the mounting block 522. The post 532 can connect to the femoral system 552 as described herein. The marking 540 can be optically detected by the camera 344. The marking 540 can be any camera-readable representation.

In some embodiments, the guide portion 530 can include an anti-rotation configuration limit rotation, e.g., to allow the post 532 to extend in only one orientation through the guide portion 530 of the mounting block 522. In some embodiments, components of the actuation system allow the post 532 to extend in only one orientation through the guide portion 530 of the mounting block 522. The post 532 and/or the guide portion 530 can include a feature to reduce or prevent rotation. In some embodiments, the shape of the post 532 can reduce or prevent rotation.

Figure 15A:
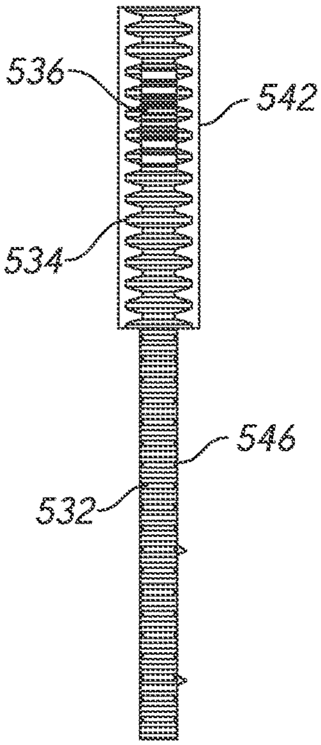
FIGS. 15A-15E illustrate views of an actuation system of the femoral preparation and knee distraction system of FIG. 13A.
Figure 15B:
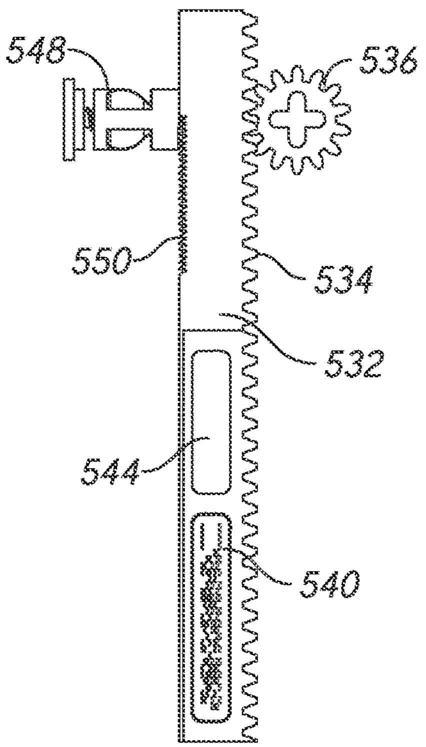
Figure 15C:
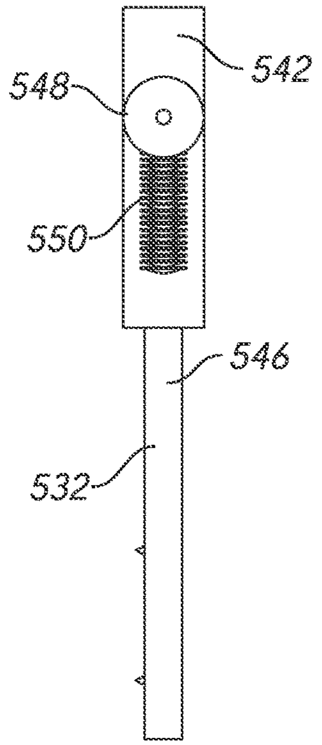
Figure 15D:
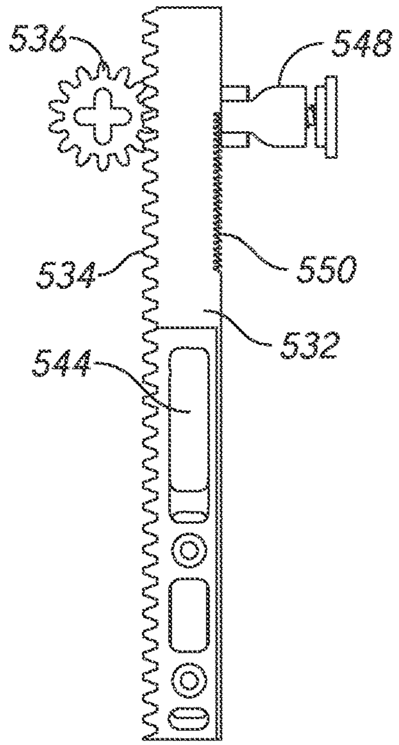
Figure 15E:
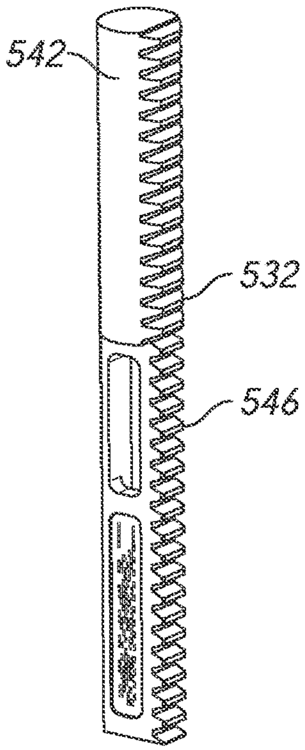

FIGS. 15A-15D illustrates the actuation system of the system 510. FIG. 15E is a perspective view of the post 532. The system 510 can include the actuation system to allow movement between the tibial system 512 and the femoral system 552. The actuation system can be positioned anywhere within the system 510. In the illustrated embodiment, the tibial system 512 can house certain components of the actuation system. The actuation system can include the post 532. The post 532 can connect the tibial system 512 and the femoral system 552.

The actuation system can include an adjustment device 536. The adjustment device 536 can be located at least partially within the mounting block 522. The adjustment device 536 can extend from the mounting block 522 to allow movement of the adjustment device 536 by the user. FIG. 14B illustrates one positional relationship between the adjustment device 536 and the mounting block 522.

The adjustment device 536 can be configured to provide a force of distraction between the tibial system 512 and the femoral system 552. The adjustment device 536 can be configured to maintain the position between the tibial system 512 and the femoral system 552. The adjustment device 536 can be configured to maintain the position of the post 532 relative to the mounting block 522. The adjustment device 536 can be configured to apply a force in the range of 150 N to 200 N. The adjustment device 536 can be configured to apply 50 N, 60 N, 70 N, 80 N, 90 N, 100 N, 110 N, 120 N, 130 N, 140 N, 150 N, 160 N, 170 N, 180 N, 190 N, 200 N, 210 N, 220 N, 230 N, 240 N, 250 N, 260 N, 270 N, 280 N, 290 N, 300 N, or any range including two or more of the foregoing values. The adjustment device 536 can be configured to translate the post 532 relative to the mounting block 522 upon actuation by the user.

In some embodiments, the adjustment device 536 can include a pinion configured to interact with a rack 534 on the post 532. In some embodiments, the adjustment device 536 can include a drive pinion. The post 532 can be substantially straight along its length. The rack 534 can extend along an edge of the post 532. The rack 534 can extend along the length of the post 532, or a portion thereof. The adjustment device 536 can interact with the rack 534 such that rotation of the adjustment device 536 causes translation of the post 532. The adjustment device 536 can be free to rotate within the mounting block 522. The adjustment device 536 can be prevented from translation within the mounting block 522. Other configurations are contemplated. The adjustment device 536 can include any feature to allow relative movement including a gear, detent, pawl, pinion, screw, ramp, rack, etc. The post 532 can include any corresponding feature to allow relative movement including a gear, detent, pawl, pinion, screw, ramp, rack, etc. The adjustment device 536 can include any mechanical feature which can be actuated to cause translation of the post 532.

In some embodiments, the adjustment device 536 can be rotated to cause translational movement of the post 532. In some embodiments, the adjustment device 536 can be translated to cause translational movement of the post 532. The adjustment device 536 can include an interface 538 which can engage a driver. The interface 538 can allow the user to rotate or translate the adjustment device 536. The interface 538 can include a recess or a protrusion. In some embodiments, the interface 538 can be a hex recess. The interface 538 can allow rotation of the adjustment device 536 by a driver as described herein. Other configurations of the interface 538 are contemplated.

The actuation system can include a catch 548. The catch 548 can be located at least partially within the mounting block 522. In some embodiments, the catch 548 can extend from the mounting block 522 to allow adjustment of the catch 548 by the user. In some embodiments, the catch 548 can be contained within the mounting block 522 such that the catch 548 is inaccessible to the user. FIG. 14B illustrates one positional relationship between the catch 548 and the mounting block 522.

The catch 548 can be configured to provide incremental positioning between the tibial system 512 and the femoral system 552. The catch 548 can be configured to provide fine resolution positioning of the post 532 relative to the mounting block 522. The catch 548 can be configured to allow positioning at increments of 1 mm. The catch 548 can be configured to allow positioning at increments of 0.25 mm, 0.5 mm, 0.75 mm, 1 mm, 1.25 mm, 1.5 mm, 1.75 mm, 2 mm, or any range including two or more of the foregoing values. The catch 548 can be configured to allow adjustment of the position of post 532 relative to the mounting block 522.

In some embodiments, the catch 548 can be a pawl configured to interact with a ratchet 550 on the post 532. In the illustrated embodiment, the catch 548 is a spring loaded pawl. In some embodiments, the catch 548 can be biased into engagement with the ratchet 550. The post 532 can be substantially straight along its length. The ratchet 550 can extend along an edge of the post 532. The ratchet 550 can extend along the length of the post 532, or a portion thereof. The catch 548 can interact with the ratchet 550 such that actuation of the catch 548 can cause incremental positional changes of the post 532. The catch 548 can be free to actuate within the mounting block 522. The catch 548 can be prevented from translation within the mounting block 522. Other configurations are contemplated. The catch 548 can include any feature to allow relative movement including a gear, detent, pawl, pinion, screw, ramp, rack, etc. The post 532 can include any corresponding feature to allow relative movement including a gear, detent, pawl, pinion, screw, ramp, rack, etc. The catch 548 can include any mechanical feature which can be actuated to cause translation of the post 532. In some embodiments, the catch 548 can allow unidirectional movement of the post 532. In some embodiments, the catch 548 can allow bidirectional movement of the post 532.

The catch 548 can interact with the ratchet 550 such that translation of the post 532 can be maintained at an incremental position. As the user actuates the adjustment device 536, the catch 548 can be configured to slide along the teeth of the ratchet 550. When the user stops actuating the adjustment device 536, the catch 548 can maintain the position of the post 532. An advantage of the catch 548 can be to allow finer adjustments of the post 532 than the adjustment device 536. In some embodiments, the gears or teeth of the ratchet 550 can be at smaller increments than the gears or teeth of the rack 534. An advantage of the catch 548 can be to prevent slippage of the adjustment device 536 once the user stops actuating the adjustment device 536. Without the catch 548, a gear of the adjustment device 536 may be able to slip the distance between engaging a bottom surface of a gear on the rack 534 to engaging a top surface of an adjacent gear on the rack 534. An advantage of the catch 548 can be to limit movement in one or more direction. In some embodiments, when the catch 548 is engaged with the ratchet 550, the translation of the post 532 can be limited in one direction. In some embodiments, when the catch 548 is engaged with the ratchet 550, the translation of the post 532 can be limited in both directions. The contact between the catch 548 and the ratchet 550 can additionally or alternatively provide a force (e.g. frictional) which can hold the post 532 in a desired position, until the adjustment device 536 is turned again.

In some embodiments, the catch 548 can automatically engage the ratchet 550 regardless of movement of the adjustment device 536. In some embodiments, the catch 548 is spring loaded or biased into engagement with the ratchet 550. In some embodiments, the catch 548 can be biased to slide along the ratchet 550 when the adjustment device 536 is being actuated. In some embodiments, the catch 548 can be biased to maintain its position along the ratchet 550 when the adjustment device 536 stops being actuated. In some embodiments, the catch 548 can be controlled by the user. In some embodiments, the catch 548 can be engaged or disengaged with the ratchet 550 by the user interacting with an interface (not shown). In some embodiments, the catch 548 is not accessible or controllable to the user.

In some embodiments, the user can experience feedback related to movement of the post 532 relative to the catch 548. For example, the system 510 can provide audible, tactile, and/or visual feedback to the user, indicating the degree or extent to which the post 532 has been moved. In some embodiments, the catch 548 proves audible feedback. In some embodiments, the catch 548 proves tactile feedback. In some embodiments, the user can hear and/or feel the catch 548 contacting the ratchet 550 as the post 532 moves up and/or down. This contact can produce an audible click, or clicks. In some embodiments, the user can view a scale or other marking on the post 532 related to the position of the catch 548. Other modes of feedback are contemplated.

The actuation system can include the post 532. The post 532 can be located at least partially within the mounting block 522. In some embodiments, the post 532 can extend from the mounting block 522 to allow translation of the post 532 relative to the mounting block 522. FIG. 14B illustrates one positional relationship between the post 532 and the mounting block 522.

The post 532 can include an upper portion 542. In some embodiments, the upper portion 542 can be configured to move within the mounting block 522. The upper portion 542 can include the rack 534. The upper portion 542 can include the ratchet 550. The upper portion 542 can include a rounded cross-sectional shape. The post 532 can include a lower portion 546. The lower portion 546 can include any cross-sectional shape, including a non-round cross-sectional shape. In the illustrated embodiment, the lower portion 546 can have a rectangular cross-sectional shape. The post 532 can include a window 544. The upper portion 542 can be above the window. The lower portion 546 can include the window 544.

In some embodiments, the post 532 can include one or more markings 540. The marking 540 can be located on the lower portion 546. The lower portion 546 can include at least one flat side for the marking 540 to be disposed thereon. The marking 540 can indicate the position of the post 532. By taking one or more readings of the marking 540, the system 510 can determine the distance traveled by the post 532. In some embodiments, the marking 540 can be a scale. In some embodiments, the marking 540 can be captured by the camera 344. The post 522, or a portion thereof, that extends beyond the mounting block 522 can include the marking 540. The marking 540 can align with the camera 344 of the reference sensor device 16. The camera 344 can capture an image of the marking 540. The image of the marking 540 can be analyzed to determine an initial position of the tibial system 512 and the femoral system 552. The image of the marking 540 can be captured and analyzed at another time during the procedure. The marking 540 can indicate a distraction distance between the tibial system 512 and the femoral system 552.

Figure 16A:
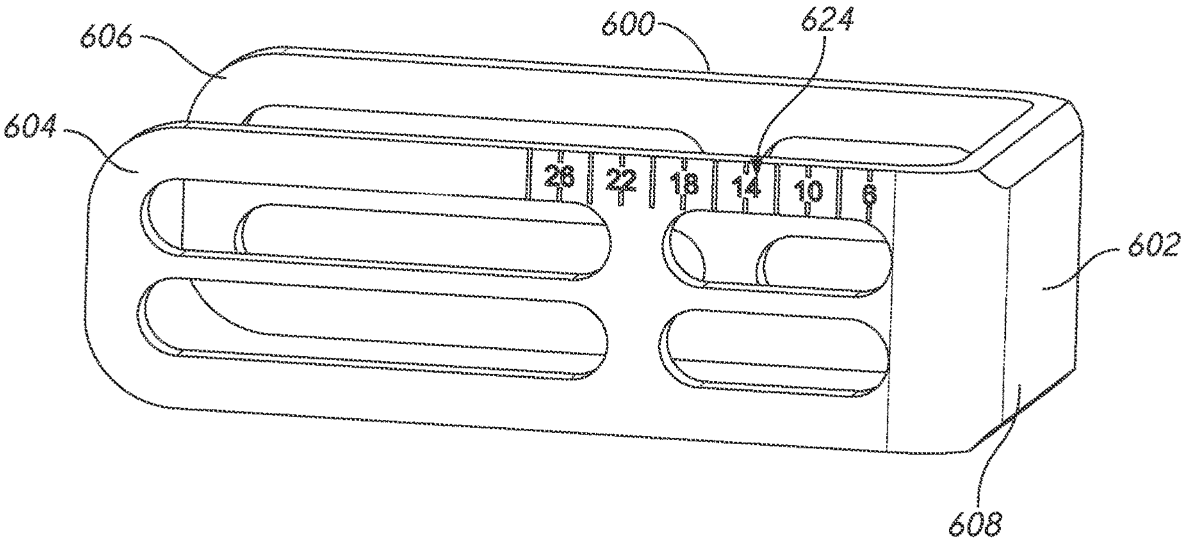
FIG. 16A illustrates a view of a moveable interface of the femoral preparation and knee distraction system of FIG. 13A.

FIG. 16A illustrates a moveable interface 600. The moveable interface 600 can be configured to slide relative to the mounting block 522. In some embodiments, the moveable interface 600 can include a surface 602 configured to abut the shin of the patient. In some embodiments, the surface 602 of the moveable interface 600 can be configured to abut an anatomical landmark. In some embodiments, the surface 602 of the moveable interface 600 can include a portion configured to engage another portion of the anatomy of the patient. The moveable interface 600 can include any shape to allow the moveable interface 600 to move or slide relative to the mounting block 522. The moveable interface 600 can include one or more sides 604, 606, 608. The moveable interface 600 can include two parallel sides 604, 606. The moveable interface 600 can include a front side 608 to connect the two parallel sides. The front side 608 can include the surface 602. The moveable interface 600 can include a U-shaped configuration. The moveable interface 600 can have one or more flat surfaces. In the illustrated embodiments, the moveable interface 600 can include three flat side surfaces. In the illustrated embodiments, the moveable interface 600 can include three outer surfaces including two side outer surfaces and a front outer surface. The front outer surface can be configured to contact the anatomy of a patient.

Figure 16B:
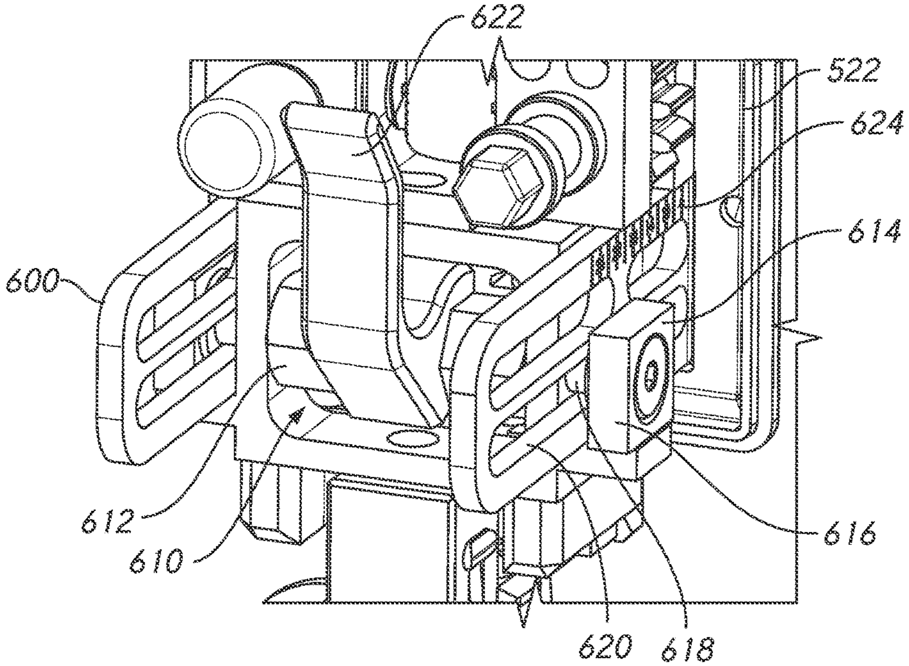
FIG. 16B illustrates a view of a moveable interface lock of the femoral preparation and knee distraction system of FIG. 13A.

In FIG. 16B, the front cover of the mounting block 522 is removed for illustration of the internal contents of the block. The moveable interface 600 can stabilize the mounting block 522 relative to the tibia. The moveable interface 600 can be located at least partially within the mounting block 522. In some embodiments, the moveable interface 600 can extend from the mounting block 522 to allow translation of the moveable interface 600 relative to the mounting block 522. FIG. 16B illustrates one positional relationship between the moveable interface 600 and the mounting block 522. The moveable interface 600 can be configured to slide within the mounting block 522.

FIG. 16B illustrates a moveable interface lock 610 associated with the moveable interface 600. The moveable interface lock 610 can be located at least partially within the mounting block 522. The moveable interface lock 610 can include a turnbuckle 612 which includes two segments having opposite threads. Each end of the turnbuckle 612 engages a threaded end of a shoulder screw 614. The shoulder screw 614 can include a head 616 and a shaft 618. The head 616 of the shoulder screw 614 can be located adjacent to the moveable interface 600. In some embodiments, the shaft 618 of the shoulder screw 614 can be inserted through a slot 620 in the moveable interface 600 to engage the turnbuckle 612. The head 616 of the shoulder screw 614 can be located adjacent to an outer surface of the moveable interface 600.

The turnbuckle 612 can include a handle 622 for actuation of the turnbuckle 612 by the user. When the user translates the handle 622, the turnbuckle 612 can rotate. The rotation of the turnbuckle 612 draws each shoulder screw 614 toward the turnbuckle 612. The rotation of the turnbuckle 612 draws each shoulder screw 614 against the moveable interface 600. The frictional interference between the shoulder screws 614 and the moveable interface 600 can reduce or prevent movement of the moveable interface 600. Other configurations of locking the moveable interface 600 are contemplated. In some embodiments, only one shoulder screw 614 can be utilized to lock the moveable interface 600. In some embodiments, only one point of contact can be utilized to lock the moveable interface 600. In some embodiments, two or more points of contact can be utilized to lock the moveable interface 600.

In some embodiments, the moveable interface 600 can be configured to slide in a single plane. The moveable interface lock can prevent movement in the plane when the shoulder screws 614 engage the moveable interface 600. In the illustrated embodiments, two shoulder screws 614 are utilized but other configurations are contemplated (e.g., one shoulder screw, three shoulder screws, four shoulder screws, six shoulder screws, etc.). In the illustrated embodiments, one shoulder screw 614 engages each side of the moveable interface 600. As the shoulder screws 614 tighten toward the turnbuckle 612, the shoulder screws 614 provide a clamping force on the moveable interface 600. Other mechanisms to reduce or prevent sliding of the moveable interface 600 are contemplated.

The moveable interface 600 can be translated relative to the mounting block 522 prior to inserting the tibial baseplate 514. The moveable interface 600 can limit insertion depth of the tibial baseplate 514. The moveable interface 600 can be translated relative to the mounting block 522 after inserting the tibial baseplate 514. The moveable interface 600 can provide a measurement of the depth of insertion of the tibial baseplate.

The moveable interface 600 can include one or more markings 624. The marking 624 can indicate length or extension of the moveable interface 600. The marking 624 can indicate an insertion depth of the system 510. The marking 624 can indicate an insertion depth of the tibial baseplate 514. The marking 624 can include a scale. The marking 624 can include a machine readable scale. The marking 624 can include a scale visible to the user. The mounting block 522 can include indicia, such as an arrow, to direct the user visually toward the marking 624. As the moveable interface 600 translates toward the leg of the user, the marking 624, such as numbers on a scale, can become visible to the user. In some embodiments, the marking 624 can be over a range of from about 0 mm to 30 mm. The marking 624 can include a distance measurement of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, including a range of two or more of the foregoing values, etc.

2. Femoral System

Figure 17A:
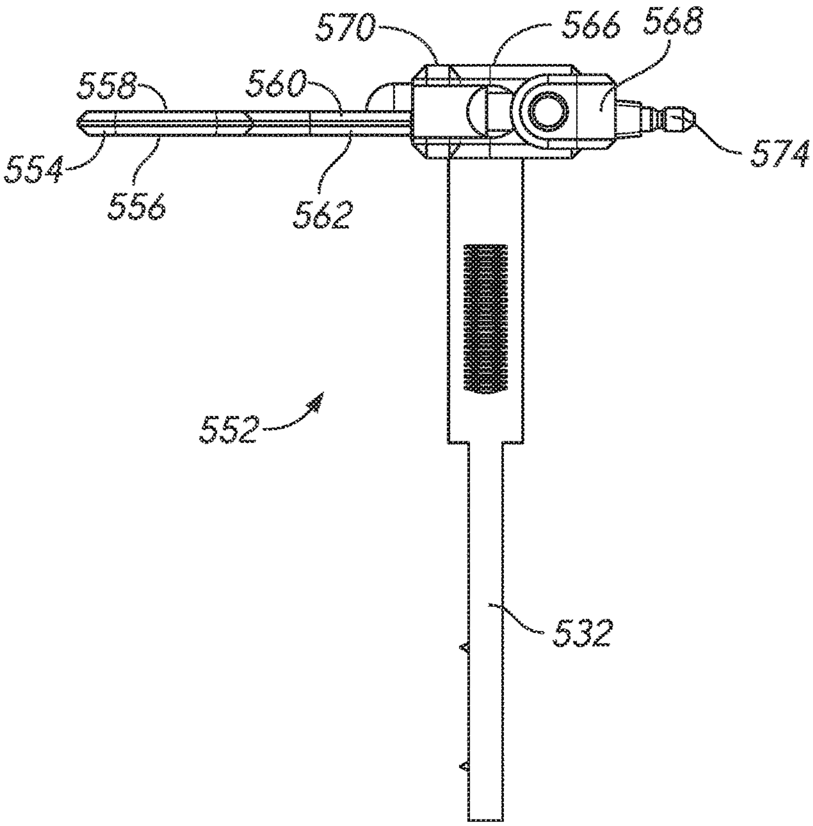
FIGS. 17A-17B illustrate views of a femoral system of the femoral preparation and knee distraction system of FIG. 13A.
Figure 17B:
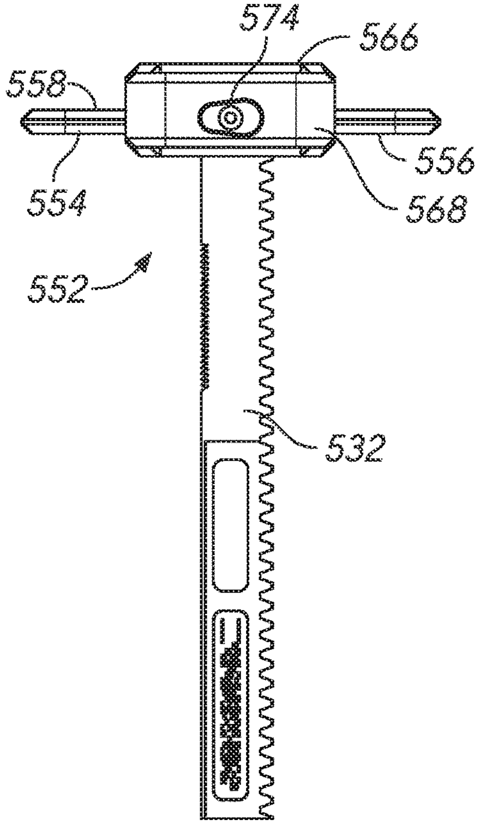

FIGS. 17A and 17B illustrate the femoral system 552. The femoral system 552 can include any of the features of the femoral systems described herein including femoral system 352. The femoral system 552 can include a femoral baseplate 554. The femoral baseplate 554 can comprise a first surface 558 configured to be positioned relative to a portion of the femur. For example, the first surface 558 of the femoral baseplate 554 can be configured to engage the bottom of a bony landmark, such as for example a femoral condyle. The femoral baseplate 554 can include a second surface 556, opposite the first surface 558 positioned toward the tibia.

The femoral system 552 can include an extension member 560. In the some embodiments, the extension member 560 can be generally straight. The femoral system 552 can include an interface 568. The extension member 560 can span between the interface 568 and the femoral baseplate 554. The interface 568 can include a pin or pivot. The interface 568 can allow rotation of the extension member 560 relative to the tibial baseplate 514. The interface 568 can allow rotation of the femoral baseplate 554 relative to the tibial baseplate 514. The interface 568 can be positioned in the middle of the femur and/or tibia. The interface 568 can be aligned with an anatomical feature, such as the intercondylar notch, Whiteside's Line, or another visible landmark indicating or related to the mechanical axis of the femur. In some embodiments, the femoral baseplate 554 and the interface 568 can be rotationally coupled such that rotation of the femoral baseplate 554 causes corresponding rotation of the interface 568. In some embodiments, the femoral baseplate 554 and the interface 568 can be rotationally coupled via the extension member 560.

The femoral system 552 can include a post mount 566. The extension member 560 can position the post mount 566 away from the knee joint. The femoral system 552 can include the post 532 described herein. In some embodiments, the post mount 566 can be coupled to the post 532. In some embodiments, the post mount 566 can be integrally or monolithically formed with the post 532. In some embodiments, the post mount 566 and the post 532 form a unitary structure. The translation of the post 532 can cause corresponding translation of the post mount 566 as described herein. The translation of the post 532 can cause corresponding translation of the femoral baseplate 554. The translation of the post 532 can cause corresponding translation of the extension member 560. The translation of the post 532 can cause corresponding translation of the interface 568. The translation of the post 532 can cause corresponding translation of the other components of the femoral system 552.

In some embodiments, the extension member 560 can extend through the post mount 566. As described herein, the extension member 560, the femoral baseplate 554, and the interface 568 can form a unitary structure such that rotation of the femoral baseplate 554 causes corresponding rotation of the interface 568. The post mount 566 can be coupled to the extension member 560 to allow rotation of the extension member 560 relative to the post mount 566. The post mount 566 can be coupled to the femoral baseplate 554 via the extension member 560. The post mount 566 can be coupled to the femoral baseplate 554 to allow rotation of the femoral baseplate 554 relative to the post mount 566. The post mount 566 can be coupled to the interface 568 to allow rotation of the interface 568 relative to the post mount 566.

The post mount 566 can include a mounting feature 570. The mounting feature 570 can allow one or more guides or other instruments to mount to the system 510. The mounting feature 570 can be parallel to the tibial baseplate 514. The mounting feature 570 can be coupled to the post 532 via the post mount 566. In some embodiments, the mounting feature 570 can remain in position as the femoral baseplate 554 rotates. The mounting feature 570 can be decoupled from the rotation of the extension member 560. The mounting feature 570 can be decoupled from the rotation of the femoral baseplate 554.

The interface 568 can include a second coupler 574. The second coupler 574 can be configured to couple with the surgical orientation device 14 and/or the reference sensor device 16. The second coupler 574 can include any of the features of the couplers described herein. In some embodiments, the second coupler 574 can be positioned on a front surface of the interface 568. In some embodiments, the second coupler 574 can be positioned such that the longitudinal axis of the second coupler 574 aligns or is parallel to the femoral baseplate 554.

Referring back to FIG. 13E, in some embodiments, as the femoral baseplate 554 rotates relative to the tibial baseplate 514, the interface 568 rotates relative to the tibial baseplate 514. In some embodiments, as the femoral baseplate 554 rotates relative to the tibial baseplate 514, the surgical orientation device 14 rotates relative to the tibial baseplate 514. In some embodiments, as the femoral baseplate 554 translates relative to the tibial baseplate 514 via the post 532, the interface 568 translates via translation of the post mount 566. In some embodiments, as the femoral baseplate 554 translates relative to the tibial baseplate 514 via the post 532, the surgical orientation device 14 translates relative to the tibial baseplate 514. FIG. 13E shows a perspective view of the system 510.

The femoral system 552 can include a bracket 576. The second coupler 574 can be configured to couple with the bracket 576. The surgical orientation device 14 can be configured to couple with the bracket 576. The bracket 576 can include an additional or alternative coupler as described herein.

Figure 18A:
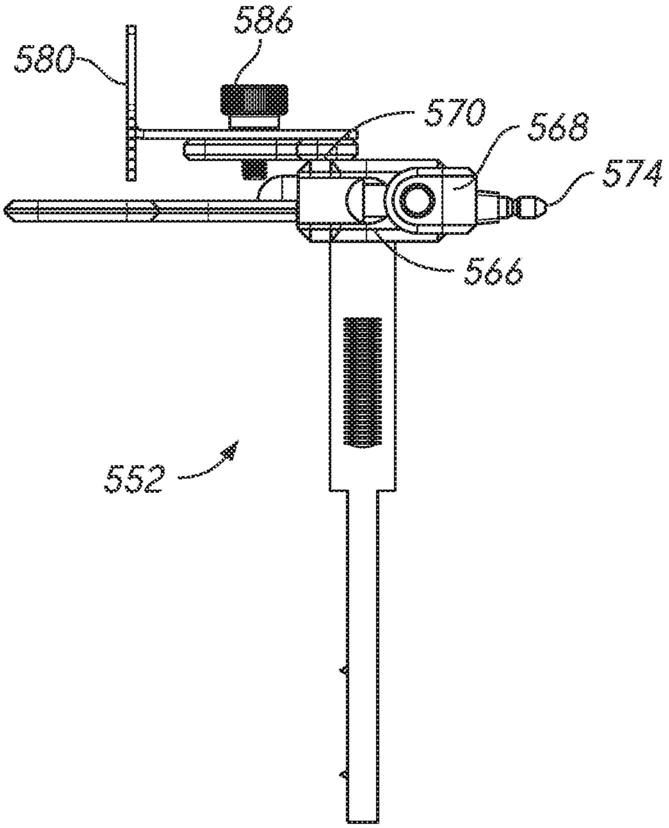
FIGS. 18A-18B illustrate views of a resection guide coupled with the femoral system of FIG. 17A-17B.
Figure 18B:
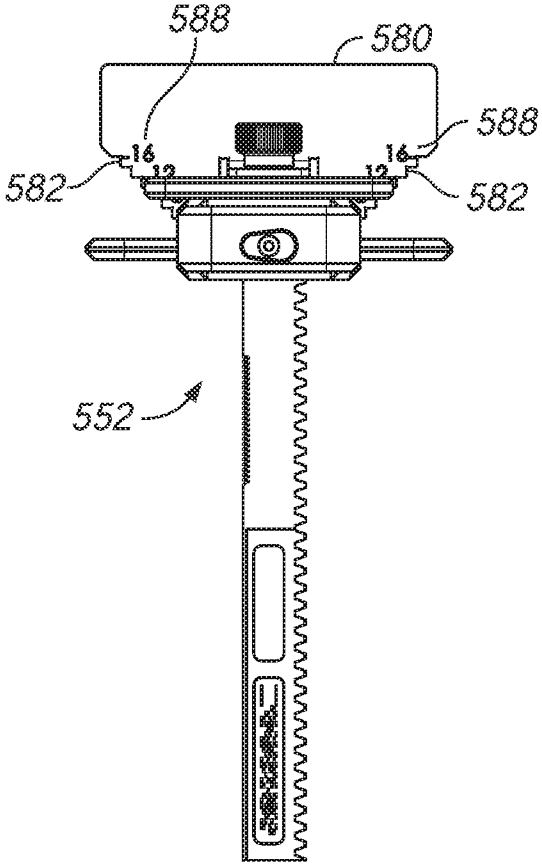

As shown in FIGS. 13E, 18A, and 18B, femoral system 552 can comprise a resection guide 580. The post mount 566 can include the mounting feature 570. The mounting features 570 can be recesses or protrusions to couple to the resection guide. The mounting feature 570 can allow a quick connection between the femoral system 552 and the resection guide 580. Other modes of coupling the resection guide 580 to the post mount 566 are contemplated.

The resection guide 580 can include one or more notches 582. In some embodiments, each notch 582 can form a right angle cutout. The notch 582 can extend through the entire resection guide 580. In some embodiments, each notch 582 can form a step on the resection guide 580. While a plurality of notches 582 are shown creating five steps, different numbers, sizes, shapes, and/or locations of notches 582 can also be used. The notches 582 can be in any increment, such as 0.5 mm increments, 1 mm increments, 1.5 mm increments, 2 mm increments, etc. In some embodiments, the notch 582 on the right side of the resection guide 580 corresponds with notch 582 on the left side of the resection guide 580. In some embodiments, each notch 582 is aligned or coaxial with another notch 582.

The resection guide 580 can include one or more markings 588. The marking 588 can indicate a value related to the corresponding notch 582. The marking 588 can indicate a distance measurement related to the notch 582. The markings 588 can range from 8 mm to 16 mm. The markings 588 can indicate a distance of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, or any range of the foregoing measurements. The markings 588 can be used as guides for a femoral cut by indicating a distance from the tibial resection. In some embodiments, the marking 588 on the right side of the resection guide 580 correspond with the marking 588 on the left side of the resection guide 580. In some embodiments, each notch 582 has one marking 588. In some embodiments, each notch 582 has a corresponding notch 582 with the same marking 588.

In some methods, when the system 510 has distracted a distal femoral condyle or condyles in a knee replacement procedure, the user can mark the femur at the notch 582. In some methods, the user can mark a dot on the right side of the resection guide 580 and the user can mark a dot on the left side of the resection guide 580 corresponding notches 582 with the same marking 588. In some methods, the user can mark a line on the right side of the resection guide 580 and the user can mark a line on the left side of the resection guide 580 corresponding notches 582 with the same marking 588. In some methods, the user can mark intersecting lines on the right side of the resection guide 580 and the user can mark intersecting lines on the left side of the resection guide 580 corresponding notches 582 with the same marking 588. In some embodiments, the user can remove the resection guide 580. In some embodiments, the user can connect the markings on the femur to form a line. In some methods, the line can serve as guide for the posterior resection.

The notches 582 can be spaced apart from one another in a pattern or patterns. In some embodiments, the notches 582 can be spaced at incremental steps. The notches 582 can be spaced at regular or irregular intervals. The notches 582 can indicate a distance to the tibial baseplate 514 via the markings 588. The notches 582 can indicate a distance to the resected tibial surface. In some embodiments, one or more parallel rows of notches 582 are provided. The rows can be parallel to the tibial baseplate 514 and/or the resected tibial surface. The one or more parallel rows of notches 582 can allow the user to mark the line for the posterior resection, as described herein. The one or more parallel rows of notches 582 can allow the user to mark a resection line at a known distance from the tibial resection. The one or more parallel rows of notches 582 can be used to ensure that the posterior femoral cut is parallel to the tibial resection.

In some embodiments, the resection guide 580 can provide notches 582 for even measurements (e.g., 8 mm, 10 mm, 12 mm, 14 mm, 16 mm etc.). In some embodiments, the resection guide 580 can provide notches 582 for odd measurements (e.g., 7 mm, 9 mm, 11 mm, 13 mm, 15 mm, 17 mm etc.). The resection guide 580 can include a first portion extending in a first direction. The resection guide 580 can include a second portion extending in a second direction, the second direction different than the first direction. In some embodiments, the resection guide 580 has two portions which are perpendicular or substantially perpendicular. The first portion can be configured to be adjacent to the femur and the second portion can be configured to extend away from the femur. The first portion and the second portion can be substantially flat or plate-like. The resection guide 580 can be L-shaped. The second portion can include a slot 584 configured to accept a thumbscrew 586. The thumbscrew 586 can removably extend the length of the resection guide 580. The thumbscrew 586 can allow the user to move the resection guide 580 against the femur.

The resection guide 580 can include a portion to engage the mounting feature 570 of the post mount 566. The resection guide 580 can couple to the mounting feature 570 of the post mount 566 such that translation of the post 532 causes corresponding translation of the resection guide 580. The system 510 can translate such that the resection guide 580 remains parallel to the tibial baseplate 512. The resection guide 580 can be a modular device. The resection guide 580 can be coupled and decoupled to the mounting feature 570 during the procedure as needed.

Other guides are contemplated. The system 510 can be utilized with any guide described herein. The system 510 can be utilized with a drill guide to facilitate placements of a pin or pins into the distal femur. In some embodiments, the system 510 can include a plurality of resection guides configured to couple to the mounting feature 570. In some embodiments, the plurality of resection guides can include different notches to enable different posterior resection cuts. Other devices can be mounted to the mounting feature 570. Other configurations of coupling the resection guide 580 to the system 510 are contemplated.

Referring to FIGS. 13E and 18A, the resection guide 580 can be maintained in a rotational orientation relative to the tibial baseplate 514. The resection guide 580 can be coupled or decoupled from the mounting features 570. The mounting features 570 can be coupled to the post mount 566. In some embodiments, the post mount 566 can maintain the position of the resection guide 580 relative to the tibial baseplate. The post mount 566 is coupled to the post 532 in a manner to reduce or prevent rotation of the post mount 566 relative to the post 532. The post 532 is coupled to the tibial baseplate 514 via the tibial mounting block 522 in a manner to reduce or prevent rotation of the post 532 relative to tibial baseplate 514. The resection guide 580 can be rotationally stabilized relative to the tibial baseplate 514. The resection guide 580 can be rotationally coupled to the tibial baseplate 514. The resection guide 580 can be parallel to the tibial baseplate 514. The resection guide 580 can be parallel to the tibial resection.

Referring to FIGS. 13E and 18A, the femoral baseplate 554 can rotate relative to the tibial baseplate 514. The femoral baseplate 554 can be coupled to the interface 568. The surgical orientation device 14 can be coupled to the interface 568. The surgical orientation device 14 can measure the rotation of the femoral baseplate 554. In some embodiments, the femoral baseplate 554 can rotate relative to the resection guide 580. In some embodiments, the femoral baseplate 554 can rotate relative to post mount 566. In some embodiments, the femoral baseplate 554 can rotate relative to the post 532.

The resection guide 580 can be rotationally decoupled from the femoral baseplate 554. The femoral baseplate 554 can be at any angle relative to the resection guide 580. The femoral baseplate 554 can be at any angle relative to the tibial resection. In some embodiments, the rotation of the femoral baseplate 554 is independent of the positioning of the resection guide 580. The resection guide 580 can translate relative to the tibial baseplate 514. The resection guide 580 can translate as the post 532 translates. The system 510 can provide an alignment of the resection guide 580 relative to the tibial resection as described herein.

3. Distraction Overview

Figure 19A:
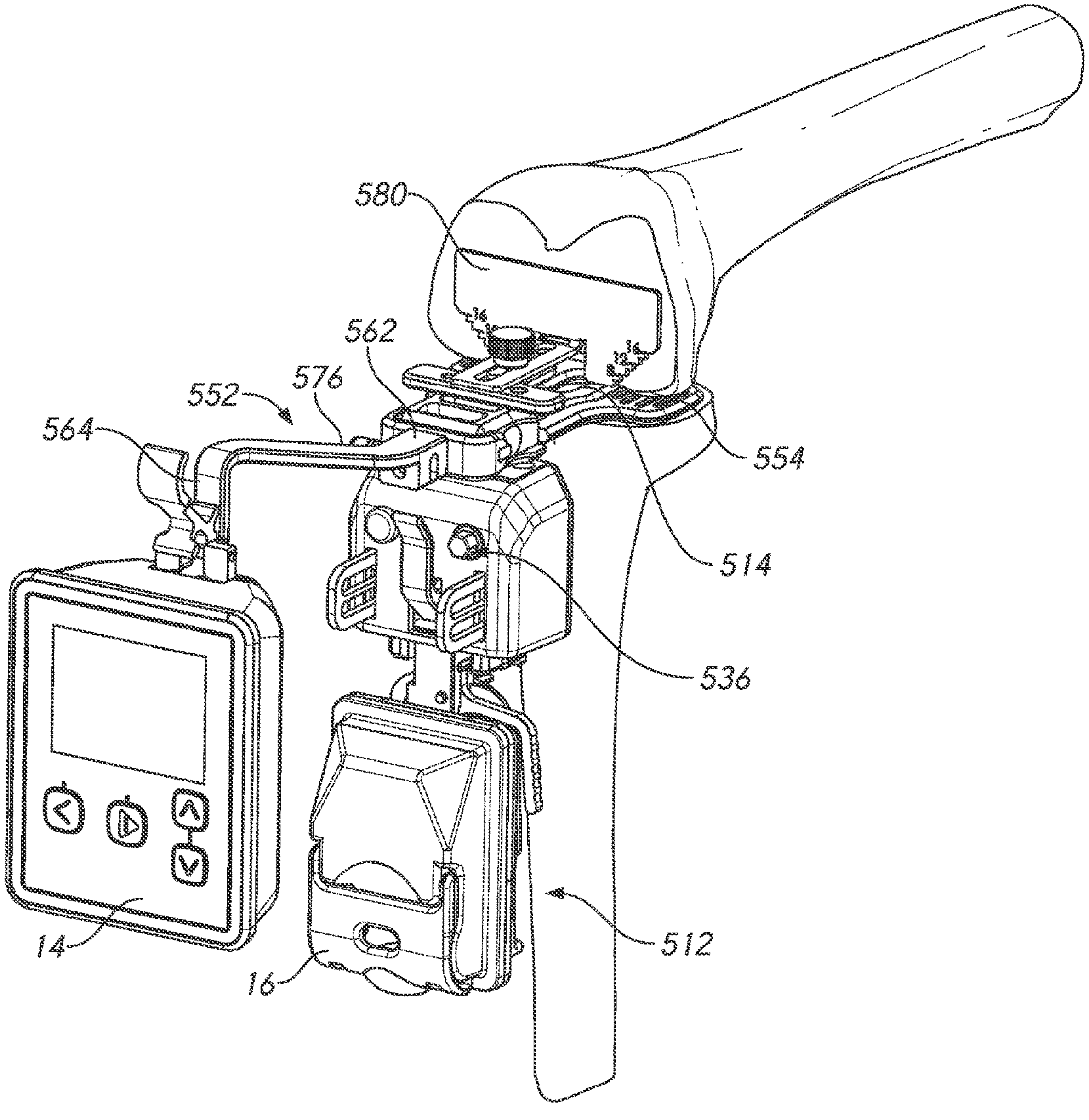
FIG. 19A illustrates the femoral preparation and knee distraction system of FIG. 13A disposed in a joint space of a schematic knee joint placed in flexion.

FIG. 19A-19H illustrate additional views of the system 510 coupled to the tibia and femur of a patient. FIG. 19A illustrates a perspective view of a position of the system 510.

Figure 19B:
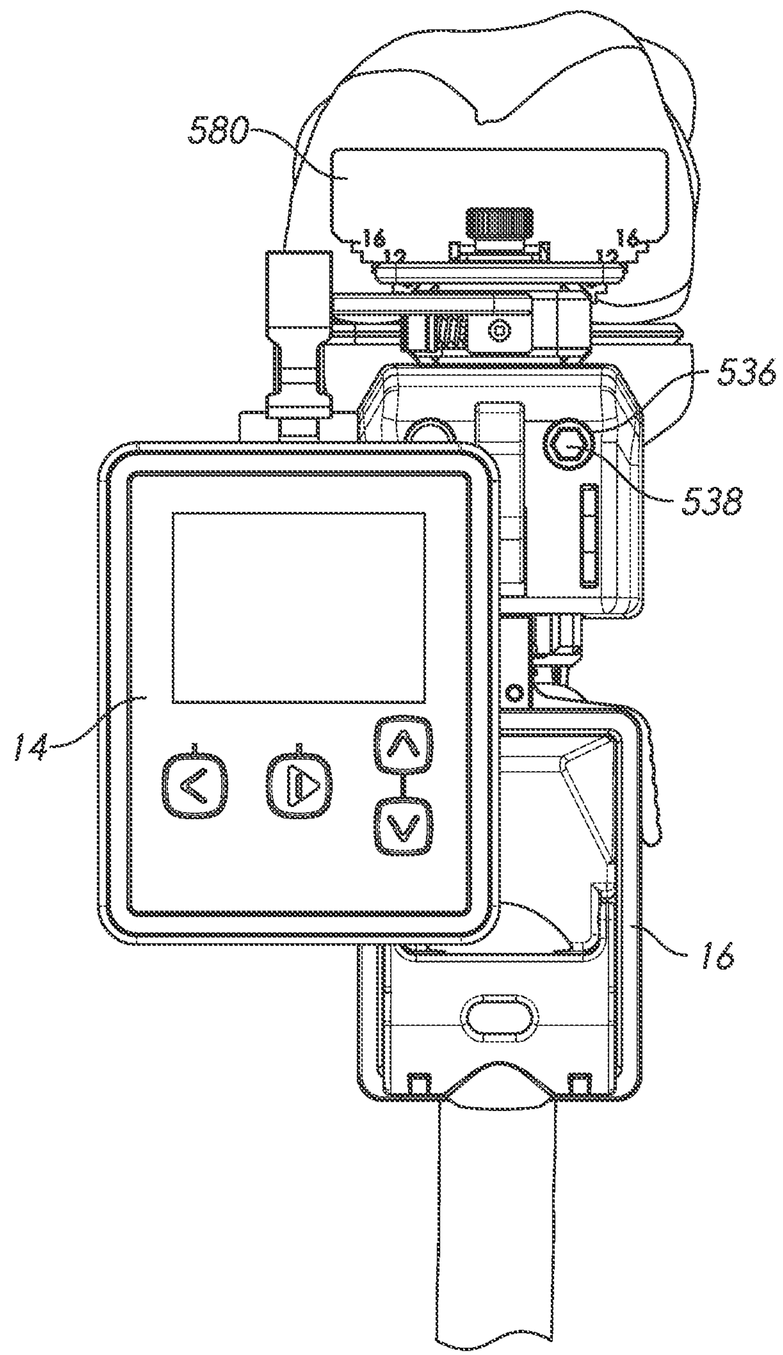
FIG. 19B illustrates a front view the femoral preparation and knee distraction system of FIG. 13A disposed in a joint space of a schematic knee joint placed in flexion.

FIG. 19B illustrates a front view of a position of the system 510. The femoral system 552 can include the bracket 576 as described herein. The bracket 576 can enable the user to view the joint space. The bracket 576 can move the surgical orientation device 14 downward relative to the femoral baseplate 554. The surgical orientation device 14 can be located out of the joint space. The user can view the tibial baseplate 514 and the femoral baseplate 554. The bracket 576 can offset the surgical orientation device 14 to the side.

In some embodiments, the bracket 576 can be generally L-shaped. The bracket 576 can include a first portion 562 that extends from the second coupler 574. The first portion 562 can extend in a first direction. The bracket 576 can include a second portion 564. The second portion 564 can extend in a second direction; the second direction can be different from the first direction. In some embodiments, the first portion 562 can extend horizontally. In some embodiments, the second portion 564 can extend vertically. In some embodiments, the second portion 564 can extends perpendicularly or generally perpendicularly from the first portion 562. In some embodiments, the first portion 562 is straight or substantially straight. In some embodiments, the first portion 562 is non-linear, for instance having a straight segment and a diagonal segment. In some embodiments, the second portion 564 is straight or substantially straight. In some embodiments, the first portion 562 can be integrally or monolithically formed with the second portion 564. In some embodiments, the first portion 562 can extend in a diagonal from the second coupler 574 to provide an offset. In some embodiments, the first portion 562 can extend straight from the second coupler 574.

An advantage can be that the bracket 576 can position the surgical orientation device 14 below the tibial resection. An advantage can be that the bracket 576 can position the surgical orientation device 14 out of a field of view of the joint space, e.g. enhancing visibility from the perspective of FIG. 19A. An advantage can be that the bracket 576 can position the surgical orientation device 14 offset from the reference sensor device 16. An advantage is that the bracket 576 can position the surgical orientation device 14 offset from the interface 538 of the adjustment device 536. An advantage is that the bracket 576 can position the surgical orientation device 14 below the resection guide 580. The surgical orientation device 14 can be positioned to allow a line of sight to the resection guide 580. Other configurations are contemplated.

In some embodiments, the longitudinal axis of the reference sensor device 16 can align with the longitudinal axis of the tibia. The axis of the tibia can be perpendicular to the tibial resection. In some embodiments, the reference sensor device 16 can align with a mechanical axis associated with the knee joint, e.g., of the tibia or the leg. In some embodiments, the longitudinal axis of the surgical orientation device 14 can be offset from the longitudinal axis of the tibia. In the illustrated embodiment, the surgical orientation device 14 can be offset from a mechanical axis associated with the knee joint, e.g., of the tibia or the leg. The longitudinal axis of the surgical orientation device 14 and the longitudinal axis of the reference sensor device 16 can be parallel. The longitudinal axis of the surgical orientation device 14 and the longitudinal axis of the reference sensor device 16 can be offset in the coronal plane. The longitudinal axis of the surgical orientation device 14 and the longitudinal axis of the reference sensor device 16 can be offset in the sagittal plane. The longitudinal axis of the surgical orientation device 14 and the longitudinal axis of the reference sensor device 16 can be offset in the traverse plane.

Figure 19C:
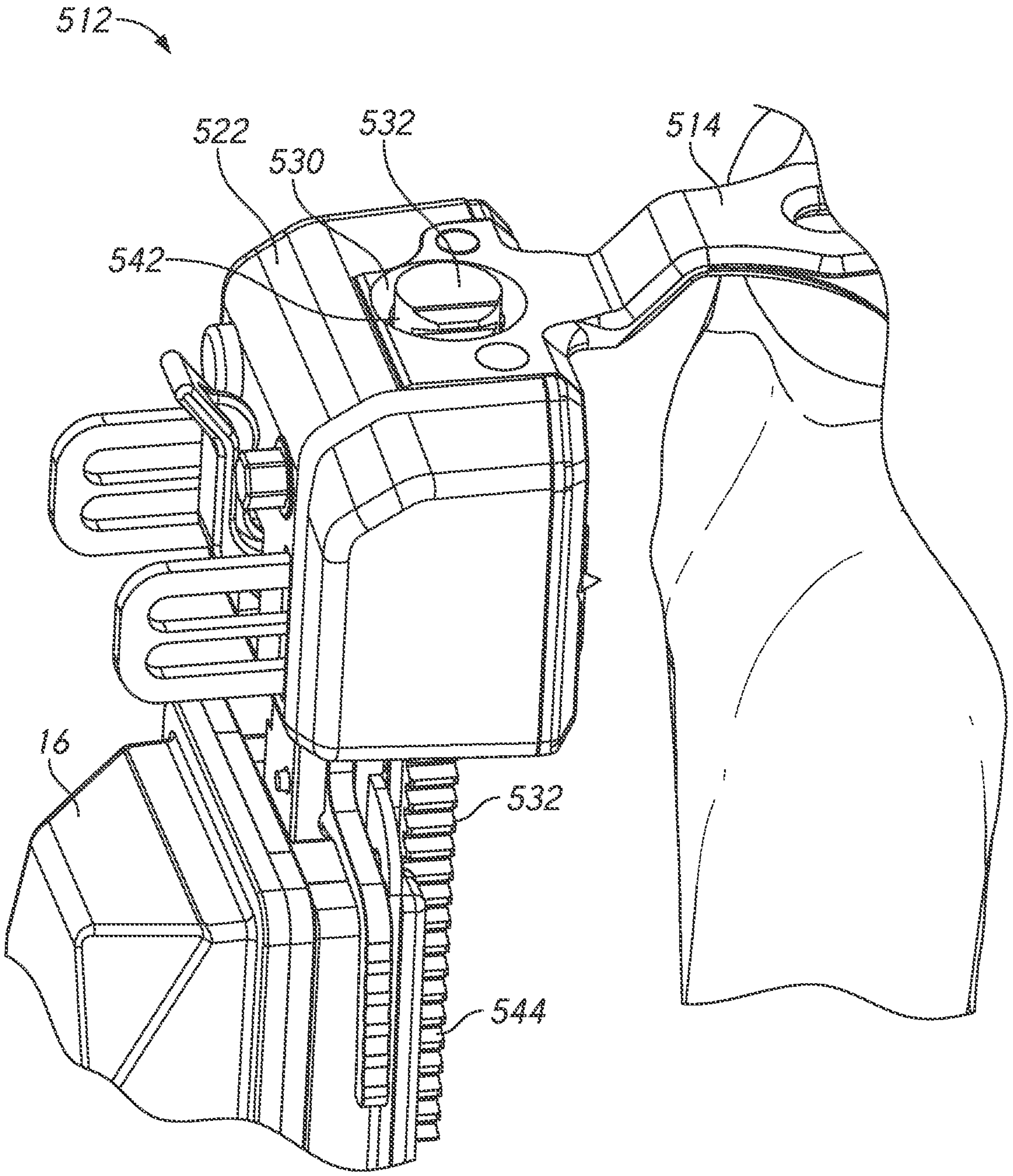
FIG. 19C illustrates a subsystem of the femoral preparation and knee distraction system of FIG. 13A including the tibial system of FIGS. 14A-14B.

FIG. 19C illustrates a perspective view of a position of the tibial system 512 and the post 532. As described herein, the upper portion 542 of the post 532 can have a substantially round or circular cross-sectional shape and the guide portion 530 of the mounting block 522 can have a corresponding substantially round or circular cross-sectional shape. The round or circular cross-sectional shape can allow for more precision in placement of the markings 540 relative to the camera 344 of the reference sensor device 16. The round or circular cross-sectional shape can allow the tibial baseplate 514 and the femoral baseplate 554 to maintain alignment during distraction. The round or circular cross-sectional shape can allow a tighter tolerance between components of the system 510. The lower portion 546 of the post 532 can have any cross-sectional shape.

Figure 19D:
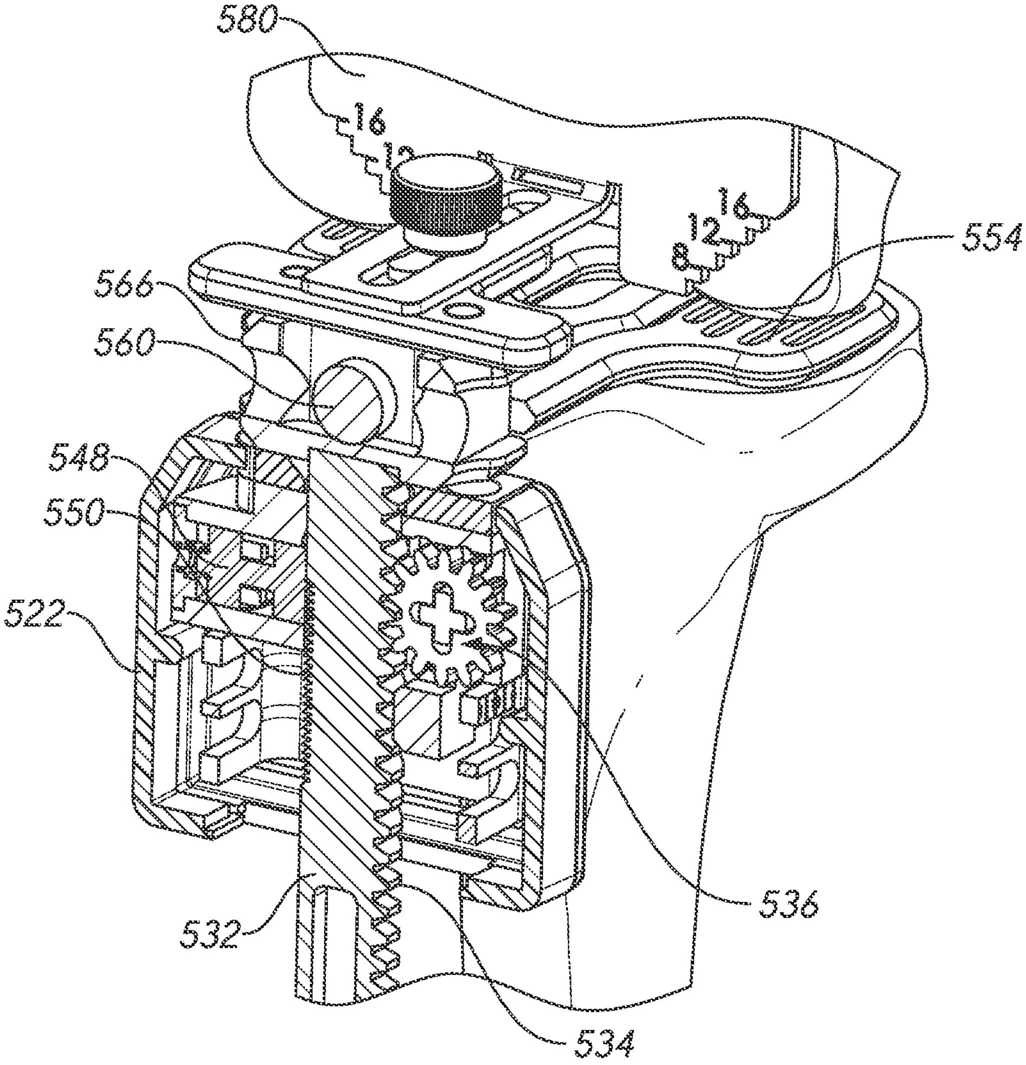
FIG. 19D illustrate a subsystem of the femoral preparation and knee distraction system of FIG. 13A including the tibial system of FIGS. 14A-14B.

FIG. 19D illustrates a cross-sectional view inside the mounting block 522. The adjustment device 536 and the catch 548 can be diametrically opposed. The adjustment device 536 and the catch 548 can be spaced apart. The adjustment device 536 can be configured to engage the rack 534 which can have larger gears than the ratchet 550 engaged by the catch 548. The adjustment device 536 can allow application of force. The force exerted can be in the range of 150 N to 200 N. The adjustment device 536 and the rack 534 can be configured to exert any force sufficient for joint distraction. The teeth on adjustment device 536 and the teeth of the rack 534 can be configured to exert a desired force on the joint. The catch 548 can allow fine resolution positioning. The increments between teeth on the ratchet 550 can be smaller than the rack 534. The teeth can be in 1 mm increments on the ratchet 550. The catch 548 can maintain the position of the post 532 when the user stops actuating the adjustment device 536.

FIG. 19D illustrates the connection between other components of the system 510. The post 532 can be coupled to the post mount 566. Translation of the post 532 can cause corresponding translation of the post mount 566. The resection guide 580 can be coupled to the post mount 566 via the mounting feature 570. In some embodiments, rotation is limited or prevented between the post 532 and the post mount 566. In some embodiments, rotation is limited or prevented between the post 532 and the resection guide 580. In some embodiments, the post 532 and the post mount 566 can function as a unit. In some embodiments, the post 532 and the post mount 566 are integrally formed. In some embodiments, the resection guide 580 is removably mounted to the mounting feature 570 of the post mount 566. In some embodiments, when the resection guide 580 is coupled to the mounting feature 570, the post 532, the post mount 566, and the resection guide 580 form a unitary structure. In some embodiments, the resection guide 580 can be configured only to translate linearly with translation of the post 532.

FIG. 19D illustrates the connection between the extension member 560 and the post mount 566. The extension member 560 can couple to the femoral baseplate 554. The extension member 560 can couple to the interface 568 (see FIG. 17A). Rotation of the femoral baseplate 554 can cause corresponding rotation of the extension member 560. The post mount 566 can allow rotation of the femoral baseplate 554 and the extension member 560 relative to the post mount 566.

Figure 19E:
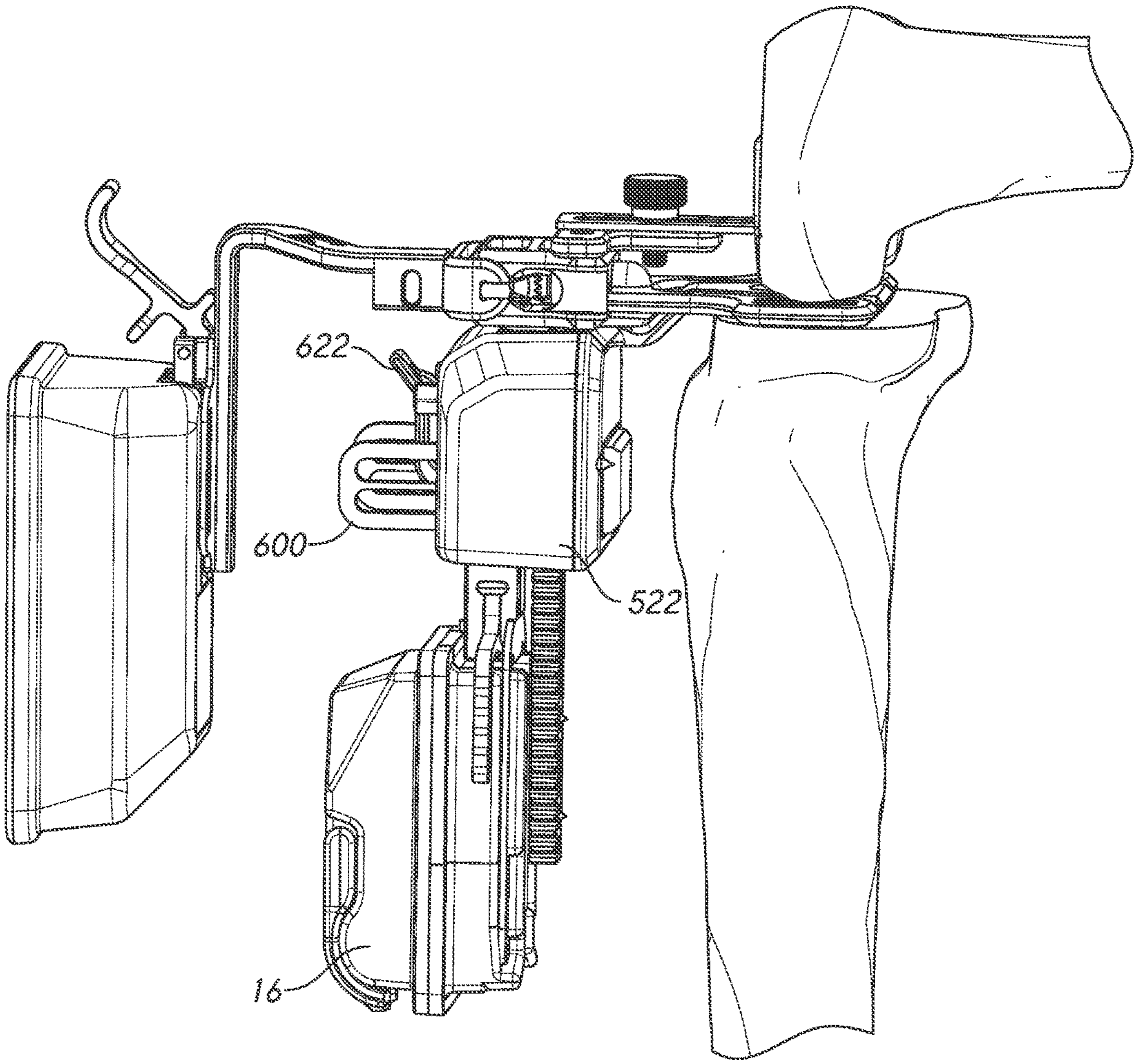
FIG. 19E illustrate a subsystem of the femoral preparation and knee distraction system of FIG. 13A including the moveable interface.
Figure 19F:
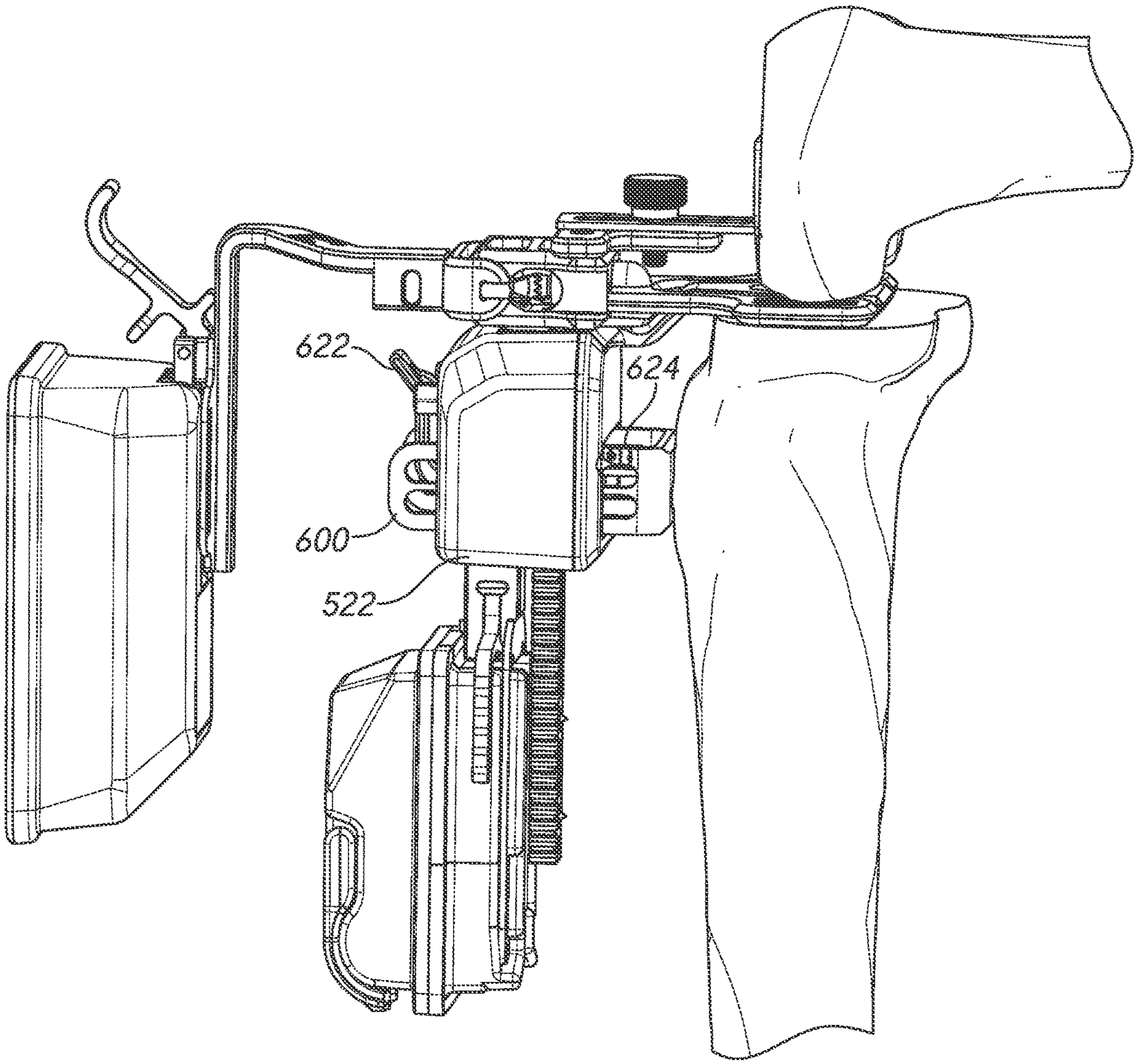
FIG. 19F illustrate a subsystem of the femoral preparation and knee distraction system of FIG. 13A including the moveable interface.

FIGS. 19E and 19F illustrate the tibial system and the moveable interface 600. FIG. 19E illustrates the moveable interface 600 spaced apart from the tibia. FIG. 19F illustrates the moveable interface 600 engaged with the tibia. The moveable interface 600 can include the surface 602 to contact the shin of the user. The moveable interface 600 can be configured to move in the fore and aft direction within the mounting block 522 (corresponding to posterior and anterior movement relative to the patient). The moveable interface 600 can slide in the fore direction to rest against the shin of the patient. The moveable interface lock can be used to reduce or prevent the sliding movement of the moveable interface 600. The moveable interface lock can include the handle 622 which can rotate the turnbuckle 612 within the mounting block 522 as described herein. The frictional force of the moveable interface lock can limit sliding movement of the moveable interface 600.

The moveable interface 600 can include the marking 624. The marking 624 can provide an indication of the insertion depth of the system 510. The moveable interface 600 can limit or prevent further insertion by the interference between the moveable interface 600 and the anatomy of the patient. The moveable interface 600 can increase the stability of the system 510. The moveable interface 600 can provide an additional point of contact between the system 510 and the patient. The moveable interface 600 can limit insertion depth in flexion. The moveable interface 600 can limit insertion depth in extension.

Figure 19G:
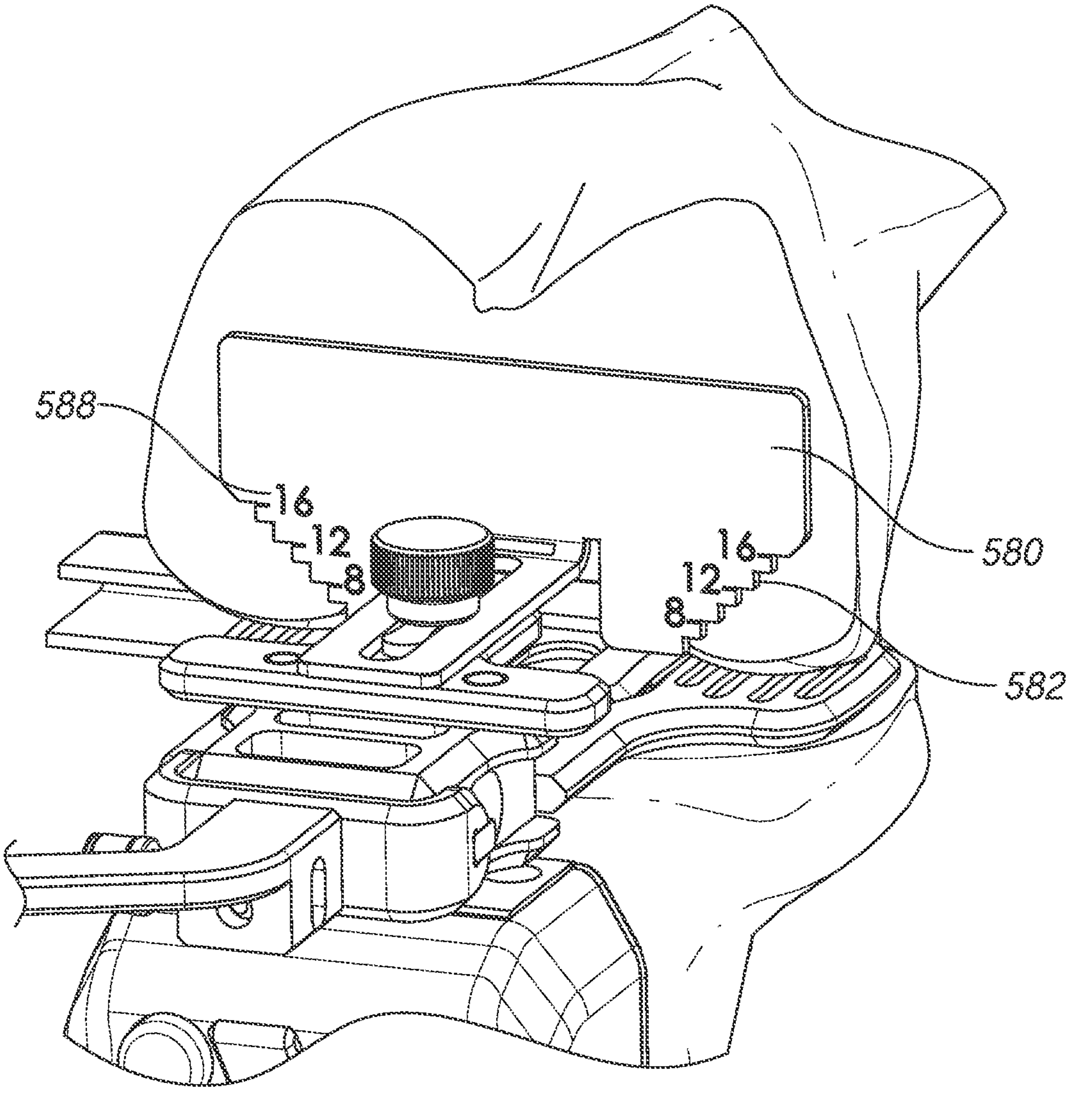
FIG. 19G illustrate a subsystem of the femoral preparation and knee distraction system of FIG. 13A including the resection guide.

FIG. 19G illustrates a perspective view of the one or more notches 582 of the resection guide 580. The notches 582 can indicate the distance to the tibial resection. The resection guide 580 can be a plate configured to rest against the resected femur. Each notch 582 or some of the notches 582 can include a corresponding marking 588. The notches 582 can enable a user to draw a line at the position of the posterior cut. In some methods, the user can mark the femur using one or more notches 582. In some methods, the user can then connect the marks on the femur to form a line. The line can correspond to a resection plane.

Figure 19H:
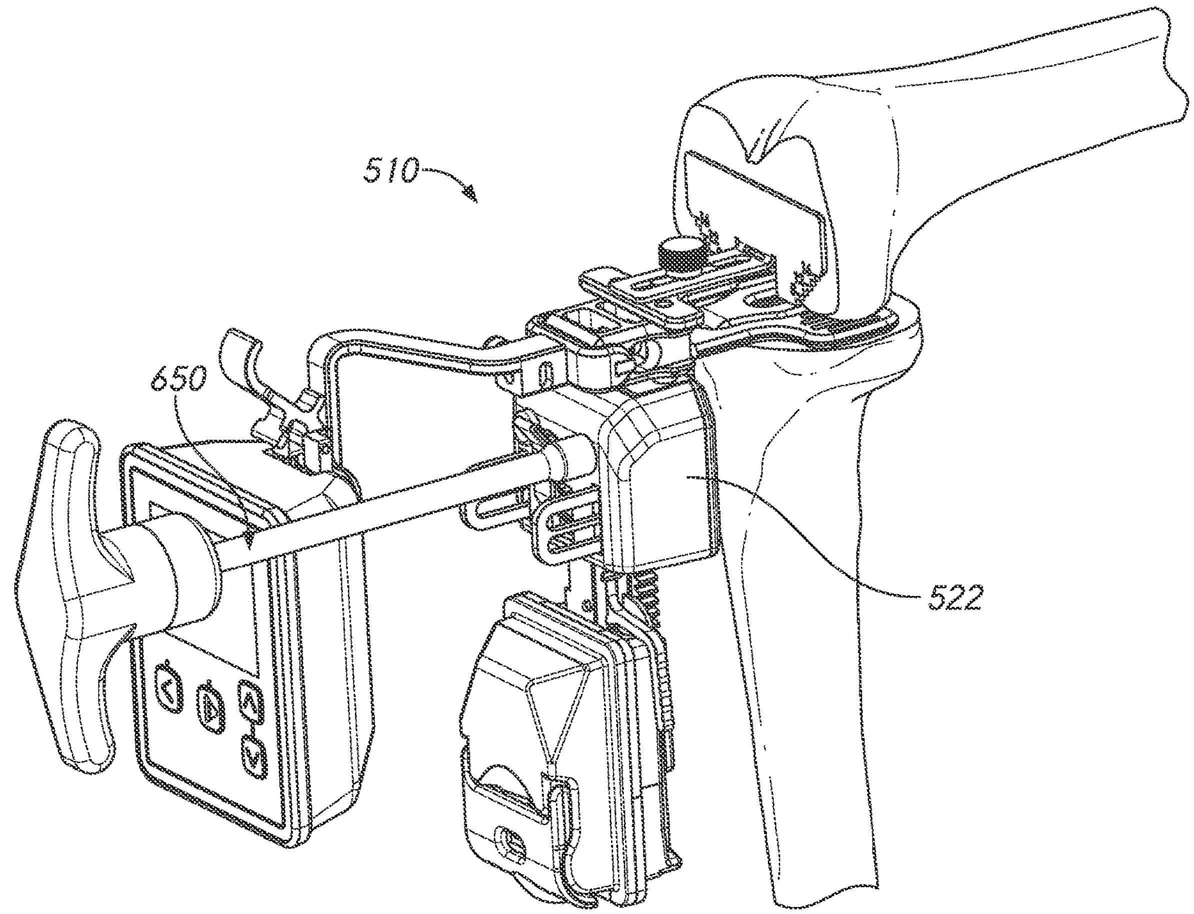
FIG. 19H illustrate a subsystem of the femoral preparation and knee distraction system of FIG. 13A including a torque driver.

FIG. 19H illustrates a perspective view of the system 510 and a torque driver 650. The torque driver 650 can engage the adjustment device 536. The interface 538 of the adjustment device 536 can be located on the mounting block 522. The torque driver 650 can allow rotation of the adjustment device 536. In some embodiments, rotation of the torque driver 650 can cause corresponding rotation of the adjustment device 536. In some embodiments, translation of the torque driver 650 can cause corresponding rotation of the adjustment device 536. In some embodiments, a motion or movement of the torque driver 600 can cause corresponding rotation of the adjustment device 536. While FIG. 19H illustrates a torque driver 650, other drivers are contemplated.

The system 510 can facilitate a posterior resection. The posterior resection can enable the positioning of the implant. The implant manufacturer can supply a guide configured to mount to a femur after the posterior resection. The anterior and/or chamfer cut can be relative to the posterior resection. The drill guide and the positioning of the cutting block can be relative to the posterior resection. The notches 582 can serve to mark the femur for the posterior resection cut. The resection guide 580 can allow the user to mark the femur a certain distance from the tibia resection for the posterior resection cut.

The surgical orientation device 14 can measure the distance for the posterior resection cut. The surgical orientation device 14 and the reference sensor device 16 can be in communication to determine the distraction distance. In some methods, the camera 344 of the reference sensor device 16 can capture a distance measurement from marking 540 of the post 532. In some embodiments, the reference sensor device 16 can transmit the distance measurement to the surgical orientation device 14. In some embodiments, the reference sensor device 16 can transmit the image from the camera 344 to the surgical orientation device 14.

The system 510 can be configured to be inserted within the joint space. In some embodiments, the tibial baseplate 514 can be adjacent to the femoral baseplate 554 during insertion. The surgical orientation device 14 can be coupled with the bracket 576. The reference sensor device 16 can be coupled with the mounting block 522. The femoral system 552 can be moved up and down (e.g. proximally and distally) relative to the tibial system 512 by the adjustment device 536. The adjustment device 536 can be used to distract the femur relative to the tibia. The adjustment device 536 can be actuated by the user to translate the post 532 within the mounting block 522. The catch 548 can maintain the position of the post 532 when the user stops actuating the adjustment device 536. The catch 548 can prevent positional slippage of the adjustment device 536. The movement of the post 532 can cause corresponding movement of the femoral system 552 relative to the tibial system 512. The femoral system 552 translates as a unit with the post 532. By translation of the post 532, the femoral baseplate 554 can be moved relative to the tibial baseplate 514 to increase or decrease a gap therebetween.

In some embodiments, the femoral baseplate 554 can rotate relative to the tibial baseplate 514. The femoral baseplate 554 can rotate in the medial-lateral direction. This rotation can allow the femoral baseplate 554 to engage both femoral condyles, regardless of size or orientation of the femoral condyles or spacing of the femoral condyles. This rotation can allow the femoral baseplate 554 to be inserted through a relatively narrow incision in a low profile orientation, and then rotate within the joint space to engage the femoral condyles.

The surgical orientation device 14 can be coupled to the femoral baseplate 554. The surgical orientation device 14 can provide an indication of the degree of rotation of the femoral baseplate 554. The surgical orientation device 14 can be coupled to the femoral baseplate 554 such that rotation of the femoral baseplate 554 can cause corresponding rotation of the surgical orientation device 14. The surgical orientation device 14 can include a display 26 which can indicate the angle of rotation of the surgical orientation device 14. In some embodiments, the surgical orientation device 14 and the reference sensor device 16 determine the angle of the surgical orientation device 14. In some embodiments, one or more sensors within the surgical orientation device 14 determine the angle of the surgical orientation device 14. As one non-limiting example, one or more sensors can determine position or orientation relative to gravitational zero. The surgical orientation device 14 can measure the angle of the femoral baseplate 554. The angle can correspond to the angle between the femoral baseplate 554 and the tibial baseplate 514.

In some embodiments, the soft tissue around the knee joint can be released. In some embodiments, the soft tissue around the knee joint can be released when the knee is in extension. In some embodiments, the soft tissue around the knee joint can be released when the knee is in extension only. In some embodiments, the soft tissue around the knee joint can be released when the knee is in flexion. In some methods, the user can modify the soft tissue by cutting one or more ligaments. The change in soft tissue can cause a change in the rotation of the femoral baseplate 554. The change in rotation of the femoral baseplate 554 can cause a corresponding change in the rotation of the surgical orientation device 14. The surgical orientation device 14 can display the angle of the surgical orientation device 14 as the surgical orientation device 14 rotates. In some embodiments, the user can release one or more ligaments in the knee joint prior to or during the knee distraction in order to facilitate simultaneous symmetry of the gaps. In some embodiments, the user can release one or more ligaments in the knee joint prior to or during the knee distraction to facilitate mechanical axis alignment. In some embodiments, the user can release one or more ligaments in the knee joint prior to or during the knee distraction to facilitate balancing of the soft tissue and/or ligaments in the knee joint. The user can nick or cut soft tissue to adjust for laxity of the knee joint. In some embodiments, the user performs soft tissue balancing until the femoral baseplate 554 and the tibial baseplate 514 are parallel or approximately parallel when the knee is in extension. In some embodiments, the user performs soft tissue balancing until the femoral baseplate 554 and the tibial baseplate 514 are at a desired angle.

The surgical orientation device 14 and/or the reference device 16 can be configured to measure rotation of the surgical orientation device 14 during soft tissue balancing. The rotation of the surgical orientation device 14 is related to the relative tension in the medial and lateral soft tissue on the medial and lateral sides of the knee joint. The surgical orientation device 14 can display the angle of rotation before soft tissue release and/or during soft tissue release. The surgical orientation device 14 can display this information on the display 26 located within the surgical field. As described herein, the surgical orientation device 14 can be positioned below the joint space. The surgical orientation device 14 can display the angle of femoral rotation. In some embodiments, the surgical orientation device 14 can display the angle of femoral rotation in real-time. In some embodiments, the surgical orientation device 14 can display a static angle of femoral rotation, for instance the angle of femoral rotation at a specific time such as when a button or other user input 28 is activated. In some embodiments, the surgical orientation device 14 can display a dynamic angle of femoral rotation, for instance the angle of femoral rotation as the soft tissue is being manipulated. In some embodiments, the surgical orientation device 14 can display a target angle of femoral rotation. The target can be displayed as a graphical representation, for instance a slide scale or indicia located on a bullseye.

The surgical orientation device 14 and/or the reference device 16 can be configured to measure the distraction distance between the femoral baseplate 554 and the tibial baseplate 514. The camera 344 can capture an image corresponding to the distraction distance or otherwise read the marking 540 on the post 532. The marking 540 can be a scale which can be captured by the camera 344. The image from the camera 344 can be interpreted by either the surgical orientation device 14 or the reference sensor device 16. The surgical orientation device 14 can display the distraction distance on the display 26. In some embodiments, the surgical orientation device 14 can display the distraction distance in real-time. In some embodiments, the surgical orientation device 14 can display a static distraction distance, for instance the distraction distance at a specific time such as when a button or other user input 28 is activated In some embodiments, the surgical orientation device 14 can display a dynamic distraction distance, for instance the distraction distance as the post 532 is moving. In some embodiments, the surgical orientation device 14 can display a target distraction distance. The target can be displayed as graphical representation, for instance a fillable bar of a bar graph, sliding scale, or indicia located on a bullseye.

In some embodiments, the user can make femoral cuts after distraction. The resection guide 580 can be a modular device that can be coupled or decoupled from the mounting features 570. In some embodiments, the resection guide 580 can be rotationally fixed relative to the tibial baseplate 514. In some embodiments, the resection guide 580 can allow the user to make one or more cuts in the femur at an angle selected relative to (e.g., parallel to) the tibial baseplate 514. In some embodiments, the resection guide 580 can allow the user to make one or more cuts in the femur at known distance from the resected tibia. In some embodiments, the cut can be performed when the knee is in flexion.

In some methods of use, the tibia is resected prior to using the system 510. For example, and as described above, a tibial preparation system 210 or other tibial preparation system can be used to resect a portion or portions of the tibia, such that the distal end of the tibia comprises generally a flat plane. In some methods of use, the femur is resected prior to using the system 510. For example, and as described above, a femoral preparation system 10 or other femur preparation system can be used to resect a portion or portions of the femur, such that the distal end of the femur comprises generally a flat plane.

In some embodiments, the system 510 can be used when the knee is in extension. In some methods of use, after completing the tibial resection and the distal femoral resection, the user flexes the knee to 180 degrees and inserts the system 510. In some methods of use, the leg is positioned in full extension (not shown). The tibial baseplate 514 and the femoral baseplate 554 can be inserted into the knee joint and the knee joint can be distracted. The surgical orientation device 14 can measure the distraction distance using one or more sensors. The reference sensor device 16 can measure the distraction distance using one or more sensors. The reference sensor device 16 can measure the distraction distance using the camera 344. The surgical orientation device 14 and/or the reference sensor device 16 can record the distraction distance when the knee is in extension. The surgical orientation device 14 and/or the reference sensor device 16 can store the distraction distance when the knee is in extension for use when the knee is in flexion. The surgical orientation device 14 and the femoral baseplate 554 can rotate based on the tension on the medial and lateral sides of the knee. The user can release ligaments when the knee is in extension based on the angle output of the surgical orientation device 14. The user can release ligaments to decrease the rotation of the femoral baseplate 554. The user can release ligaments so that the femoral baseplate 554 is parallel to the tibial baseplate 514. The user can release ligaments so that the femoral baseplate 554 is at a desired angle relative to the tibial baseplate 514. In some methods, soft tissue release is only performed with the knee in extension.

In some embodiments, the system 510 can be used when the knee is in flexion. In some methods of use, after completing the tibial resection and the distal femoral resection, the user flexes the knee to 90 degrees and inserts the system 510. The tibial baseplate 514 and the femoral baseplate 554 can be inserted into the knee joint and the knee joint can be distracted. The surgical orientation device 14 can measure the distraction distance using one or more sensors. The reference sensor device 16 can measure the distraction distance using one or more sensors. The reference sensor device 16 can measure the distraction distance using the camera 344. The surgical orientation device 14 and/or the reference sensor device 16 can record the distraction distance when the knee is in flexion. The surgical orientation device 14 and/or the reference sensor device 16 can compare the distraction distance when the knee is in extension and flexion. The surgical orientation device 14 and the femoral baseplate 554 can rotate based on the tension on the medial and lateral sides of the knee. The surgical orientation device 14 can display the angle of rotation of the femoral baseplate. The resection guide 580 can be parallel to the tibial resection. After the joint is distracted, the user can mark the resection line for the posterior cut. In some methods, the user can balance the gaps in flexion and extension. In some methods, the user can balance the gaps in flexion and extension by selecting a notch 582 on the resection guide 580 corresponding to the extension gap.

As described herein, the camera 344 can capture an image related to the distraction distance. The distance measurement can correspond to the distraction distance between the tibia and the femur. The system 510 can calculate the anterior-posterior shift to equalize the flexion gap and the extension gap. In some embodiments, the surgical orientation device 14 can display the distraction distance in extension and the distraction distance in flexion. In some embodiments, the surgical orientation device 14 can display a static distraction distance from measurements taken while the knee was in extension and a dynamic distraction distance when the knee is in flexion. In some methods, the user can compare the distraction distances in extension and in flexion. In some methods, the surgical orientation device 14 can output the difference in the extension gap and the flexion gap.

In some knee joint procedures, a posterior femoral cut (PFC) is made while the knee is in flexion. In some methods of use, the user can utilize the resection guide 580 to perform the posterior cut. The resection guide 580 can include notches corresponding to different gap measurements. The resection guide 580 can provide a guide to mark the posterior resection to provide the appropriate anterior-posterior shift. The anterior-posterior shift can be based on the anterior-posterior shift calculated by the surgical orientation device 14. The anterior-posterior shift can be based on the anterior-posterior shift determined by comparing the distraction distance in extension and the distraction distance in flexion. The anterior-posterior shift can be difference between the gap in extension and flexion.

The user can select a notch 582 which corresponds to the measured gap in extension. The notch 582 can include a corresponding marking 588 which can be a distance measurement. For instance, if the extension gap is 8 mm, then the user can select a notch 582 corresponding to a flexion gap of 8 mm. The user can select from different parallel rows of notches 582 corresponding to different distances. The user can use a row of notches 582 to make two marks on the femur. In some methods, the user can remove the resection guide 580 and interconnect the marks to form a line. The user can use the marks and/or the line to make the posterior femoral cut. The anterior cut can be made relative to the posterior cut. The chamfer cut can be made relative to the posterior cut. One or more additional cuts can be made based on the posterior femoral cut.

The system 510 can be utilized for soft tissue balancing in extension and/or flexion. The surgical orientation device 14 can display the rotation angle of the surgical orientation device 14. The rotation angle can be relative to the reference sensor device 16. The rotation angle can be relative to gravitational zero, or any other vertical or horizontal vector. The surgical orientation device 14 can display the rotation angle of the surgical orientation device 14. The surgical orientation device 14 can display the rotation angle of the surgical orientation device 14 relative to a vertical vector. The surgical orientation device 14 can display the rotation angle of the surgical orientation device 14 relative to a horizontal vector. The surgical orientation device 14 and/or the reference sensor device 16 can include one or more sensors to determine the direction of gravity. In some embodiments, the surgical orientation device 14 and/or the reference sensor device 16 can include an accelerometer.

The rotation angle of the surgical orientation device 14 can correspond to the posterior condyle angle. The system 510 can record the angle of rotation in extension and/or flexion. The rotation angle of the surgical orientation device 14 can correspond to the posterior condyle angle related to an implant or implant guide. In some embodiments, the cutting block or drill guide provided with the implant by the implant manufacturer can be adjustable based on the posterior condyle angle. In some embodiments, an implant from a plurality of implants can be selected based on the posterior condyle angle.

The system 510 can perform one or more calculations related to the rotation angle of the surgical orientation device 14. The system 510 can perform one or more calculations related to the distraction distance. The system 510 can be utilized to provide a visual indication of the medial distraction distance. The system 510 can be utilized to provide a visual indication of the lateral distraction distance. The system 510 can be configured to measure the tension within the soft tissue on the medial and/or lateral sides of the knee joint. The surgical orientation device 14 can be configured to display the force or tension on each side.

In some embodiments, the user can release one or more ligaments in the knee joint to balance the soft tissue on the medial and/or lateral sides of the knee joint. The user can release soft tissue when the knee is in extension for symmetry of the extension gap. The user can release soft tissue when the knee is in flexion for symmetry of the flexion gap. The user can release soft tissue when the knee is in extension or flexion for mechanical axis alignment between the femur and the tibia. The user can release soft tissue to reduce the rotation angle of the surgical orientation device 14. The user can release soft tissue to increase the rotation angle of the surgical orientation device 14. In some methods, the user can nick or cut soft tissue to adjust for laxity of the knee joint. The user can perform soft tissue balancing until the tibia and the femur are at the desired angle. The user can perform soft tissue balancing until the surgical orientation device 14 displays the desired angle. In some methods, the soft tissue is modified only in extension. In some methods, the soft tissue is modified only in flexion. In some methods, the soft tissue is modified in both flexion and extension. In some methods, the soft tissue is not modified.

D. Advantages

The Total Knee Arthroplasty (TKA) market is divided. Systems typically focus on alignment or balancing. For alignment system, there is measured resection. The resection or cut is aligned with bony or anatomic landmarks. Tension is subsequently addressed. For balancing systems, there is gap balancing. The soft tissue or ligaments in the knee joint are balanced. There are typically rectangular cuts on the balanced knee.

Figure 20A:
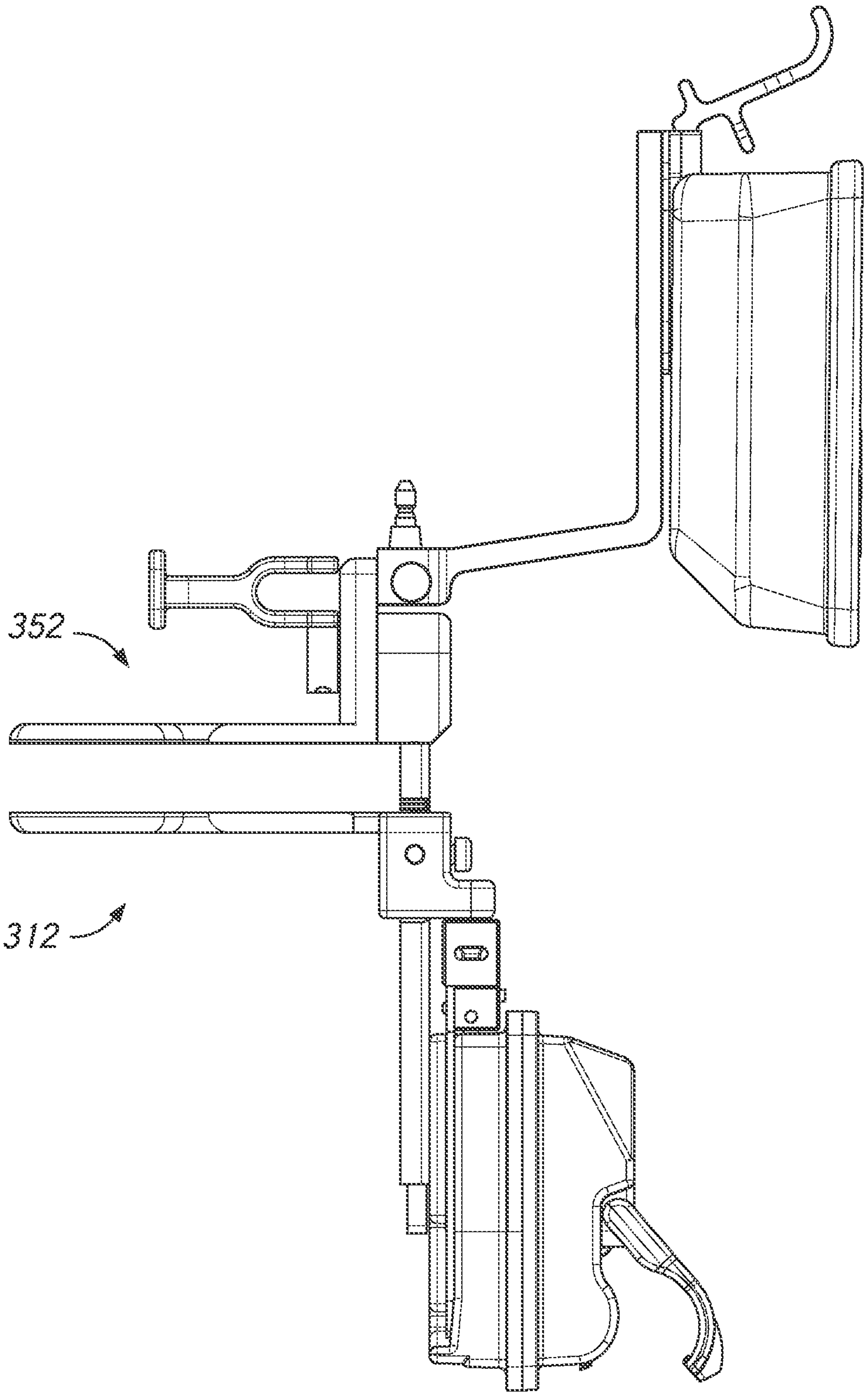
FIGS. 20A-20B illustrate the femoral preparation and knee distraction system of FIG. 3A.
Figure 20B:
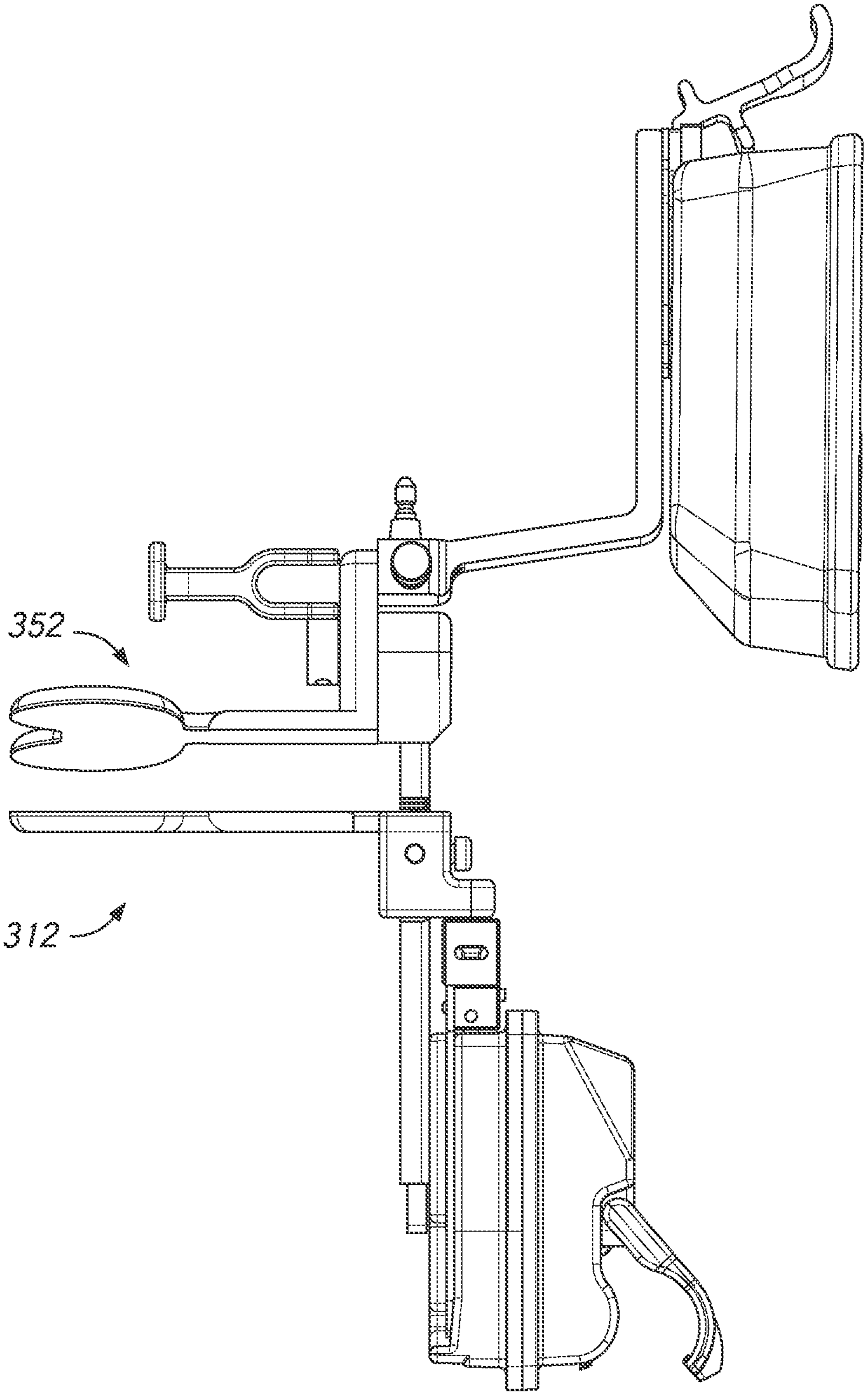
Figure 20C:
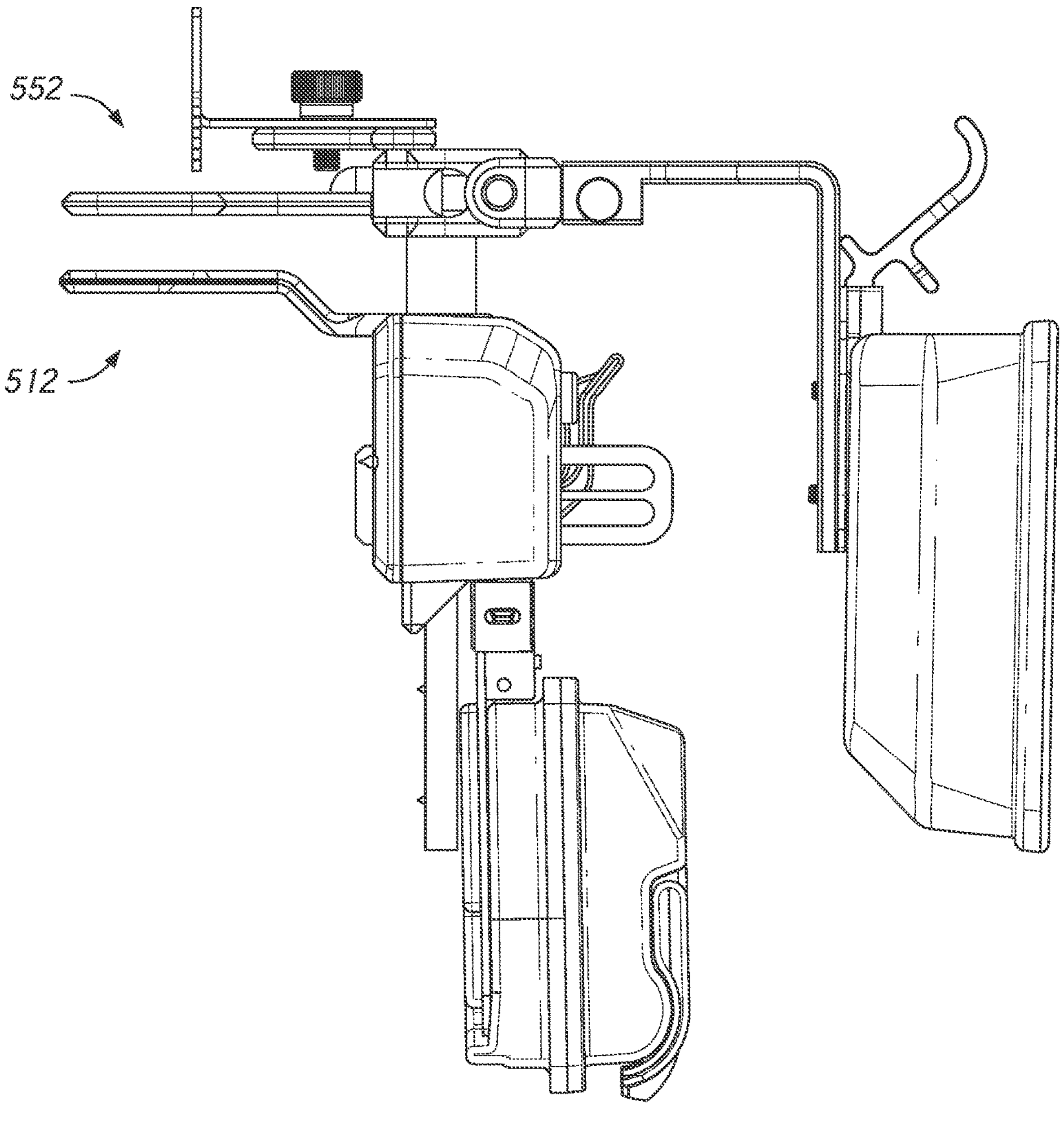
FIGS. 20C-20D illustrate the femoral preparation and knee distraction system of FIG. 13A.
Figure 20D:
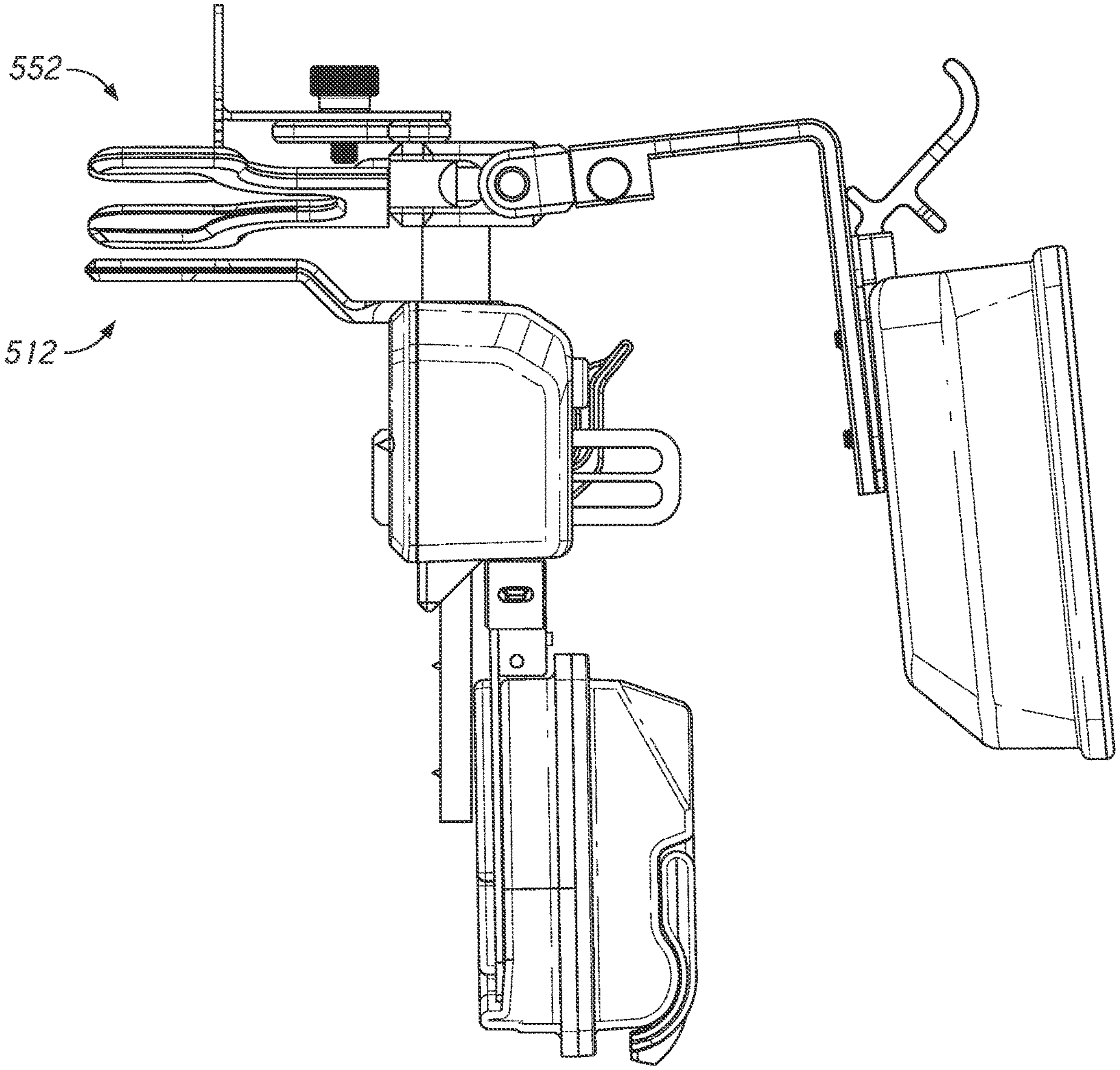

FIGS. 20A-20B illustrate the system 310. FIGS. 20C-20D illustrate the system 510. FIGS. 20A and 20C, illustrate the systems 310, 510 in distraction positions wherein the tibial system 312, 512 is separated a distance from the femoral system 352, 552. As described herein, this separation can be achieved by an actuation system including the post 332, 532. For instance, a rack and pinion can be utilized to exert a force. The femoral system 352, 552 translates relative to the tibial system 312, 512 due to the movement of the post 332, 532. The femoral system 352, 552 is translationally coupled to the post 332, 532. As described herein, the femoral system 352, 552 can include the post mount 366, 566 that translate the femoral system 352, 552 with the post 332, 532. The resection guide 580 or the drill guide 380 can be coupled to the post mount 366, 566 such that the resection guide 580 or the drill guide 380 translates with the femoral system 352, 552.

FIGS. 20B and 20D, illustrate the systems 310, 510 in a distraction and rotation positions wherein the tibial system 312, 512 is separated a distance from the femoral system 352, 552 and the femoral system 352, 552 is rotated relative the tibial system 312, 512. As described herein, the femoral system 352, 552 can include a femoral baseplate 354, 554 that can be configured to rotate relative to the post 332, 532. As described herein, the femoral baseplate 354 is coupled to extension member 360 which includes the second coupler 374. The femoral baseplate 354 and the second coupler 374 form a unitary structure that is configured to rotate about the rotational interface 368. As described herein, the femoral baseplate 554 is coupled to extension member 560 which extends through the post mount 566 to the interface 568. The interface 568 includes the second coupler 574. Rotation of the femoral baseplate 554 along one axis changes to rotation of the interface 568 about a second axis. In some embodiments, the system 510 converts the rotation about one axis to a rotation about the other axis to improve accuracy of the inertial sensors. The interface 568 can pivot upward and downward as the femoral baseplate 554 is rotated. While all of the components of the femoral system 552 are rotationally linked, the interface 568 rotates about a different axis of rotation than the femoral baseplate 554.

The system 310, 510 can be integrated with the femoral preparation system 10 and/or the tibial preparation system 210 described herein. The system 310, 510 provides a solution for balancing. The system 310, 510 integrates soft tissue balancing functionality. The system 310, 510 is simple, streamlined system that can be integrated in the workflow with alignment systems. The femoral preparation system 10, the tibial preparation system 210 and/or the system 310 can allow the user to produce an aligned, balance posterior condyle cut.

The femoral preparation system 10, the tibial preparation system 210 and/or the system 310, 510 can provide angular precision and accuracy via the inertial sensors. The femoral preparation system 10, the tibial preparation system 210 and/or the system 310, 510 utilize the surgical orientation device 14 and/or the reference sensor device 16. The surgical orientation device 14 and/or the reference sensor device 16 comprise one or more inertial sensors as described herein. The surgical orientation device 14 and/or the reference sensor device 16 comprise one or more accelerometers. The surgical orientation device 14 and/or the reference sensor device 16 comprise one or more gyroscopes.

The femoral preparation system 10, the tibial preparation system 210 and/or the system 310, 510 can provide a controlled, known distraction force. The post 332, 532 can be translated via the adjustment device 336, 536. In some embodiments, the rotation of the adjustment device 336, 536 can correlate with a known force or pressure. In some embodiments, one rotation of the adjustment device 336, 536 can correspond to 40-50 N of force, and two rotations of the adjustment device 336, 536 can correspond to 80-100 N of force. In some embodiments, the adjustment device 336, 536 can be configured to exert between 150 N and 200 N of force. In some embodiments, the tibial baseplate 314, 514 can include one or more sensors to measure force. In some embodiments, the femoral baseplate 354, 554 can include one or more sensors to measure force. The surgical orientation device 14 and/or the reference sensor device 16 can record the force measurement. The surgical orientation device 14 and/or the reference sensor device 16 and store the force measurement.

The femoral preparation system 10, the tibial preparation system 210 and/or the system 310, 510 can include an in-field graphic user interface. The femoral preparation system 10, the tibial preparation system 210 and/or the system 310, 510 can include the surgical orientation device 14. The surgical orientation device 14 can include the display 26. The display 26 can provide an on-screen graphic of one or more parameters to be used during the procedure. For example, a numerical display can be provided for one or more measurements, such as flexion-extension angles, varus-valgus angles, rotation angles (e.g. angles of rotation about the mechanical axis of the leg, the angle of the posterior condyles, etc.), or distances (e.g., extension distances of the post 332, 532). The on-screen graphic can comprise alphanumeric text or symbols of various colors, one or more background colors, one or more icons, one or more GUI images, animations, arrows, and the like. The display 26 can also provide a textual, audible, or other visual notification to the user that the current measurements are outside a pre-determined range. The surgical orientation device 14 can be controlled by the user within the surgical field. The user can view the display 26 within the surgical field. The user can interact with the surgical orientation device 14 within the surgical field (e.g., depress a button, record a measurement, receive instructions, interact with user input 28, read display 26, etc.).

The femoral preparation system 10, the tibial preparation system 210 and/or the system 310, 510 can be open platform. The system 310, 510 can work with leading implants. The drill guide 380 can be provided by the implant manufacturer. The drill guide 380 can provide openings 382 corresponding to measurements for cutting blocks provided by the implant manufacturers. The openings 382 can correspond with a cutting block 394 provided by the implant manufacturer. The system 310 can provide a drill guide 380 for 4-in-1 block alignment to tibial resection. The drill guide 380 can be used to make holes that will locate the cutting block 394, as described herein. The resection guide 580 can be utilized to mark a line on the femur. In some embodiments, the resection guide 580 includes notches 582 which enable the user to draw a dot, line or tick mark corresponding to the notch 582. These marks can then be used to draw a line once the resection guide 580 is removed. Other configurations are contemplated to draw a resection line. The resection guide 580 can include one or more openings to draw a dot. The resection guide 580 can include one or more slots to draw a line or line segment. The resection guide 580 can include one or more flat surfaces to draw a line or line segment. Other configurations of marking a resection line are contemplated.

The system 310, 510 can calculate, display, record, and store various measurements and/or calculations. The data can be stored during the length of the procedure. The data can be stored for post-operative use. The system 310, 510 can calculate the angle of the posterior condyles. The system 310, 510 can display the angle of the posterior condyles. The system 310, 510 can record the angle of the posterior condyles. The system 310, 510 can store the angle of the posterior condyles. As described herein, the system 310, 510 can allow for the placement of the reference sensor device 16 in two or more orientations when the system 310, 510 calculates the angle of the posterior condyles. The system 310, 510 can allow for the placement of the reference sensor device 16 in two perpendicular orientations. The longitudinal axis of the reference sensor device 16 can be parallel to the tibial baseplate 314, 514 when the system 310, 510 calculates the angle of the posterior condyles. The longitudinal axis of the surgical orientation device 14 can be perpendicular to the tibial baseplate 314 when the system 310, 510 calculates the angle of the posterior condyles.

The system 310, 510 can calculate the distraction distance in extension. The system 310, 510 can display the distraction distance in extension. The system 310, 510 can record the distraction distance in extension. The system 310, 510 can store the distraction distance in extension. The system 310, 510 can calculate the distraction distance in flexion. The system 310, 510 can display the distraction distance in flexion. The system 310, 510 can record the distraction distance in flexion. The system 310, 510 can store the distraction distance in flexion. The system 310, 510 can compare the distraction distance in flexion and the distraction distance in extension. The system 310, 510 can calculate an adjustment distance if the distraction distance in flexion and the distraction distance in extension are different. The user can adjust the drill guide 380 by the adjustment distance. The user can utilize parallel rows of openings 382 separated by the adjustment distance. The user can utilize the resection guide 580 related to the distraction distance. The user can utilize parallel rows of notches 582 to mark a line for the posterior cut.

The system 310, 510 can calculate the medial distraction distance. The system 310, 510 can calculate the lateral distraction distance. The medial distraction distance and the lateral distraction distance can be determined based in part on the distraction distance. The medial distraction distance and the lateral distraction distance can be determined based in part on the angle of the posterior condyles. The system 310, 510 can display the medial distraction distance. The system 310, 510 can display the lateral distraction distance. The system 310, 510 can record the medial distraction distance. The system 310, 510 can record the lateral distraction distance. The system 310, 510 can store distraction distance. The system 310, 510 can store the lateral distraction distance. The system 310, 510 can provide medial distraction distance and/lateral distraction distance dynamically. The system 310, 510 can provide medial distraction distance and/lateral distraction distance in real-time.

The system 310, 510 can provide cut verification. The system 310, 510 can provide cut verification of the distal femoral cut (DFC). The DFC removes a distal (i.e., lower) portion of the femur. The system 310, 510 can provide cut verification of the posterior femoral cut (PFC). The PFC removes a portion of the posterior condyle. The system 510 can be utilized to mark the femur related to the PFC. The system 310, 510 can provide cut verification for one or more cuts of the femur. The system 310, 510 can provide cut verification for one or more cuts of the tibia.

The system 310, 510 can utilize the surgical orientation device 14 and/or the reference sensor device 16 of the femoral preparation system 10 and the tibial preparation system 210 described herein. The system 310, 510 can provide an attachment for the surgical orientation device 14. The system 310, 510 can provide an attachment for the reference sensor device 16. The system 310, 510 can provide an attachment for the drill guide 380. The system 310, 510 can allow attachment of the resection guide 580. The systems described herein can be compatible with any subsystem described herein including the guides described herein. The drill guide 380 can couple to the tibial baseplate 314. The drill guide 380 can be rotationally independent from the femoral baseplate 354. The drill guide 380 guides drill holes to 4-in-1 block specifications. The drill guide 380 can guide the cutting block to be parallel to the tibial resection. The resection guide 580 can couple to the tibial baseplate 514. The resection guide 580 can be rotationally independent from the femoral baseplate 554. The resection guide 580 can guide the posterior cut to be parallel to the tibia resection.

The system 310, 510 can provide a distraction force. The system 310, 510 can mechanically distract in extension and flexion. The system 310, 510 can provide a known distraction force. In some embodiments, the known distraction force is between 80 N and 100 N. In some embodiments, the distraction force is between 150 N and 200 N. In some embodiments, the known distraction force is greater than 50 N, greater than 60 N, greater than 70 N, greater than 80 N, greater than 90 N, greater than 100 N, greater than 110 N, greater than 120 N, greater than 130 N, greater than 140 N, greater than 150 N, greater than 160 N, greater than 170 N, greater than 180 N, greater than 190 N, greater than 200 N, greater than 210 N, greater than 220 N, greater than 230 N, greater than 240 N, greater than 250 N, etc.

The display 26 can provide a different way to determine the distraction distance than visual inspection of a scale. The display 26 can provide a digital output of the distraction distance. The display 26 can provide a faster way to determine the distraction distance than visual inspection of a scale. The display 26 can provide a more accurate way to determine the distraction distance than visual inspection of a scale. The display 26 can be easier to use than a scale visual to the user. The data output of the display 26 can be in real-time. The display 26 can be positioned within the surgical field. The display 26 can be positioned to be visible to the user during the procedure.

The display 26 can provide a visual reference to key anatomical features. The display 26 can provide a visual reference to Whiteside's Line. The display 26 can provide a visual reference to Epicondyle axis. The display 26 can provide a visual reference to the mechanical axis.

The system 310, 510 can provide a balanced, rectangular flexion gap. The system 310, 510 can provide an improvement in the ability to measure a balanced flexion gap. The system 310, 510 can provide an improvement in the ability to achieve a balanced flexion gap. The system 310, 510 can provide a guide to rotationally align the femoral component. The system 310, 510 can provide an improvement in recording measurements during a procedure. The system 310, 510 can provide an improvement in storing measurements during a procedure.

In some methods of use, the procedure can include one or more of the following steps. The user can complete distal femoral resection. The distal femoral resection can be perpendicular to mechanical axis of femur in the coronal plane. The user can use the femoral preparation system 10 described herein. The user can complete tibial resection. The tibial resection can be perpendicular to mechanical axis of femur in the coronal plane. The user can use the tibial preparation system 210 described herein. The user can insert the system 310, 510 between the tibia and femur. The user can distract the knee in full extension.

The system 310, 510 can include the surgical orientation device 14 and the reference sensor device 16 described herein. In some embodiments, the system 310, 510 can use gyro propagation to measure coronal plane angle between tibial and femoral resections. The user can mount the surgical orientation device 14 on femur rigid body. For instance, the user can mount the surgical orientation device 14 on the second coupler 374, 574. The reference sensor device 16 is at a fixed angle relative to the surgical orientation device 14. For instance, the user can mount the reference sensor device 16 on the third coupler 378. The surgical orientation device 14 and the reference sensor device 16 can be zeroed. The gyroscopes within the surgical orientation device 14 and the reference sensor device 16 can be zeroed. The reference sensor device 16 can be moved to the tibia rigid body. For instance, the user can mount the reference sensor device 16 on the first coupler 324, 524. The user can read the tibio-femoral angle on the display 24 of the surgical orientation device 14.

The user can release ligaments as needed to achieve target angle. In some methods, the target angle is zero. The user can record the distraction distance (extension gap). The user can remove the system 310, 510 from the leg in extension.

The user can flex the knee 90°. The user can insert the system 310, 510 between the tibia and femur. The user can apply distraction in flexion. The user can read the flexion gap on the display 24 of the surgical orientation device 14. The user can read the flexion gap visually from the markings 340, 540. The user can calculate the anterior-posterior shift needed to match flexion and extension gaps.

In some methods of use, the user can mount the drill guide 380 and drill holes with the appropriate AP shift from the preceding step. In some methods of use, the user can measure posterior condyle angle on surgical orientation device 14 from accelerometer measurements. The user can set implant sizing/drill guide to this angle. In some methods of use, the user either mounts the drill guide 380 and drill holes with the appropriate AP shift from preceding step or measures posterior condyle angle on surgical orientation device 14 from accelerometer measurements and sets implant sizing/drill guide to this angle. In some embodiments, no soft tissue releases are need in flexion because 4-in-1 cutting block 394 will be located with posterior resection slot parallel to tibial resection by correct alignment of drilled guide holes. The method can include mounting the implant sizing/drill guide on distal resection surface. The method can include drilling holes if not previously completed. The user can read implant size and choose appropriate 4-in-1 cutting block. The user can remove sizing/drill guide. The user can attach cutting block, locating using drilled holes. The user can complete resections.

In some methods of use, the user can mount the resection guide 580 and cut the femur with the appropriate AP shift from the preceding step. In some methods of use, the user can measure posterior condyle angle on surgical orientation device 14 prior the posterior cut. In some embodiments, the posterior condyle angle is measured only in flexion. The user can set implant sizing/drill guide to this angle. In some methods, the user makes the posterior cut. In some methods, the user makes one or more additional cuts based on the posterior cut. In some methods, the user makes one or more additional cuts based on specification from the implant manufacturer. In some methods, the user makes one or more additional cuts based a cutting guide provided by the manufacturer. In some embodiments, soft tissue is released in extension to balance the extension gap. In some embodiments, soft tissue is not released in flexion.

While the systems and methods presented herein are described in the context of a knee joint replacement procedure, the systems and/or their components and methods can similarly be used in other types of medical procedures, including but not limited to shoulder and hip replacement procedures.

Additionally, while the systems and methods presented herein are described in the context of individual components and assemblies, in some embodiments one or more of the assemblies can be provided in the form of a kit for use by a surgeon. For example, in some embodiments a kit can comprise each of the components of the femoral preparation system 10 and the tibial preparation system 210 described above. In some embodiments, a kit may comprise only the surgical orientation device 14 and reference sensor device 16. In some embodiments a kit may comprise only the femoral preparation system 10, or only the tibial preparation system 210. In some embodiments a kit may comprise only the system 310, 510. Various other combinations and kits are also possible.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. An orthopedic system comprising:

a tibial baseplate of a tibial member, wherein the tibial baseplate is configured to be inserted within a joint space between a tibia and a femur of a knee joint, wherein the tibial baseplate is configured to contact the tibia while distracting the knee joint;

a femoral baseplate of a femoral member, wherein the femoral baseplate is configured to be inserted within the joint space, wherein the femoral baseplate is configured to contact the femur while distracting the knee joint;

an adjustment device coupling the tibial member and the femoral member, the adjustment device enabling linear translation between the tibial member and the femoral member to distract the joint, wherein the femoral baseplate is configured to rotate relative to the tibial baseplate;

a surgical orientation device coupled or configured to couple to one of the tibial member or the femoral member, the surgical orientation device comprising:

a housing, and an inertial sensor configured to monitor the orientation of the surgical orientation device; and a reference sensor device coupled or configured to couple to the other of the tibial member or the femoral member, the reference sensor device comprising:

a housing, and an inertial sensor configured to monitor the orientation of the reference sensor device, wherein the surgical orientation device and/or the reference sensor device is configured to calculate an angle as the femoral baseplate rotates.

2. The system of claim 1, wherein the surgical orientation device and the reference sensor device are configured to measure an extension gap.

3. The system of claim 1, wherein the surgical orientation device and the reference sensor device are configured to measure a flexion gap.

4. The system of claim 1, wherein the surgical orientation device and/or the reference sensor device are configured to store data related to a distraction.

5. The system of claim 1, wherein the surgical orientation device and/or the reference sensor device are configured to store a distraction distance when the leg is in extension.

6. The system of claim 1, wherein the surgical orientation device and/or the reference sensor device are configured to store a distraction distance when the leg is in flexion.

7. The system of claim 1, further comprising a femoral jig assembly comprising a first coupling device and a second coupling device, wherein the first coupling device is configured to couple the surgical orientation device and the femoral jig assembly, wherein the second coupling configured to couple the reference sensor device and the femoral jig assembly.

8. The system of claim 1, wherein the femoral baseplate of the femoral member is configured to contact a resected surface of the femur.

9. The system of claim 1, further comprising a tibial jig assembly comprising a first interface and a second interface, wherein the first interface is configured to couple the surgical orientation device and the tibial jig assembly, wherein the second interface is configured to couple the reference sensor device and the tibial jig assembly.

10. The system of claim 1, wherein the surgical orientation device is configured to display information in real-time.

11. The system of claim 1, wherein the tibial baseplate of the tibial member is configured to contact a resected surface of the tibia.

12. An orthopedic orientation system comprising:

a tibial baseplate of a tibial member, wherein the tibial baseplate is configured to be inserted within a joint space between a tibia and a femur of a knee joint, wherein the tibial baseplate is configured to contact the tibia while distracting the knee joint;

a femoral baseplate of a femoral member, wherein the femoral baseplate is configured to be inserted within the joint space, wherein the femoral baseplate is configured to contact the femur while distracting the knee joint;

an adjustment device coupling the tibial member and the femoral member, the adjustment device enabling linear translation between the tibial member and the femoral member to distract the joint, wherein the femoral baseplate is configured to rotate relative to the tibial baseplate;

a surgical orientation device coupled or configured to couple to one of the tibial member or the femoral member, the surgical orientation device comprising:

a housing, and an inertial sensor; and a reference sensor device coupled or configured to couple to the other of the tibial member or the femoral member, the reference sensor device comprising:

a housing, and an inertial sensor, wherein the surgical orientation device and/or the reference sensor device are configured to calculate changes in angle relative to each other; and a mounting feature configured to allow a drill guide to be mounted parallel to the tibial member.

13. The system of claim 12, wherein the mounting feature remains in position as the femoral member rotates.

14. The system of claim 12, further comprising the drill guide.

15. The system of claim 12, wherein a display screen of the surgical orientation device is configured to display a measurement to facilitate one or more cuts.

16. The system of claim 15, wherein the measurement is a distraction distance or an angle.

17. The system of claim 12, wherein the drill guide is configured to allow a user to place one or more pins to aid in mounting a cutting block.

18. The system of claim 12, wherein the drill guide is a modular device configured to be coupled to and decoupled from the mounting feature.

* * * * *